United States Patent
Liu et al.

(10) Patent No.: US 11,174,319 B2
(45) Date of Patent: Nov. 16, 2021

(54) BINDING MOLECULE SPECIFIC FOR CD73 AND USE OF BINDING MOLECULE

(71) Applicant: JACOBIO PHARMACEUTICALS CO., LTD., Beijing (CN)

(72) Inventors: Qinghao Liu, Beijing (CN); Wenlai Zhou, Beijing (CN); Haiyan Yang, Beijing (CN); Hongling Wang, Beijing (CN)

(73) Assignee: JACOBIO PHARMACEUTICALS CO., LTD., Beijing (CN)

( * ) Notice: Subject to any disclaimer, the term of this patent is extended or adjusted under 35 U.S.C. 154(b) by 0 days.

(21) Appl. No.: 17/240,141

(22) Filed: Apr. 26, 2021

(65) Prior Publication Data

US 2021/0253730 A1    Aug. 19, 2021

Related U.S. Application Data

(63) Continuation of application No. PCT/CN2020/094489, filed on Jun. 5, 2020.

(51) Int. Cl.
*C07K 16/00* (2006.01)
*A61K 39/395* (2006.01)
*C07K 16/28* (2006.01)
*A61P 35/00* (2006.01)
*A61K 39/00* (2006.01)

(52) U.S. Cl.
CPC .......... *C07K 16/2896* (2013.01); *A61P 35/00* (2018.01); *A61K 2039/505* (2013.01); *C07K 2317/565* (2013.01)

(58) Field of Classification Search
CPC combination set(s) only.
See application file for complete search history.

*Primary Examiner* — Mark Halvorson
(74) *Attorney, Agent, or Firm* — Robin L. Teskin; Baker, Donelson, Bearman, Caldwell & Berkowitz PC

(57) ABSTRACT

A binding molecule specific for CD73 and a use of the binding molecule. Specifically, provided are a separate antibody binding CD73 and inhibiting the activity of CD73 or an antigen binding part of the separate antibody, and a use of the separate antibody or the antigen binding part thereof in treatment of diseases; also provided are a nucleic acid molecule encoding the separate antibody or the antigen binding part thereof, an expression vector for expressing the separate antibody or the antigen binding part thereof, a host cell, and a preparation method.

19 Claims, 13 Drawing Sheets

Specification includes a Sequence Listing.

BINDING MOLECULE SPECIFIC FOR CD73 AND USE OF BINDING MOLECULE

CROSS-REFERENCE TO RELATED APPLICATIONS

This application is a continuation application of Int'l Appl. No. PCT/CN2020/094489, filed Jun. 5, 2020, which claims priority to PCT/CN2019/090366, filed Jun. 6, 2019, each and all of which are incorporated herein by reference in their entirety.

SEQUENCE DISCLOSURE

This application includes as part of its disclosure an electronic sequence listing text file named "11584980003601.txt", having a size of 196,265 and created Apr. 26, 2021, which is hereby incorporated by reference in its entirety.

TECHNICAL FIELD

This invention relates to the isolated antibody or antigen-binding fragment thereof specifically binding to CD73, this invention also relates to the use of the isolated antibody or antigen-binding fragment thereof in treatment of diseases, and this invention relates to the therapeutic method of the isolated antibody or antigen-binding fragment thereof.

BACKGROUND ART

CD73 (ecto-5'-nucleotidase) is membrane-bound/free protein with a size of about 70 kDa and consists of N-terminal and C-terminal subunits and a flexible link. The C-terminus is anchored to the cell membrane through glycosyl-phosphatidylinositol (GPI). CD73 exerts an enzymatic activity through switching between open and closed conformational states (Knapp, K. et al. (2012), Structure, 20(12), 2161-2173). In the adenosine pathway, CD73 can continue to hydrolyze AMP produced by CD39 to adenosine. Adenosine exerts various immunosuppressive effects, such as inhibiting the proliferation of CD4+T and CD8+T, inhibiting NK cell activity, promoting Treg proliferation, and the like.

It has been widely reported that CD73 was highly expressed in various tumor such as gastric cancer, triple negative breast cancer, non-small-cell adenocarcinoma, rectal adenocarcinoma, colorectal cancer, renal cell carcinoma, ovarian cancer, prostate cancer, oral squamous cell carcinoma, head and neck squamous cell carcinoma and so on, and high CD73 expression was associated with poor prognosis (Vijayan, D. et al., (2017), Nature reviews Cancer, 17, 709). Increased expression of CD73 in tumor microenvironment was associated with tumor proliferation, metastasis, neovascularization, and poor survival of the patients (Allard, B. et al., (2017), Immunological reviews, 276 (1), 121-144). With the high expression of CD73, the increased adenosine inhibits tumor immunity by activating tumor intrinsic and host-mediated tumor-promoting mechanisms, restricting immune cell infiltration and production of cytotoxicity and cytokines (such as interferon), and causes strong immuno-suppression (Ohta, A. et al., (2016), Front Immunol, 7, 109). Immunosuppression is a typical characteristic of cancer, and it is important to overcome the inhibitory barrier. Therefore, it is a highly potential therapeutic direction of inhibiting the production of adenosine in the tumor microenvironment by inhibiting CD73, thereby activating immunity and inhibiting tumor growth.

Antibodies can inhibit the enzymatic activity of CD73 by antagonizing CD73 allosteric to the active form, but there is no report of any antibody that can directly bind to the CD73 active site to inhibit its enzyme activity. Meanwhile, although CD73 is a very potential therapeutic target, more research is needed to verify the prognosis of CD73 targets and to develop related drugs and combination therapies.

SUMMARY OF INVENTION

The invention provide an isolated antibody or antigen-binding fragment specifically binding for CD73 and uses thereof in the treatment diseases.

In one respect, the invention provide an isolated antibody or antigen-binding fragment thereof comprising a heavy chain variable region that comprises HCDR1, HCDR2, HCDR3; and a light chain variable region that comprises LCDR1, LCDR2, LCDR3, wherein:
(a) HCDR1 comprises an amino acid sequence selected from the group consisting of SEQ ID NOs: 5, 18, 31, 43 and 56, and conservative modifications thereof;
(b) HCDR2 comprises an amino acid sequence selected from the group consisting of SEQ ID NOs: 6, 19, 32, 44 and 57, and conservative modifications thereof;
(c) HCDR3 comprises an amino acid sequence selected from the group consisting of SEQ ID NOs: 7, 20, 33, 45 and 58, and conservative modifications thereof;
(d) LCDR1 comprises an amino acid sequence selected from the group consisting of SEQ ID NOs: 10, 23, 36, 48 and 61, and conservative modifications thereof;
(e) LCDR2 comprises an amino acid sequence selected from the group consisting of SEQ ID NOs: 11, 24, 37, 49 and 62, and conservative modifications thereof and
(0 LCDR3 comprises an amino acid sequence selected from the group consisting of SEQ ID NOs: 12, 25, 38, 50 and 63, and conservative modifications thereof.

In some embodiments, the isolated antibody or antigen-binding fragment thereof comprises:
1) (a) HCDR1 comprising SEQ ID NO: 5, (b) HCDR2 comprising SEQ ID NO: 6, (c) HCDR3 comprising SEQ ID NO: 7, (d) LCDR1 comprising SEQ ID NO: 10, (e) LCDR2 comprising SEQ ID NO: 11, and (0 LCDR3 comprising SEQ ID NO: 12;
2) (a) HCDR1 comprising SEQ ID NO: 18, (b) HCDR2 comprising SEQ ID NO: 19, (c) HCDR3 comprising SEQ ID NO: 20, (d) LCDR1 comprising SEQ ID NO: 23, (e) LCDR2 comprising SEQ ID NO: 24, and (f) LCDR3 comprising SEQ ID NO: 25;
3) (a) HCDR1 comprising SEQ ID NO: 31, (b) HCDR2 comprising SEQ ID NO: 32, (c) HCDR3 comprising SEQ ID NO: 33, (d) LCDR1 comprising SEQ ID NO: 36, (e) LCDR2 comprising SEQ ID NO: 37, and (f) LCDR3 comprising SEQ ID NO: 38;
4) (a) HCDR1 comprising SEQ ID NO: 43, (b) HCDR2 comprising SEQ ID NO: 44, (c) HCDR3 comprising SEQ ID NO: 45, (d) LCDR1 comprising SEQ ID NO: 48, (e) LCDR2 comprising SEQ ID NO: 49, and (0 LCDR3 comprising SEQ ID NO: 50; or
5) (a) HCDR1 comprising SEQ ID NO: 56, (b) HCDR2 comprising SEQ ID NO: 57, (c) HCDR3 comprising SEQ ID NO: 58, (d) LCDR1 comprising SEQ ID NO: 61, (e) LCDR2 comprising SEQ ID NO: 62, and (f) LCDR3 comprising SEQ ID NO: 63.

In some embodiments, the isolated antibody or antigen-binding fragment thereof comprises:(a) HCDR1 comprising SEQ ID NO: 5, (b) HCDR2 comprising SEQ ID NO: 6, (c) HCDR3 comprising SEQ ID NO: 7, (d) LCDR1 comprising SEQ ID NO: 10, (e) LCDR2 comprising SEQ ID NO: 11, and (0 LCDR3 comprising SEQ ID NO: 12.

In some embodiments, the isolated antibody or antigen-binding fragment thereof comprises:(a) HCDR1 comprising SEQ ID NO: 18, (b) HCDR2 comprising SEQ ID NO: 19, (c) HCDR3 comprising SEQ ID NO: 20, (d) LCDR1 comprising SEQ ID NO: 23, (e) LCDR2 comprising SEQ ID NO: 24, and (0 LCDR3 comprising SEQ ID NO: 25.

In some embodiments, the isolated antibody or antigen-binding fragment thereof comprises:(a) HCDR1 comprising SEQ ID NO: 31, (b) HCDR2 comprising SEQ ID NO: 32, (c) HCDR3 comprising SEQ ID NO: 33, (d) LCDR1 comprising SEQ ID NO: 36, (e) LCDR2 comprising SEQ ID NO: 37, and (0 LCDR3 comprising SEQ ID NO: 38.

In some embodiments, the isolated antibody or antigen-binding fragment thereof comprises:(a) HCDR1 comprising SEQ ID NO: 43, (b) HCDR2 comprising SEQ ID NO: 44, (c) HCDR3 comprising SEQ ID NO: 45, (d) LCDR1 comprising SEQ ID NO: 48, (e) LCDR2 comprising SEQ ID NO: 49, and (0 LCDR3 comprising SEQ ID NO: 50.

In some embodiments, the isolated antibody or antigen-binding fragment thereof comprises:(a) HCDR1 comprising SEQ ID NO: 56, (b) HCDR2 comprising SEQ ID NO: 57, (c) HCDR3 comprising SEQ ID NO: 58, (d) LCDR1 comprising SEQ ID NO: 61, (e) LCDR2 comprising SEQ ID NO: 62, and (0 LCDR3 comprising SEQ ID NO: 63.

In some embodiments, the isolated antibody or antigen-binding fragment thereof comprises:
(i) the heavy chain variable region (VH) comprising an amino acid sequence which has at least 85% identity to the amino acid sequences selected from the group consisting of SEQ ID NOs: 3, 16, 29, 41, 54, 66, 67, 76, 77 and 78, and conservative modifications thereof and
(ii) the light chain variable region (VL) comprising an amino acid sequence which has at least 85% identity to the amino acid sequence selected from the group consisting of SEQ ID NOs: 8, 21, 34, 46, 59, 68, 69, 70, 79 and 80, and conservative modifications thereof.

In some embodiments, the heavy chain variable regions comprise an amino acid sequence which has at least 90%, at least 95%, at least 96%, at least 97%, at least 98%, at least 99%, or 100% identity to the heavy variable regions selected from the group of (i), and the light chain variable regions comprise an amino acid sequence which has at least 90%, at least 95%, at least 96%, at least 97%, at least 98%, at least 99%, or 100% identity to the light variable regions selected from the group of (ii).

In some embodiments, the isolated antibody or antigen-binding fragment thereof comprises:
1) a heavy chain variable region (VH) that comprises an amino acid sequence which has at least 85% identity to the amino acid sequences of SEQ ID NO: 3, and a light chain variable region (VL) that comprises an amino acid sequence which has at least 85% identity to the amino acid sequences of SEQ ID NO: 8;
2) a heavy chain variable region (VH) that comprises an amino acid sequence which has at least 85% identity to the amino acid sequences of SEQ ID NO: 16, and a light chain variable region (VL) that comprises an amino acid sequence which has at least 85% identical to the amino acid sequences of SEQ ID NO:21;
3) a heavy chain variable region (VH) that comprises an amino acid sequence which has at least 85% identity to the amino acid sequences of SEQ ID NO: 29, and a light chain variable region (VL) that comprises an amino acid sequence which has at least 85% identity to the amino acid sequences of SEQ ID NO: 34;
4) a heavy chain variable region (VH) that comprises an amino acid sequence which has at least 85% identity to the amino acid sequences of SEQ ID NO: 41, and a light chain variable region (VL) that comprises an amino acid sequence which has at least 85% identity to the amino acid sequences of SEQ ID NO: 46;
5) a heavy chain variable region (VH) that comprises an amino acid sequence which has at least 85% identity to the amino acid sequences of SEQ ID NO: 54, and a light chain variable region (VL) that comprises an amino acid sequence which has at least 85% identity to the amino acid sequences of SEQ ID NO: 59;
6) a heavy chain variable region (VH) that comprises an amino acid sequence which has at least 85% identity to the amino acid sequences of SEQ ID NO: 66, and a light chain variable region (VL) that comprises an amino acid sequence which has at least 85% identity to the amino acid sequences of SEQ ID NO: 68;
7) a heavy chain variable region (VH) that comprises an amino acid sequence which has at least 85% identity to the amino acid sequences of SEQ ID NO: 66, and a light chain variable region (VL) that comprises an amino acid sequence which has at least 85% identity to the amino acid sequences of SEQ ID NO: 69;
8) a heavy chain variable region (VH) that comprises an amino acid sequence which has at least 85% identity to the amino acid sequences of SEQ ID NO: 66, and a light chain variable region (VL) that comprises an amino acid sequence which has at least 85% identity to the amino acid sequences of SEQ ID NO: 70;
9) a heavy chain variable region (VH) that comprises an amino acid sequence which has at least 85% identity to the amino acid sequences of SEQ ID NO: 67, and a light chain variable region (VL) that comprises an amino acid sequence which has at least 85% identity to the amino acid sequences of SEQ ID NO: 68;
10) a heavy chain variable region (VH) that comprises an amino acid sequence which has at least 85% identity to the amino acid sequences of SEQ ID NO: 67, and a light chain variable region (VL) that comprises an amino acid sequence which has at least 85% identity to the amino acid sequences of SEQ ID NO: 69;
11) a heavy chain variable region (VH) that comprises an amino acid sequence which has at least 85% identity to the amino acid sequences of SEQ ID NO: 67, and a light chain variable region (VL) that comprises an amino acid sequence which has at least 85% identity to the amino acid sequences of SEQ ID NO: 70;
12) a heavy chain variable region (VH) that comprises an amino acid sequence which has at least 85% identity to the amino acid sequences of SEQ ID NO: 76, and a light chain variable region (VL) that comprises an amino acid sequence which has at least 85% identity to the amino acid sequences of SEQ ID NO: 79;
13) a heavy chain variable region (VH) that comprises an amino acid sequence which has at least 85% identity to the amino acid sequences of SEQ ID NO: 76, and a light chain variable region (VL) that comprises an amino acid sequence which has at least 85% identity to the amino acid sequences of SEQ ID NO: 80;
14) a heavy chain variable region (VH) that comprises an amino acid sequence which has at least 85% identity to the amino acid sequences of SEQ ID NO: 77, and a light chain variable region (VL) that comprises an amino acid sequence which has at least 85% identity to the amino acid sequences of SEQ ID NO: 79;

15) a heavy chain variable region (VH) that comprises an amino acid sequence which has at least 85% identity to the amino acid sequences of SEQ ID NO: 77, and a light chain variable region (VL) that comprises an amino acid sequence which has at least 85% identity to the amino acid sequences of SEQ ID NO: 80;
16) a heavy chain variable region (VH) that comprises an amino acid sequence which has at least 85% identity to the amino acid sequences of SEQ ID NO: 78, and a light chain variable region (VL) that comprises an amino acid sequence which has at least 85% identity to the amino acid sequences of SEQ ID NO: 79;
17) a heavy chain variable region (VH) that comprises an amino acid sequence which has at least 85% identity to the amino acid sequences of SEQ ID NO: 78, and a light chain variable region (VL) that comprises an amino acid sequence which has at least 85% identity to the amino acid sequences of SEQ ID NO: 80.

In some embodiments, the isolated antibody or antigen-binding fragment thereof, wherein the heavy and light chain variable regions comprise an amino acid sequence at least 90%, at least 95%, at least 96%, at least 97%, at least 98%, at least 99%, or 100% identity to the heavy and light chain variable regions, respectively, selected from the group consisting of 1)-17).

In some embodiments, the isolated antibody is an IgG.

In some embodiments, the isolated antibody is an IgG1, IgG2 or IgG4.

In some embodiments, the isolated antibody is a monoclonal antibody, a chimeric antibody, a humanized antibody, a human engineered antibody, a human antibody, Fv, a single chain antibody (scFv), Fab, Fab', Fab'-SH or F(ab')2.

In some embodiments, the isolated antibody or antigen-binding fragment thereof comprising a heavy chain and a light chain, wherein:
(I) the heavy chain comprising an amino acid sequence which is at least 85% identity to the amino acid sequences selected from the group consisting of SEQ ID NOs: 13, 15, 26, 27, 39, 51, 52, 64, 71, 72, 81, 82, 83, 86, 87, 90, 91, 124, 125, 126 and 127, and conservative modifications thereof and
(II) the light chain comprising an amino acid sequence which is at least 85% identity to the amino acid sequences selected from the group consisting of SEQ ID NOs: 14, 28, 40, 53, 65, 73, 74, 75, 84, 85, 88 and 89, and conservative modifications thereof.

In some embodiments, the heavy chain comprises an amino acid sequence which has at least 90%, at least 95%, at least 96%, at least 97%, at least 98%, or 100% identity to the heavy chains selected from the group of (I), and the light chain comprises an amino acid sequence which has at least 90%, at least 95%, at least 96%, at least 97%, at least 98%, or 100% identity to the light chain selected from the group of (II).

In some embodiments, the isolated antibody or antigen-binding fragment thereof comprises:
1) a heavy chain that comprises an amino acid sequence which is at least 85% identity to the amino acid sequences of SEQ ID NO: 13, and a light chain that comprises an amino acid sequence which has at least 85% identity to the amino acid sequence of SEQ ID NO: 14;
2) a heavy chain that comprises an amino acid sequence which has at least 85% identity to the amino acid sequences of SEQ ID NO: 15, and a light chain that comprises an amino acid sequence which has at least 85% identity to the amino acid sequence of SEQ ID NO: 14;
3) a heavy chain that comprises an amino acid sequence which has at least 85% identity to the amino acid sequences of SEQ ID NO: 26, and a light chain that comprises an amino acid sequence which has at least 85% identity to the amino acid sequence of SEQ ID NO: 28;
4) a heavy chain that comprises an amino acid sequence which has at least 85% identity to the amino acid sequences of SEQ ID NO: 27, and a light chain that comprises an amino acid sequence which has at least 85% identity to the amino acid sequence of SEQ ID NO: 28;
5) a heavy chain that comprises an amino acid sequence which has at least 85% identity to the amino acid sequences of SEQ ID NO: 39, and a light chain that comprises an amino acid sequence which has at least 85% identity to the amino acid sequence of SEQ ID NO: 40;
6) a heavy chain that comprises an amino acid sequence which has at least 85% identity to the amino acid sequences of SEQ ID NO: 51, and a light chain that comprises an amino acid sequence which has at least 85% identity to the amino acid sequence of SEQ ID NO: 53;
7) a heavy chain that comprises an amino acid sequence which has at least 85% identity to the amino acid sequences of SEQ ID NO: 52, and a light chain that comprises an amino acid sequence which has at least 85% identity to the amino acid sequence of SEQ ID NO: 53;
8) a heavy chain that comprises an amino acid sequence which has at least 85% identity to the amino acid sequences of SEQ ID NO: 64, and a light chain that comprises an amino acid sequence which has at least 85% identity to the amino acid sequence of SEQ ID NO: 65;
9) a heavy chain that comprises an amino acid sequence which has at least 85% identity to the amino acid sequences of SEQ ID NO: 71, and a light chain that comprises an amino acid sequence which has at least 85% identity to the amino acid sequence of SEQ ID NO: 73;
10) a heavy chain that comprises an amino acid sequence which has at least 85% identity to the amino acid sequences of SEQ ID NO: 71, and a light chain that comprises an amino acid sequence which has at least 85% identity to the amino acid sequence of SEQ ID NO: 74;
11) a heavy chain that comprises an amino acid sequence which has at least 85% identity to the amino acid sequences of SEQ ID NO: 71, and a light chain that comprises an amino acid sequence which has at least 85% identity to the amino acid sequence of SEQ ID NO: 75;
12) a heavy chain that comprises an amino acid sequence which has at least 85% identity to the amino acid sequences of SEQ ID NO: 72, and a light chain that comprises an amino acid sequence which has at least 85% identity to the amino acid sequence of SEQ ID NO: 73;
13) a heavy chain that comprises an amino acid sequence which has at least 85% identity to the amino acid sequences of SEQ ID NO: 72, and a light chain that comprises an amino acid sequence which has at least 85% identity to the amino acid sequence of SEQ ID NO: 74;
14) a heavy chain that comprises an amino acid sequence which has at least 85% identity to the amino acid sequences of SEQ ID NO: 72, and a light chain that comprises an amino acid sequence which has at least 85% identity to the amino acid sequence of SEQ ID NO: 75;
15) a heavy chain that comprises an amino acid sequence which has at least 85% identity to the amino acid sequences of SEQ ID NO: 81, and a light chain that comprises an amino acid sequence which has at least 85% identity to the amino acid sequence of SEQ ID NO: 84;
16) a heavy chain that comprises an amino acid sequence which has at least 85% identity to the amino acid sequences of SEQ ID NO: 81, and a light chain that comprises an amino acid sequence which has at least 85% identity to the amino acid sequence of SEQ ID NO: 85;
17) a heavy chain that comprises an amino acid sequence which has at least 85% identity to the amino acid sequences of SEQ ID NO: 82, and a light chain that comprises an amino acid sequence which has at least 85% identity to the amino acid sequence of SEQ ID NO: 84;
18) a heavy chain that comprises an amino acid sequence which has at least 85% identity to the amino acid sequences of SEQ ID NO: 82, and a light chain that comprises an amino acid sequence which has at least 85% identity to the amino acid sequence of SEQ ID NO: 85;
19) a heavy chain that comprises an amino acid sequence which has at least 85% identity to the amino acid sequences of SEQ ID NO: 83, and a light chain that comprises an amino acid sequence which has at least 85% identity to the amino acid sequence of SEQ ID NO: 84;
20) a heavy chain that comprises an amino acid sequence which has at least 85% identity to the amino acid sequences of SEQ ID NO: 83, and a light chain that comprises an amino acid sequence which has at least 85% identity to the amino acid sequence of SEQ ID NO: 85;
21) a heavy chain that comprises an amino acid sequence which has at least 85% identity to the amino acid sequences of SEQ ID NO: 90, and a light chain that comprises an amino acid sequence which has at least 85% identity to the amino acid sequence of SEQ ID NO: 84;
22) a heavy chain that comprises an amino acid sequence which has at least 85% identity to the amino acid sequences of SEQ ID NO: 90, and a light chain that comprises an amino acid sequence which has at least 85% identity to the amino acid sequence of SEQ ID NO: 85;
23) a heavy chain that comprises an amino acid sequence which has at least 85% identity to the amino acid sequences of SEQ ID NO: 91, and a light chain that comprises an amino acid sequence which has at least 85% identity to the amino acid sequence of SEQ ID NO: 84;
24) a heavy chain that comprises an amino acid sequence which has at least 85% identity to the amino acid sequences of SEQ ID NO: 91, and a light chain that comprises an amino acid sequence which has at least 85% identity to the amino acid sequence of SEQ ID NO: 85;
25) a heavy chain that comprises an amino acid sequence which has at least 85% identity to the amino acid sequences of SEQ ID NO: 86, and a light chain that comprises an amino acid sequence which has at least 85% identity to the amino acid sequence of SEQ ID NO: 88;
26) a heavy chain that comprises an amino acid sequence which has at least 85% identity to the amino acid sequences of SEQ ID NO: 86, and a light chain that comprises an amino acid sequence which has at least 85% identity to the amino acid sequence of SEQ ID NO: 89;
27) a heavy chain that comprises an amino acid sequence which has at least 85% identity to the amino acid sequences of SEQ ID NO: 87, and a light chain that comprises an amino acid sequence which has at least 85% identity to the amino acid sequence of SEQ ID NO: 88;
28) a heavy chain that comprises an amino acid sequence which has at least 85% identity to the amino acid sequences of SEQ ID NO: 87, and a light chain that comprises an amino acid sequence which has at least 85% identity to the amino acid sequence of SEQ ID NO: 89;
29) a heavy chain that comprises an amino acid sequence which has at least 85% identity to the amino acid sequences of SEQ ID NO: 124, and a light chain that comprises an amino acid sequence which has at least 85% identity to the amino acid sequence of SEQ ID NO: 84;
30) a heavy chain that comprises an amino acid sequence which has at least 85% identity to the amino acid sequences of SEQ ID NO: 124, and a light chain that comprises an amino acid sequence which has at least 85% identity to the amino acid sequence of SEQ ID NO: 85;
31) a heavy chain that comprises an amino acid sequence which has at least 85% identity to the amino acid sequences of SEQ ID NO: 125, and a light chain that comprises an amino acid sequence which has at least 85% identity to the amino acid sequence of SEQ ID NO: 84; or
32) a heavy chain that comprises an amino acid sequence which has at least 85% identity to the amino acid sequences of SEQ ID NO: 125, and a light chain that comprises an amino acid sequence which has at least 85% identity to the amino acid sequence of SEQ ID NO: 85.

In some embodiments, the heavy and light chain comprise an amino acid sequence at least 90%, at least 95%, at least 96%, at least 97%, at least 98%, at least 99%, or 100% identity to the heavy and light chain variable regions, respectively, selected from the group consisting of 1)-32).

In another respect, the invention provides an isolated antibody or antigen-binding fragment thereof, which comprises a heavy chain of SEQ ID NO: 71 and a light chain of SEQ ID NO: 73.

In yet another respect, the invention provides an isolated antibody or antigen-binding fragment thereof, which comprises a heavy chain consisting essentially of SEQ ID NO: 72 and a light chain consisting essentially of SEQ ID NO: 74.

In one respect, the invention provides an isolated antibody or antigen-binding fragment thereof, which comprises a heavy chain of SEQ ID NO: 72 and a light chain of SEQ ID NO: 75.

In another respect, the invention provides an isolated antibody or antigen-binding fragment thereof, which comprises a heavy chain consisting essentially of SEQ ID NO: 81 and a light chain consisting essentially of SEQ ID NO: 85.

In yet another respect, the invention provides an isolated antibody or antigen-binding fragment thereof, which comprises a heavy chain consisting essentially of SEQ ID NO: 82 and a light chain consisting essentially of SEQ ID NO: 84.

In one respect, the invention provides an isolated antibody or antigen-binding fragment thereof, which comprises a heavy chain consisting essentially of SEQ ID NO: 83 and a light chain consisting essentially of SEQ ID NO: 85.

In another respect, the invention provides an isolated antibody or antigen-binding fragment thereof, which comprises a heavy chain consisting essentially of SEQ ID NO: 124 and a light chain consisting essentially of SEQ ID NO: 85.

In yet another respect, the invention provides an isolated antibody or antigen-binding fragment thereof, which comprises a heavy chain consisting essentially of SEQ ID NO: 125 and a light chain consisting essentially of SEQ ID NO: 85.

In some embodiments, the isolated antibody or antigen-binding fragment thereof is an antagonist of CD73 or 5'-nucleotidase of CD73.

In some embodiments, the CD73 is human CD73.

In one respect, the invention provides a method of decreasing adenosine levels in a subject with tumor, comprising administering a therapeutically effective amount of the isolated antibody or antigen-binding fragment thereof.

In another respect, the invention provides a method of improving a T cell response in a subject with tumor, comprising administering a therapeutically effective amount of the isolated antibody or antigen-binding fragment thereof.

In yet another respect, the invention provides a method of stimulating an immune response in a subject comprising administering a therapeutically effective amount of the isolated antibody or antigen-binding fragment thereof.

In some embodiments, the subject is the subject with tumor.

In some embodiments, the subject has a tumor cell expressing CD73 and/or a tumor microenvironment containing CD73.

In one respect, the invention provides a method for inhibiting the growth of tumor cells in a subject comprising administering to the subject a therapeutically effective amount of the isolated antibody or antigen-binding fragment thereof.

In another respect, the invention provides use of the isolated antibody or antigen-binding fragment thereof in the manufacture of a medicament for decreasing adenosine levels in a tumor cell and/or a tumor microenvironment.

In yet another respect, the invention provides use of the isolated antibody or antigen-binding fragment thereof in the manufacture of a medicament for stimulating a T cell response in a subject with tumor.

In one respect, the invention provides use of the isolated antibody or antigen-binding fragment thereof in the manufacture of a medicament for stimulating an immune response in a subject.

In some embodiments, the subject is a subject with tumor.

In some embodiments, the subject has a tumor cell expressing CD73 and/or a tumor microenvironment containing CD73.

In another respect, the invention provides use of the isolated antibody or antigen-binding fragment thereof in the manufacture of a medicament for inhibiting the growth of tumor cells in a subject.

In yet another respect, the invention provides the isolated antibody or antigen-binding fragment thereof for use in decreasing adenosine levels in a tumor cell and/or a tumor microenvironment.

In one respect, the invention provides the isolated antibody or antigen-binding fragment thereof for use in stimulating a T cell response in a subject with tumor.

In another respect, the invention provides the isolated antibody or antigen-binding fragment thereof for use in stimulating an immune response in a subject.

In some embodiments, the subject is a subject with tumor.

In some embodiments, the subject has a tumor cell expressing CD73 and/or a tumor microenvironment containing CD73.

In another respect, the invention provides the isolated antibody or antigen-binding fragment thereof for use in inhibiting the growth of tumor cells in a subject.

In yet another respect, the invention provides an isolated nucleic acid composition, which comprises:
 (I) a first nucleic acid comprising a nucleotide sequence selected from the group consisting of SEQ ID NOs: 4, 17, 30, 42, 55, 92, 93, 102, 103 and 104; and
 (II) a second nucleic acid comprising a nucleotide sequence selected from the group consisting of SEQ ID NOs: 9, 22, 35, 47, 60, 94, 95, 96, 105 and 106.

In some embodiments, the isolated nucleic acid composition comprises:
 1) the first nucleic acid comprising SEQ ID NO: 4 and the second nucleic acid comprising SEQ ID NO: 9;
 2) the first nucleic acid comprising SEQ ID NO: 17 and the second nucleic acid comprising SEQ ID NO: 22;
 3) the first nucleic acid comprising SEQ ID NO: 30 and the second nucleic acid comprising SEQ ID NO: 35;
 4) the first nucleic acid comprising SEQ ID NO: 42 and the second nucleic acid comprising SEQ ID NO: 47;
 5) the first nucleic acid comprising SEQ ID NO: 55 and the second nucleic acid comprising SEQ ID NO: 60;
 6) the first nucleic acid comprising SEQ ID NO: 92 and the second nucleic acid comprising SEQ ID NO: 94;
 7) the first nucleic acid comprising SEQ ID NO: 92 and the second nucleic acid comprising SEQ ID NO: 95;
 8) the first nucleic acid comprising SEQ ID NO: 92 and the second nucleic acid comprising SEQ ID NO: 96;
 9) the first nucleic acid comprising SEQ ID NO: 93 and the second nucleic acid comprising SEQ ID NO: 94;
 10) the first nucleic acid comprising SEQ ID NO: 93 and the second nucleic acid comprising SEQ ID NO: 95;
 11) the first nucleic acid comprising SEQ ID NO: 93 and the second nucleic acid comprising SEQ ID NO: 96;
 12) the first nucleic acid comprising SEQ ID NO: 102 and the second nucleic acid comprising SEQ ID NO: 105;
 13) the first nucleic acid comprising SEQ ID NO: 102 and the second nucleic acid comprising SEQ ID NO: 106;
 14) the first nucleic acid comprising SEQ ID NO: 103 and the second nucleic acid comprising SEQ ID NO: 105;
 15) the first nucleic acid comprising SEQ ID NO: 103 and the second nucleic acid comprising SEQ ID NO: 106;
 16) the first nucleic acid comprising SEQ ID NO: 104 and the second nucleic acid comprising SEQ ID NO: 105; or 17) the first nucleic acid comprising SEQ ID NO: 104 and the second nucleic acid comprising SEQ ID NO: 106.

In one respect, the invention provides an expression vector composition, which comprises:
(I) a first expression vector comprising a nucleotide sequence selected from the group consisting of SEQ ID NOs: 4, 17, 30, 42, 55, 92, 93, 102, 103 and 104; and
(II) a second expression vector comprising a nucleotide sequences selected from the group consisting of SEQ ID NOs: 9, 22, 35, 47, 60, 94, 95, 96, 105 and 106.

In some embodiments, the expression vector composition comprises:
1) a first expression vector comprising a nucleotide sequence of SEQ ID NO: 4 and a second expression vector comprising a nucleotide sequence of SEQ ID NO: 9;
2) a first expression vector comprising a nucleotide sequence of SEQ ID NO: 17 and a second expression vector comprising a nucleotide sequence of SEQ ID NO: 22;
3) a first expression vector comprising a nucleotide sequence of SEQ ID NO: 30 and a second expression vector comprising a nucleotide sequence of SEQ ID NO: 35;
4) a first expression vector comprising a nucleotide sequence of SEQ ID NO: 42 and a second expression vector comprising a nucleotide sequence of SEQ ID NO: 47;
5) a first expression vector comprising a nucleotide sequence of SEQ ID NO: 55 and a second expression vector comprising a nucleotide sequence of SEQ ID NO: 60;
6) a first expression vector comprising a nucleotide sequence of SEQ ID NO: 92 and a second expression vector comprising a nucleotide sequence of SEQ ID NO: 94;
7) a first expression vector comprising a nucleotide sequence of SEQ ID NO: 92 and a second expression vector comprising a nucleotide sequence of SEQ ID NO: 95;
8) a first expression vector comprising a nucleotide sequence of SEQ ID NO: 92 and a second expression vector comprising a nucleotide sequence of SEQ ID NO: 96;
9) a first expression vector comprising a nucleotide sequence of SEQ ID NO: 93 and a second expression vector comprising a nucleotide sequence of SEQ ID NO: 94;
10) a first expression vector comprising a nucleotide sequence of SEQ ID NO: 93 and a second expression vector comprising a nucleotide sequence of SEQ ID NO: 95;
11) a first expression vector comprising a nucleotide sequence of SEQ ID NO: 93 and a second expression vector comprising a nucleotide sequence of SEQ ID NO: 96;
12) a first expression vector comprising a nucleotide sequence of SEQ ID NO: 102 and a second expression vector comprising a nucleotide sequence of SEQ ID NO: 105;
13) a first expression vector comprising a nucleotide sequence of SEQ ID NO: 102 and a second expression vector comprising a nucleotide sequence of SEQ ID NO: 106;
14) a first expression vector comprising a nucleotide sequence of SEQ ID NO: 103 and a second expression vector comprising a nucleotide sequence of SEQ ID NO: 105;
15) a first expression vector comprising a nucleotide sequence of SEQ ID NO: 103 and a second expression vector comprising a nucleotide sequence of SEQ ID NO: 106;
16) a first expression vector comprising a nucleotide sequence of SEQ ID NO: 104 and a second expression vector comprising a nucleotide sequence of SEQ ID NO: 105; or
17) a first expression vector comprising a nucleotide sequence of SEQ ID NO: 104 and a second expression vector comprising a nucleotide sequence of SEQ ID NO: 106.

In another respect, the invention provides an expression vector, which comprises:
(I) a first nucleic acid sequence comprising a nucleotide sequence selected from the group consisting of SEQ ID NOs: 4, 17, 30, 42, 55, 92, 93, 102, 103 and 104; and
(II) a second nucleic acid sequence comprising a nucleotide sequence selected from the group consisting of SEQ ID NOs: 9, 22, 35, 47, 60, 94, 95, 96, 105 and 106.

In some embodiments, the expression vector, comprises:
1) a first nucleic acid sequence comprising a nucleotide sequence of SEQ ID NO: 4 and a second nucleic acid sequence comprising a nucleotide sequence of SEQ ID NO: 9;
2) a first nucleic acid sequence comprising a nucleotide sequence of SEQ ID NO: 17 and a second nucleic acid sequence comprising a nucleotide sequence of SEQ ID NO: 22;
3) a first nucleic acid sequence comprising a nucleotide sequence of SEQ ID NO: 30 and a second nucleic acid sequence comprising a nucleotide sequence of SEQ ID NO: 35;
4) a first nucleic acid sequence comprising a nucleotide sequence of SEQ ID NO: 42 and a second nucleic acid sequence comprising a nucleotide sequence of SEQ ID NO: 47;
5) a first nucleic acid sequence comprising a nucleotide sequence of SEQ ID NO: 55 and a second nucleic acid sequence comprising a nucleotide sequence of SEQ ID NO: 60;
6) a first nucleic acid sequence comprising a nucleotide sequence of SEQ ID NO: 92 and a second nucleic acid sequence comprising a nucleotide sequence of SEQ ID NO: 94;
7) a first nucleic acid sequence comprising a nucleotide sequence of SEQ ID NO: 92 and a second nucleic acid sequence comprising a nucleotide sequence of SEQ ID NO: 95;
8) a first nucleic acid sequence comprising a nucleotide sequence of SEQ ID NO: 92 and a second nucleic acid sequence comprising a nucleotide sequence of SEQ ID NO: 96;
9) a first nucleic acid sequence comprising a nucleotide sequence of SEQ ID NO: 93 and a second nucleic acid sequence comprising a nucleotide sequence of SEQ ID NO: 94;
10) a first nucleic acid sequence comprising a nucleotide sequence of SEQ ID NO: 93 and a second nucleic acid sequence comprising a nucleotide sequence of SEQ ID NO: 95;

11) a first nucleic acid sequence comprising a nucleotide sequence of SEQ ID NO: 93 and a second nucleic acid sequence comprising a nucleotide sequence of SEQ ID NO: 96;
12) a first nucleic acid sequence comprising a nucleotide sequence of SEQ ID NO: 102 and a second nucleic acid sequence comprising a nucleotide sequence of SEQ ID NO: 105;
13) a first nucleic acid sequence comprising a nucleotide sequence of SEQ ID NO: 102 and a second nucleic acid sequence comprising a nucleotide sequence of SEQ ID NO: 106;
14) a first nucleic acid sequence comprising a nucleotide sequence of SEQ ID NO: 103 and a second nucleic acid sequence comprising a nucleotide sequence of SEQ ID NO: 105;
15) a first nucleic acid sequence comprising a nucleotide sequence of SEQ ID NO: 103 and a second nucleic acid sequence comprising a nucleotide sequence of SEQ ID NO: 106;
16) a first nucleic acid sequence comprising a nucleotide sequence of SEQ ID NO: 104 and a second nucleic acid sequence comprising a nucleotide sequence of SEQ ID NO: 105;
17) a first nucleic acid sequence comprising a nucleotide sequence of SEQ ID NO: 104 and a second nucleic acid sequence comprising a nucleotide sequence of SEQ ID NO: 106.

In yet another respect, the invention provides an isolated nucleic acid composition, which comprises:
(I) a first nucleic acid comprising a nucleotide sequence selected from the group consisting of SEQ ID NOs: 97, 98, 107, 108, 109, 112, 113, 116 and 117; and
(II) a second nucleic acid comprising a nucleotide sequence selected from the group consisting of SEQ ID NOs: 99, 100, 101, 110, 111, 114 and 115.

In some embodiments, the isolated nucleic acid composition, comprises:
1) the first nucleic acid comprising SEQ ID NO: 97 and the second nucleic acid comprising SEQ ID NO: 99;
2) the first nucleic acid comprising SEQ ID NO: 97 and the second nucleic acid comprising SEQ ID NO: 100;
3) the first nucleic acid comprising SEQ ID NO: 97 and the second nucleic acid comprising SEQ ID NO: 101;
4) the first nucleic acid comprising SEQ ID NO: 98 and the second nucleic acid comprising SEQ ID NO: 99;
5) the first nucleic acid comprising SEQ ID NO: 98 and the second nucleic acid comprising SEQ ID NO: 100;
6) the first nucleic acid comprising SEQ ID NO: 98 and the second nucleic acid comprising SEQ ID NO: 101;
7) the first nucleic acid comprising SEQ ID NO: 107 and the second nucleic acid comprising SEQ ID NO: 110;
8) the first nucleic acid comprising SEQ ID NO: 107 and the second nucleic acid comprising SEQ ID NO: 111;
9) the first nucleic acid comprising SEQ ID NO: 108 and the second nucleic acid comprising SEQ ID NO: 110;
10) the first nucleic acid comprising SEQ ID NO: 108 and the second nucleic acid comprising SEQ ID NO: 111;
11) the first nucleic acid comprising SEQ ID NO: 109 and the second nucleic acid comprising SEQ ID NO: 110;
12) the first nucleic acid comprising SEQ ID NO: 109 and the second nucleic acid comprising SEQ ID NO: 111;
13) the first nucleic acid comprising SEQ ID NO: 116 and the second nucleic acid comprising SEQ ID NO: 110;
14) the first nucleic acid comprising SEQ ID NO: 116 and the second nucleic acid comprising SEQ ID NO: 111;
15) the first nucleic acid comprising SEQ ID NO: 117 and the second nucleic acid comprising SEQ ID NO: 110;
16) the first nucleic acid comprising SEQ ID NO: 117 and the second nucleic acid comprising SEQ ID NO: 111;
17) the first nucleic acid comprising SEQ ID NO: 112 and the second nucleic acid comprising SEQ ID NO: 114;
18) the first nucleic acid comprising SEQ ID NO: 112 and the second nucleic acid comprising SEQ ID NO: 115;
19) the first nucleic acid comprising SEQ ID NO: 113 and the second nucleic acid comprising SEQ ID NO: 114; or
20) the first nucleic acid comprising SEQ ID NO: 113 and the second nucleic acid comprising SEQ ID NO: 115.

In one respect, the invention provides an expression vector composition, which comprises:
(I) a first expression vector comprising a nucleotide sequence selected from the group consisting of SEQ ID NOs: 97, 98, 107, 108, 109, 112, 113, 116 and 117; and
(II) a second expression vector comprising a nucleotide sequences selected from the group consisting of SEQ ID NOs: 99, 100, 101, 110, 111, 114 and 115.

In some embodiments, the invention provides the expression vector composition, which comprises:
1) a first expression vector comprising a nucleotide sequence of SEQ ID NO: 97 and a second expression vector comprising a nucleotide sequence of SEQ ID NO: 99;
2) a first expression vector comprising a nucleotide sequence of SEQ ID NO: 97 and a second expression vector comprising a nucleotide sequence of SEQ ID NO: 100;
3) a first expression vector comprising a nucleotide sequence of SEQ ID NO: 97 and a second expression vector comprising a nucleotide sequence of SEQ ID NO: 101;
4) a first expression vector comprising a nucleotide sequence of SEQ ID NO: 98 and a second expression vector comprising a nucleotide sequence of SEQ ID NO: 99;
5) a first expression vector comprising a nucleotide sequence of SEQ ID NO: 98 and a second expression vector comprising a nucleotide sequence of SEQ ID NO: 100;
6) a first expression vector comprising a nucleotide sequence of SEQ ID NO: 98 and a second expression vector comprising a nucleotide sequence of SEQ ID NO: 101;
7) a first expression vector comprising a nucleotide sequence of SEQ ID NO: 107 and a second expression vector comprising a nucleotide sequence of SEQ ID NO: 110;
8) a first expression vector comprising a nucleotide sequence of SEQ ID NO: 107 and a second expression vector comprising a nucleotide sequence of SEQ ID NO: 111;
9) a first expression vector comprising a nucleotide sequence of SEQ ID NO: 108 and a second expression vector comprising a nucleotide sequence of SEQ ID NO: 110;
10) a first expression vector comprising a nucleotide sequence of SEQ ID NO: 108 and a second expression vector comprising a nucleotide sequence of SEQ ID NO: 111;
11) a first expression vector comprising a nucleotide sequence of SEQ ID NO: 109 and a second expression vector comprising a nucleotide sequence of SEQ ID NO: 110;

12) a first expression vector comprising a nucleotide sequence of SEQ ID NO: 109 and a second expression vector comprising a nucleotide sequence of SEQ ID NO: 111;
13) a first expression vector comprising a nucleotide sequence of SEQ ID NO: 116 and a second expression vector comprising a nucleotide sequence of SEQ ID NO: 110;
14) a first expression vector comprising a nucleotide sequence of SEQ ID NO: 116 and a second expression vector comprising a nucleotide sequence of SEQ ID NO: 111;
15) a first expression vector comprising a nucleotide sequence of SEQ ID NO: 117 and a second expression vector comprising a nucleotide sequence of SEQ ID NO: 110;
16) a first expression vector comprising a nucleotide sequence of SEQ ID NO: 117 and a second expression vector comprising a nucleotide sequence of SEQ ID NO: 111;
17) a first expression vector comprising a nucleotide sequence of SEQ ID NO: 112 and a second expression vector comprising a nucleotide sequence of SEQ ID NO: 114;
18) a first expression vector comprising a nucleotide sequence of SEQ ID NO: 112 and a second expression vector comprising a nucleotide sequence of SEQ ID NO: 115;
19) a first expression vector comprising a nucleotide sequence of SEQ ID NO: 113 and a second expression vector comprising a nucleotide sequence of SEQ ID NO: 114; or
20) a first expression vector comprising a nucleotide sequence of SEQ ID NO: 113 and a second expression vector comprising a nucleotide sequence of SEQ ID NO: 115.

In another respect, the invention provides an expression vector, which comprises:
(I) a first nucleic acid sequence comprising a nucleotide sequence selected from the group consisting of SEQ ID NOs: 97, 98, 107, 108, 109, 112, 113, 116 and 117; and
(II) a second nucleic acid sequence comprising a nucleotide sequence selected from the group consisting of SEQ ID NOs: 99, 100, 101, 110, 111, 114 and 115.

In some embodiments, the expression vector, comprises:
1) a first nucleic acid sequence comprising a nucleotide sequence of SEQ ID NO: 97 and a second nucleic acid sequence comprising a nucleotide sequence of SEQ ID NO: 99;
2) a first nucleic acid sequence comprising a nucleotide sequence of SEQ ID NO: 97 and a second nucleic acid sequence comprising a nucleotide sequence of SEQ ID NO: 100;
3) a first nucleic acid sequence comprising a nucleotide sequence of SEQ ID NO: 97 and a second nucleic acid sequence comprising a nucleotide sequence of SEQ ID NO: 101;
4) a first nucleic acid sequence comprising a nucleotide sequence of SEQ ID NO: 98 and a second nucleic acid sequence comprising a nucleotide sequence of SEQ ID NO: 99;
5) a first nucleic acid sequence comprising a nucleotide sequence of SEQ ID NO: 98 and a second nucleic acid sequence comprising a nucleotide sequence of SEQ ID NO: 100;
6) a first nucleic acid sequence comprising a nucleotide sequence of SEQ ID NO: 98 and a second nucleic acid sequence comprising a nucleotide sequence of SEQ ID NO: 101;
7) a first nucleic acid sequence comprising a nucleotide sequence of SEQ ID NO: 107 and a second nucleic acid sequence comprising a nucleotide sequence of SEQ ID NO: 110;
8) a first nucleic acid sequence comprising a nucleotide sequence of SEQ ID NO: 107 and a second nucleic acid sequence comprising a nucleotide sequence of SEQ ID NO: 111;
9) a first nucleic acid sequence comprising a nucleotide sequence of SEQ ID NO: 108 and a second nucleic acid sequence comprising a nucleotide sequence of SEQ ID NO: 110;
10) a first nucleic acid sequence comprising a nucleotide sequence of SEQ ID NO: 108 and a second nucleic acid sequence comprising a nucleotide sequence of SEQ ID NO: 111;
11) a first nucleic acid sequence comprising a nucleotide sequence of SEQ ID NO: 109 and a second nucleic acid sequence comprising a nucleotide sequence of SEQ ID NO: 110;
12) a first nucleic acid sequence comprising a nucleotide sequence of SEQ ID NO: 109 and a second nucleic acid sequence comprising a nucleotide sequence of SEQ ID NO: 111;
13) a first nucleic acid sequence comprising a nucleotide sequence of SEQ ID NO: 116 and a second nucleic acid sequence comprising a nucleotide sequence of SEQ ID NO: 110;
14) a first nucleic acid sequence comprising a nucleotide sequence of SEQ ID NO: 116 and a second nucleic acid sequence comprising a nucleotide sequence of SEQ ID NO: 111;
15) a first nucleic acid sequence comprising a nucleotide sequence of SEQ ID NO: 117 and a second nucleic acid sequence comprising a nucleotide sequence of SEQ ID NO: 110;
16) a first nucleic acid sequence comprising a nucleotide sequence of SEQ ID NO: 117 and a second nucleic acid sequence comprising a nucleotide sequence of SEQ ID NO: 111;
17) a first nucleic acid sequence comprising a nucleotide sequence of SEQ ID NO: 112 and a second nucleic acid sequence comprising a nucleotide sequence of SEQ ID NO: 114;
18) a first nucleic acid sequence comprising a nucleotide sequence of SEQ ID NO: 112 and a second nucleic acid sequence comprising a nucleotide sequence of SEQ ID NO: 115;
19) a first nucleic acid sequence comprising a nucleotide sequence of SEQ ID NO: 113 and a second nucleic acid sequence comprising a nucleotide sequence of SEQ ID NO: 114; or
20) a first nucleic acid sequence comprising a nucleotide sequence of SEQ ID NO: 113 and a second nucleic acid sequence comprising a nucleotide sequence of SEQ ID NO: 115.

In yet another respect, the invention provides a cell comprising any one of the expression vector composition.

In one respect, the invention provides a method of preparing the isolated antibody or antigen-binding fragment thereof, comprising expressing the isolated antibody or antigen-bind thereof in the cell, and isolating the isolated antibody or antigen-binding fragment from the cell.

In another respect, the invention provides a pharmaceutical composition comprising the isolated antibody or antigen-binding fragment thereof, and a pharmaceutically acceptable excipient.

In yet another respect, the invention provides a kit comprising the isolated antibody or antigen-binding fragment thereof.

In one respect, the invention provides a method of treating tumor comprising administering a subject in need a therapeutically effective amount of the isolated antibody or antigen-binding fragment thereof, or the pharmaceutical composition. In some embodiments, the tumor is selected from solid tumor or hematological tumor. In some embodiments, the tumor is selected from bladder cancer, breast cancer, cervical cancer, ovarian cancer, prostate cancer, testicular cancer, esophageal cancer, gastrointestinal cancer, pancreatic cancer, colorectal cancer, colon cancer, renal cancer, head and neck cancer, lung cancer (small cell lung cancer or non-small cell lung cancer), stomach cancer, bone cancer, liver cancer, thyroid cancer, skin cancer, central nervous system tumor, lymphoma, leukemia, myeloma, sarcoma, and virus-associated cancer.

In another respect, the invention provides use of the isolated antibody or antigen-binding fragment thereof, or the pharmaceutical composition for the manufacture of a medicament for a treatment of tumor. In some embodiments, the tumor is selected from solid tumor or hematological tumor. In some embodiments, the tumor is selected from bladder cancer, breast cancer, cervical cancer, ovarian cancer, prostate cancer, testicular cancer, esophageal cancer, gastrointestinal cancer, pancreatic cancer, colorectal cancer, colon cancer, renal cancer, head and neck cancer, lung cancer (small cell lung cancer or non-small cell lung cancer), stomach cancer, bone cancer, liver cancer, thyroid cancer, skin cancer, central nervous system tumor, lymphoma, leukemia, myeloma, sarcoma, and virus-associated cancer.

In yet another respect, the invention provides the isolated antibody or antigen-binding fragment thereof, or the pharmaceutical composition for use in a treatment of tumor. In some embodiments, the tumor is selected from solid tumor or hematological tumor. In some embodiments, the cancer is selected from bladder cancer, breast cancer, cervical cancer, ovarian cancer, prostate cancer, testicular cancer, esophageal cancer, gastrointestinal cancer, pancreatic cancer, colorectal cancer, colon cancer, renal cancer, head and neck cancer, lung cancer (small cell lung cancer or non-small cell lung cancer), stomach cancer, bone cancer, liver cancer, thyroid cancer, skin cancer, central nervous system tumor, lymphoma, leukemia, myeloma, sarcoma, and virus-associated cancer.

TABLE I

Description of the antibody sequence listing of the invention

| SEQ ID NO: | Sequence Description | Sequence |
|---|---|---|
| 1 | huCD73 | WELTILHTNDVHSRLEQTSEDSSKCVNASRCMGG VARLFTKVQQIRRAEPNVLLLDAGDQYQGTIWFT VYKGAEVAHFMNALRYDAMALGNHEFDNGVEGLI EPLLKEAKFPILSANIKAKGPLASQISGLYLPYK VLPVGDEVVGIVGYTSKETPFLSNPGTNLVFEDE ITALQPEVDKLKTLNVNKIIALGHSGFEMDKLIA QKVRGVDVVVGGHSNTFLYTGNPPSKEVPAGKYP FIVTSDDGRKVPVVQAYAFGKYLGYLKIEFDERG NVISSHGNPILLNSSIPEDPSIKADINKWRIKLD NYSTQELGKTIVYLDGSSQSCRFRECNMGNLICD AMINNNLRHTDEMFWNHVSMCILNGGGIRSPIDE RNNGTITWENLAAVLPFGGTFDLVQLKGSTLKKA FEHSVHRYGQSTGEFLQVGGIHVVYDLSRKPGDR VVKLDVLCTKCRVPSYDPLKMDEVYKVILPNFLA NGGDGFQMIKDELLRHDSGDQDINVVSTYISKMK VIYPAVEGRIKAHHHHHHHHHH |
| 2 | cynoCD73 | WELTILHTNDVHSRLEQTSEDSSKCVNASRCMGG VARLFTKVQQIRRAEPNVLLLDAGDQYQGTIWFT VYKGAEVAHFMNALRYDAMALGNHEFDNGVEGLI EPLLKEAKFPILSANIKAKGPLASQISGLYLPYK VLPVGDEVVGIVGYTSKETPFLSNPGTNLVFEDE ITALQPEVDKLKTLNVNKIIALGHSGFETDKLIA QKVRGVDVVVGGHSNTFLYTGNPPSKEVPAGKYP FIVTSDDGRKVPVVQAYAFGKYLGYLKIEFDERG NVISSHGNPILLNSSIPEDPSIKADINKWRIKLD NYSTQELGKTIVYLDGSSQSCRFRECNMGNLICD AMINNNLRHADEMFWNHVSMCILNGGGIRSPIDE RNNGTITWENLAAVLPFGGTFDLVQLKGSTLKKA FEHSVHRYGQSTGEFLQVGGIHVVYDLSRKPGDR VVKLDVLCTKCRVPSYDPLKMDEIYKVILPNFLA NGGDGFQMIKDELLRHDSGDQDINVVSTYISKMK VIYPAVEGRIKAHHHHHHHHHH |
| 3 | S1B5 VH aa | EVQLKESGAELVKPGASVKISCKATGYTFTGYWI EWVKQRPGRGLEWIGEILPGSDITNYNEKFKGKA TITADTSSNTAYMQLSSLTTEDSAIYYCARRGYD ETGYAMDYWGQGTSVTVSS |
| 4 | S1B5 VH nt | GAGGTGCAGCTGAAGGAGTCTGGGGCTGAGCT GGTGAAGCCTGGGGCCTCAGTGAAGATTTCCTG CAAAGCTACTGGCTATACATTCACTGGCTACTG GATAGAGTGGGTAAAGCAGAGGCCTGGACGTG GCCTTGAGTGGATTGGAGAGATTTTACCTGGAA GTGATATTACTAACTACAATGAGAAGTTCAAGG GCAAGGCCACAATCACTGCAGATACATCCTCCA ACACAGCCTACATGCAACTCAGCAGCCTGACAA CTGAGGACTCTGCCATCTATTACTGTGCAAGAA GGGGTTACGACGAGACGGGCTATGCTATGGACT ACTGGGGTCAAGGAACCTCAGTCACAGTCTCCT CA |
| 5 | S1B5 VH CDR1 | GYWIE |
| 6 | S1B5 VH CDR2 | EILPGSDITNYNEKFKG |
| 7 | S1B5 VH CDR3 | RGYDETGYAMDY |
| 8 | S1B5 VL aa | DIVMTQSPASLAVSLGQRATISCKASQSVDYDGD SYMNWYQQKPGQPPKLLIHAASNLESGIPARFSG SGSGTDFTLNIHPVEEEDAAVYFCQQSKEVPWTF GEGTKLEIK |
| 9 | S1B5 VL nt | GACATTGTGATGACCCAATCTCCAGCTTCTTTG GCTGTGTCTCTAGGGCAGAGGGCCACCATCTCC TGCAAGGCCAGCCAAAGTGTTGATTATGATGGT GATAGCTATATGAACTGGTACCAACAGAAACC AGGACAGCCACCCAAACTCCTCATCCATGCTGC ATCCAATCTAGAATCTGGGATCCCAGCCAGGTT TAGTGGCAGTGGGTCTGGGACAGACTTCACCCT CAACATCCATCCTGTGGAGGAAGAGGATGCTGC AGTGTATTTCTGTCAGCAAAGTAAGGAGGTTCC GTGGACGTTCGTGGAAGGGACCAAGCTGGAAA TCAAA |
| 10 | S1B5 VL CDR1 | KASQSVDYDGDSYMN |

TABLE I-continued

Description of the antibody sequence listing of the invention

| SEQ ID NO: | Sequence Description | Sequence |
|---|---|---|
| 11 | S1B5 VL CDR2 | AASNLES |
| 12 | S1B5 VL CDR3 | QQSKEVPWT |
| 13 | S1B5 hIgG1 full heavy chain | EVQLKESGAELVKPGASVKISCKATGYTFTGYWI EWVKQRPGRGLEWIGEILPGSDITNYNEKFKGKA TITADTSSNTAYMQLSSLTTEDSAIYYCARRGYD ETGYAMDYWGQGTSVTVSSASTKGPSVFPLAPSS KSTSGGTAALGCLVKDYFPEPVTVSWNSGALTSG VHTFPAVLQSSGLYSLSSVVTVPSSSLGTQTYIC NVNHKPSNTKVDKKVEPKSCDKTHTCPPCPAPEL LGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALPAPIEKTI SKAKGQPREPQVYTLPPSRDELTKNQVSLTCLVK GFYPSDIAVEWESNGQPENNYKTTPPVLDSDGSF FLYSKLTVDKSRWQQGNVFSCSVMHEALHNHYTQ KSLSLSPGK |
| 14 | S1B5 hkappa full light chain | DIVMTQSPASLAVSLGQRATISCKASQSVDYDGD SYMNWYQQKPGQPPKLLIHAASNLESGIPARFSG SGSGTDFTLNIHPVEEEDAAVYFCQQSKEVPWTF GEGTKLEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| 15 | S1B5 hIgG2 full heavy chain | EVQLKESGAELVKPGASVKISCKATGYTFTGYWI EWVKQRPGRGLEWIGEILPGSDITNYNEKFKGKA TITADTSSNTAYMQLSSLTTEDSAIYYCARRGYD ETGYAMDYWGQGTSVTVSSASTKGPSVFPLAPCS RSTSESTAALGCLVKDYFPEPVTVSWNSGALTSG VHTFPAVLQSSGLYSLSSVVTVPSSNFGTQTYTC NVDHKPSNTKVDKTVERKCCVECPPCPAPPVAGP SVFLFPPKPKDTLMISRTPEVTCVVVDVSHEDPE VQFNWYVDGVEVHNAKTKPREEQFNSTFRVVSVL TVVHQDWLNGKEYKCKVSNKGLPAPIEKTISKTK GQPREPQVYTLPPSREEMTKNQVSLTCLVKGFYP SDIAVEWESNGQPENNYKTTPPMLDSDGSFFLYS KLTVDKSRWQQGNVFSCSVMHEALHNHYTQKSLS LSPGK |
| 16 | JB24Chi VH aa | QVQLQQSGLELVKPGASVKMSCKASGYTFTDYN MHWVKQSHGKSLEWIGYIKPHNGGTTYNPKFEG KATLTVNKSSSTAYMELRSLTSEDSAVYYCVRC DFLYWYFDVWGTGTTVTVSS |
| 17 | JB24Chi VH nt | CAGGTCCAACTGCAGCAGTCTGGACTTGAGCTG GTGAAGCCTGGGGCTTCAGTGAAGATGTCCTGC AAGGCTTCTGGATACACATTCACTGACTACAAC ATGCACTGGGTGAAGCAGAGCCATGGAAAGAGC CTTGAGTGGATTGGATATATTAAGCCTCACAAT GGTGGTACTACCTACAACCCGAAGTTCGAGGGC AAGGCCACATTGACTGTAAACAAGTCTTCCAGC ACAGCCTACATGGAGCTCCGCAGCCTGACATCG GAGGATTCTGCAGTCTATTACTGTGTAAGATGC GATTTTCTCTACTGGTATTTCGATGTCTGGGGC ACAGGGACCACGGTCACCGTCTCCTCA |
| 18 | JB24Chi VH CDR1 | DYNMH |
| 19 | JB24Chi VH CDR2 | YIKPHNGGTTYNPKFEG |
| 20 | JB24Chi VH CDR3 | CDFLYWYFDV |
| 21 | JB24Chi VL aa | DIVMTQSPAIMSASLGERVTMTCTASSSVSSSYL HWYQQKPGSSPKLWIYSTSNLASGVPGRFSGSGS GTSYSLTISSMEAEDAATYYCHQYHRSPLTFGAG TKLEMK |
| 22 | JB24Chi VL nt | GACATTGTGATGACCCAGTCTCCAGCAATCATG TCTGCATCTCTAGGGGAACGGGTCACCATGACC TGCACTGCCAGCTCAAGTGTAAGTTCCAGTTAC TTGCACTGGTACCAGCAGAAGCCAGGATCCTCC CCCAAACTCTGGATTTATAGCACATCCAACCTG GCTTCTGGAGTCCCAGGTCGCTTCAGTGGCAGT GGGTCTGGGACCTCTTACTCTCTCACAATCAGC AGCATGGAGGCTGAAGATGCTGCCACTTATTAC TGCCACCAGTATCATCGTTCCCCGCTCACGTTC GGTGCTGGGACCAAGCTGGAAATGAAA |
| 23 | JB24Chi VL CDR1 | TASSSVSSSYLH |
| 24 | JB24Chi VL CDR2 | STSNLAS |
| 25 | JB24Chi VL CDR3 | HQYHRSPLT |
| 26 | JB24Chi hIgG1 full heavy chain | QVQLQQSGLELVKPGASVKMSCKASGYTFTDYN MHWVKQSHGKSLEWIGYIKPHNGGTTYNPKFEG KATLTVNKSSSTAYMELRSLTSEDSAVYYCVRCD FLYWYFDVWGTGTTVTVSSASTKGPSVFPLAPSS KSTSGGTAALGCLVKDYFPEPVTVSWNSGALTSG VHTFPAVLQSSGLYSLSSVVTVPSSSLGTQTYIC NVNHKPSNTKVDKKVEPKSCDKTHTCPPCPAPEL LGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALPAPIEKTI SKAKGQPREPQVYTLPPSRDELTKNQVSLTCLVK GFYPSDIAVEWESNGQPENNYKTTPPVLDSDGSF FLYSKLTVDKSRWQQGNVFSCSVMHEALHNHYTQ KSLSLSPGK |
| 27 | JB24Chi hIgG2 full heavy chain | QVQLQQSGLELVKPGASVKMSCKASGYTFTDYN MHWVKQSHGKSLEWIGYIKPHNGGTTYNPKFEG KATLTVNKSSSTAYMELRSLTSEDSAVYYCVRCD FLYWYFDVWGTGTTVTVSSASTKGPSVFPLAPCS RSTSESTAALGCLVKDYFPEPVTVSWNSGALTSG VHTFPAVLQSSGLYSLSSVVTVPSSNFGTQTYTC NVDHKPSNTKVDKTVERKCCVECPPCPAPPVAGP SVFLFPPKPKDTLMISRTPEVTCVVVDVSHEDPE VQFNWYVDGVEVHNAKTKPREEQFNSTFRVVSVL TVVHQDWLNGKEYKCKVSNKGLPAPIEKTISKTK GQPREPQVYTLPPSREEMTKNQVSLTCLVKGFYP SDIAVEWESNGQPENNYKTTPPMLDSDGSFFLYS KLTVDKSRWQQGNVFSCSVMHEALHNHYTQKSLS LSPGK |
| 28 | JB24Chi hkappa full light chain | DIVMTQSPAIMSASLGERVTMTCTASSSVSSSYL HWYQQKPGSSPKLWIYSTSNLASGVPGRFSGSGS GTSYSLTISSMEAEDAATYYCHQYHRSPLTFGAG TKLEMKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGEC |
| 29 | 66F2A8D6 VH aa | QVHLQQSGAELAKPGASVNLSCKASGYAFTSYW MHWVKQRPGQGLEWIGYINPSSGLAKYNQKFKD KATLTTDKSSNTAYMQLSSLTYDDSAVYYCGRW LLSAWFAYWGQGTLVTVSA |
| 30 | 66F2A8D6 VH nt | CAGGTCCACCTGCAGCAGTCTGGGGCTGAACTG GCAAAACCTGGGGCCTCAGTGAACCTGTCCTGC AAGGCTTCTGGCTACGCCTTTACTAGTTACTGG ATGCACTGGGTAAAACAGAGGCCTGGACAGGG TCTGGAATGGATTGGATACATTAATCCTAGCAG TGGTCTTGCTAAGTATAATCAGAAGTTCAAAGA CAAGGCCACATTGACTACAGACAAATCTTCCAA |

TABLE I-continued

Description of the antibody sequence listing of the invention

| SEQ ID NO: | Sequence Description | Sequence |
|---|---|---|
| | | CACAGCCTACATGCAACTGAGCAGCCTGACATA TGACGACTCTGCAGTCTATTACTGTGGAAGATG GTTACTTTCGGCCTGGTTTGCTTACTGGGGCCA AGGGACTCTGGTCACTGTCTCTGCA |
| 31 | 66F2A8D6 VH CDR1 | SYWMH |
| 32 | 66F2A8D6 VH CDR2 | YINPSSGLAKYNQKFKD |
| 33 | 66F2A8D6 VH CDR3 | WLLSAWFAY |
| 34 | 66F2A8D6 VL aa | DIKMTQSPSSIYASLGERVTITCKASQGINTYLS WFQQKPGKSPKTLIYRANILVDGVPSRFSGSGSG QDYSLTINSLEYEDMGIYYCLQYDEFPYTFGGGT KLEIK |
| 35 | 66F2A8D6 VL nt | GACATCAAGATGACCCAGTCTCCATCTTCCATA TATGCATCTCTAGGAGAGAGTCACTATCACT TGCAAGGCGAGTCAGGGCATTAATACCTATTTA AGCTGGTTCCAGCAGAAACCAGGAAAATCTCCT AAGACCCTGATCTATCGTGCAAACATCTTGGTA GATGGGGTCCCATCAAGGTTCAGTGGCAGTGGA TCTGGGCAAGATTATTCTCTCACCATCAACAGC CTGGAGTATGAAGATATGGGAATTTATTATTGT CTACAGTATGATGAGTTTCCGTACACGTTCGGA GGGGGGACCAAGCTGGAAATAAAA |
| 36 | 66F2A8D6 VL CDR1 | KASQGINTYLS |
| 37 | 66F2A8D6 VL CDR2 | RANILVD |
| 38 | 66F2A8D6 VL CDR3 | LQYDEFPYT |
| 39 | 66-hIgG2 full heavy chain | QVHLQQSGAELAKPGASVNLSCKASGYAFTSYW MHWVKQRPGQGLEWIGYINPSSGLAKYNQKFKD KATLTTDKSSNTAYMQLSSLTYDDSAVYYCGRW LLSAWFAYWGQGTLVTVSAASTKGPSVFPLAPCS RSTSESTAALGCLVKDYFPEPVTVSWNSGALTSG VHTFPAVLQSSGLYSLSSVVTVPSSNFGTQTYTC NVDHKPSNTKVDKTVERKCCVECPPCPAPPVAGP SVFLFPPKPKDTLMISRTPEVTCVVVDVSHEDPE VQFNWYVDGVEVHNAKTKPREEQFNSTFRVVSVL TVVHQDWLNGKEYKCKVSNKGLPAPIEKTISKTK GQPREPQVYTLPPSREEMTKNQVSLTCLVKGFYP SDIAVEWESNGQPENNYKTTPPMLDSDGSFFLYS KLTVDKSRWQQGNVFSCSVMHEALHNHYTQKSLS LSPGK |
| 40 | 66-hkappa full light chain | DIKMTQSPSSIYASLGERVTITCKASQGINTYLS WFQQKPGKSPKTLIYRANILVDGVPSRFSGSGSG QDYSLTINSLEYEDMGIYYCLQYDEFPYTFGGGT KLEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 41 | 94A12G11F2 VH aa | QVQLQQSGAELAKPGASVKLSCKASGYTFTSYW MHWVKQRPGQGLEWIGYINPSSGYTKSNQKFKD KATLTADKSSSTAYMQLSSLTYEDSAVYYCGRW LLSAWFAYWGQGTLVTVSA |
| 42 | 94A12G11F2 VH nt | CAGGTCCAGCTGCAGCAGTCTGGGGCTGAACTG GCAAAACCTGGGGCCTCAGTGAAGCTGTCCTGC AAGGCTTCTGGCTACACCTTTACTAGTTACTGG ATGCACTGGGTAAAACAGAGGCCTGGACAGGG TCTGGAATGGATTGGATACATTAATCCTAGCAG TGGTTATACTAAGTCCAATCAGAAGTTCAAGGA |
| 43 | 94A12G11F2 VH CDR1 | SYWMH |
| 44 | 94A12G11F2 VH CDR2 | YINPSSGYTKSNQKFKD |
| 45 | 94A12G11F2 VH CDR3 | WLLSAWFAY |
| 46 | 94A12G11F2 VL aa | DIRMTQSPSSMYASLGERVTITCKASQDINTYLS WFQQKPGKSPKSLIYRSNILVDGVPSRFSGSGSG QDYSLTISSLEYEDMGIYYCLQYDDFPYTFGGGT KLEIK |
| 47 | 94A12G11F2 VL nt | GACATCAGGATGACCCAGTCTCCATCTTCCATG TATGCATCTCTAGGAGAGAGTCACTATCACT TGCAAGGCGAGTCAGGACATTAATACCTATTTA AGCTGGTTCCAGCAGAAACCAGGAAAATCTCCT AAGTCCCTGATCTATCGCTCAAACATCTTGGTA GATGGGGTCCCATCAAGATTCAGTGGCAGTGGA TCTGGTCAAGATTATTCTCTCACCATCAGCAGC CTGGAGTATGAGGATATGGGAATTTATTATTGT CTACAGTATGATGACTTTCCGTACACGTTCGGA GGGGGGACCAAGCTGGAAATAAAA |
| 48 | 94A12G11F2 VL CDR1 | KASQDINTYLS |
| 49 | 94A12G11F2 VL CDR2 | RSNILVD |
| 50 | 94A12G11F2 VL CDR3 | LQYDDFPYT |
| 51 | 94-hIgG2 full heavy chain | QVQLQQSGAELAKPGASVKLSCKASGYTFTSYW MHWVKQRPGQGLEWIGYINPSSGYTKSNQKFKD KATLTADKSSSTAYMQLSSLTYEDSAVYYCGRW LLSAWFAYWGQGTLVTVSAASTKGPSVFPLAPCS RSTSESTAALGCLVKDYFPEPVTVSWNSGALTSG VHTFPAVLQSSGLYSLSSVVTVPSSNFGTQTYTC NVDHKPSNTKVDKTVERKCCVECPPCPAPPVAGP SVFLFPPKPKDTLMISRTPEVTCVVVDVSHEDPE VQFNWYVDGVEVHNAKTKPREEQFNSTFRVVSVL TVVHQDWLNGKEYKCKVSNKGLPAPIEKTISKTK GQPREPQVYTLPPSREEMTKNQVSLTCLVKGFYP SDIAVEWESNGQPENNYKTTPPMLDSDGSFFLYS KLTVDKSRWQQGNVFSCSVMHEALHNHYTQKSLS LSPGK |
| 52 | 94-hIgG1 full heavy chain | QVQLQQSGAELAKPGASVKLSCKASGYTFTSYWM HWVKQRPGQGLEWIGYINPSSGYTKSNQKFKDKA TLTADKSSSTAYMQLSSLTYEDSAVYYCGRWLLS AWFAYWGQGTLVTVSAASTKGPSVFPLAPSSKST SGGTAALGCLVKDYFPEPVTVSWNSGALTSGVHT FPAVLQSSGLYSLSSVVTVPSSSLGTQTYICNVN HKPSNTKVDKKVEPKSCDKTHTCPPCPAPELLGG PSVFLFPPKPKDTLMISRTPEVTCVVVDVSHEDP EVKFNWYVDGVEVHNAKTKPREEQYNSTYRVVSV LTVLHQDWLNGKEYKCKVSNKALPAPIEKTISKA KGQPREPQVYTLPPSRDELTKNQVSLTCLVKGFY PSDIAVEWESNGQPENNYKTTPPVLDSDGSFFLY SKLTVDKSRWQQGNVFSCSVMHEALHNHYTQKSL SLSPGK |
| 53 | 94-hkappa full | DIRMTQSPSSMYASLGERVTITCKASQDINTYLS WFQQKPGKSPKSLIYRSNILVDGVPSRFSGSGSG |

TABLE I-continued

Description of the antibody sequence listing of the invention

| SEQ ID NO: | Sequence Description | Sequence |
|---|---|---|
| | light chain | QDYSLTISSLEYEDMGIYYCLQYDDFPYTFGGGT KLEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 54 | 191C3A8B9 VH aa | QVQLKESGPGLVAPSQSLSITCTVSGFSLTNYGV HWRQPPGKGLEWLGVIWAGGSTNYNSALMSRLS ISKDNSKSQLFLKMNSLQADDTAMYYCARERGSS WGTMDYWGQGTSVTVSS |
| 55 | 191C3A8B9 VH nt | CAGGTGCAGCTGAAGGAGTCAGGACCTGGCCT GGTGGCGCCCTCACAGAGCCTGTCCATCACTTG CACTGTCTCTGGGTTTTCATTAACCAACTATGGT GTACACTGGGTTCGCCAGCCTCCAGGAAAGGGT CTGGAGTGGCTGGGAGTAATATGGGCTGGTGG AAGCACAAATTATAATTCGGCTCTCATGTCCAG ACTGAGCATCAGCAAAGACAACTCCAAGAGCC AACTTTTCTTAAAAATGAACAGTCTGCAAGCTG ATGACACAGCCATGTACTACTGTGCCAGAGAGA GGGGTAGTAGCTGGGGACTATGGACTACTGG GGTCAAGGAACCTCAGTCACTGTCTCCTCA |
| 56 | 191C3A8B9 VH CDR1 | NYGVH |
| 57 | 191C3A8B9 VH CDR2 | VIWAGGSTNYNSALMS |
| 58 | 191C3A8B9 VH CDR 3 | ERGSSWGTMDY |
| 59 | 191C3A8B9 VL aa | QIVLTQSPAIMSASPGEKVTMTCSASSRVSYMHW YQQKSGTSPKRWIYDTSQLASGVPARFSGSGSGT SYSLTISSMEAEDAATYYCQQWSSNPYTFGGGTK LEMR |
| 60 | 191C3A8B9 VL nt | CAAATTGTTCTCACCCAGTCTCCAGCAATCATG TCTGCATCTCCAGGGGAGAAGGTCACCATGACC TGCAGTGCCAGCTCACGTGTAAGTTACATGCAC TGGTACCAGCAGAAGTCAGGCACCTCCCCCAAA AGATGGATTTATGACACATCCCAACTGGCTTCT GGAGTCCCTGCTCGCTTCAGTGGCAGTGGGTCT GGGACCTCTTACTCTCTCACAATCAGCAGCATG GAGGCTGAAGATGCTGCCACTTATTACTGCCAG CAGTGGAGTAGTAACCCATACACGTTCGGAGG GGGGACCAAGCTGGAAATGAGA |
| 61 | 191C3A8B9 VL CDR1 | SASSRVSYMH |
| 62 | 191C3A8B9 VL CDR2 | DTSQLAS |
| 63 | 191C3A8B9 VL CDR3 | QQWSSNPYT |
| 64 | 191-hIgG2 full heavy chain | QVQLKESGPGLVAPSQSLSITCTVSGFSLTNYGV HWRQPPGKGLEWLGVIWAGGSTNYNSALMSRLS ISKDNSKSQLFLKMNSLQADDTAMYYCARERGSS WGTMDYWGQGTSVTVSSASTKGPSVFPLAPCSRS TSESTAALGCLVKDYFPEPVTVSWNSGALTSGVH TFPAVLQSSGLYSLSSVVTVPSSNFGTQTYTCNV DHKPSNTKVDKTVERKCCVECPPCPAPPVAGPSV FLFPPKPKDTLMISRTPEVTCVVVDVSHEDPEVQ FNWYVDGVEVHNAKTKPREEQFNSTFRVVSVLTV VHQDWLNGKEYKCKVSNKGLPAPIEKTISKTKGQ PREPQVYTLPPSREEMTKNQVSLTCLVKGFYPSD IAVEWESNGQPENNYKTTPPMLDSDGSFFLYSKL TVDKSRWQQGNVFSCSVMHEALHNHYTQKSLSLS PGK |
| 65 | 191-hkappa full light chain | QIVLTQSPAIMSASPGEKVTMTCSASSRVSYMHW YQQKSGTSPKRWIYDTSQLASGVPARFSGSGSGT SYSLTISSMEAEDAATYYCQQWSSNPYTFGGGTK LEMRRTVAAPSVFIFPPSDEQLKSGTASVVCLLN NFYPREAKVQWKVDNALQSGNSQESVTEQDSKDS TYSLSSTLTLSKADYEKHKVYACEVTHQGLSSPV TKSFNRGEC |
| 66 | JB24H2 VH | QVQLVQSGAEVKKPGASVKMSCKASGYTFTDYN MHWVRQSPGKSLEWIGYIKPHNAGTTYNPKFEGR ATLTVDTSASTAYMELSSLRSEDTAVYYCVRSDF LYWYFDVWGQGTTVTVSS |
| 67 | JB24H3 VH | QVQLVQSGAEVKKPGASVKMSCKASGYTFTDYN MHWVKQSHGKSLEWIGYIKPHNAGTTYNPKFEG RATLTVDTSASTAYMELRSLRSEDTAVYYCVRSD FLYWYFDVWGQGTTVTVSS |
| 68 | JB24L1 VL | DIQMTQSPSSLSASVGDRVTITCTASSSVSSSYL HWYQQKPGKAPKLLIYSTSNLASGVPSRFSGSGS GTDFTLTISSLQPEDFATYYCHQYHRSPLTFGAG TKLEIK |
| 69 | JB24L2 VL | DIQMTQSPSSLSASVGDRVTITCTASSSVSSSYL HWYQQKPGSAPKLWIYSTSNLASGVPSRFSGSGS GTDYTLTISSLQPEDFATYYCHQYHRSPLTFGAG TKLEIK |
| 70 | JB24L3 VL | DIVMTQSPSSLSASVGDRVTITCTASSSVSSSYL HWYQQKPGSSPKLWIYSTSNLASGVPGRFSGSGS GTDYTLTISSLQPEDFATYYCHQYHRSPLTFGAG TKLEIK |
| 71 | JB24H2 hIgG1 full heavy chain | QVQLVQSGAEVKKPGASVKMSCKASGYTFTDYN MHWVRQSPGKSLEWIGYIKPHNAGTTYNPKFEGR ATLTVDTSASTAYMELSSLRSEDTAVYYCVRSDF LYWYFDVWGQGTTVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKKVEPKSCDKTHTCPPCPAPELL GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALPAPIEKTIS KAKGQPREPQVYTLPPSRDELTKNQVSLTCLVKG FYPSDIAVEWESNGQPENNYKTTPPVLDSDGSFF LYSKLTVDKSRWQQGNVFSCSVMHEALHNHYTQK SLSLSPGK |
| 72 | JB24H3 hIgG1 full heavy chain | QVQLVQSGAEVKKPGASVKMSCKASGYTFTDYN MHWVKQSHGKSLEWIGYIKPHNAGTTYNPKFEG RATLTVDTSASTAYMELRSLRSEDTAVYYCVRSD FLYWYFDVWGQGTTVTVSSASTKGPSVFPLAPSS KSTSGGTAALGCLVKDYFPEPVTVSWNSGALTSG VHTFPAVLQSSGLYSLSSVVTVPSSSLGTQTYIC NVNHKPSNTKVDKKVEPKSCDKTHTCPPCPAPEL LGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALPAPIEKTI SKAKGQPREPQVYTLPPSRDELTKNQVSLTCLVK GFYPSDIAVEWESNGQPENNYKTTPPVLDSDGSF FLYSKLTVDKSRWQQGNVFSCSVMHEALHNHYTQ KSLSLSPGK |
| 73 | JB24L1 hkappa full light chain | DIQMTQSPSSLSASVGDRVTITCTASSSVSSSYL HWYQQKPGKAPKLLIYSTSNLASGVPSRFSGSGS GTDFTLTISSLQPEDFATYYCHQYHRSPLTFGAG TKLEIKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGEC |

TABLE I-continued

Description of the antibody sequence listing of the invention

| SEQ ID NO: | Sequence Description | Sequence |
|---|---|---|
| 74 | JB24L2 hkappa full light chain | DIQMTQSPSSLSASVGDRVTITCTASSSVSSSYL HWYQQKPGSAPKLWIYSTSNLASGVPSRFSGSGS GTDYTLTISSLQPEDFATYYCHQYHRSPLTFGAG TKLEIKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGEC |
| 75 | JB24L3 hkappa full light chain | DIVMTQSPSSLSASVGDRVTITCTASSSVSSSYL HWYQQKPGSSPKLWIYSTSNLASGVPSRFSGSGS GTDYTLTISSLQPEDFATYYCHQYHRSPLTFGAG TKLEIKRTVAAPSVFIFPPSDEQLKSGTASVVCL LNNFYPREAKVQWKVDNALQSGNSQESVTEQDSK DSTYSLSSTLTLSKADYEKHKVYACEVTHQGLSS PVTKSFNRGEC |
| 76 | JB94H1 VH | QVQLVQSGAEVKKPGASVKVSCKASGYTFTSYW MHWVRQAPGQGLEWMGYINPSSGYTKSNQKFK DRVTMTADTSTSTAYMELSSLRSEDTAVYYCGR WLLSAWFAYWGQGTLVTVSS |
| 77 | JB94H2 VH | QVQLVQSGAEVKKPGASVKVSCKASGYTFTSYW MHWVRQRPGQGLEWMGYINPSSGYTKSNQKFK DRVTLTADTSTSTAYMELSSLRSEDTAVYYCGRW LLSAWFAYWGQGTLVTVSS |
| 78 | JB94H3 VH | QVQLQQSGAEVKKPGASVKLSCKASGYTFTSYW MHWVRQRPGQGLEWIGYINPSSGYTKSNQKFKD RATLTADTSTSTAYMELSSLRSEDTAVYYCGRWL LSAWFAYWGQGTLVTVSS |
| 79 | JB94L1 VL | DIQMTQSPSSLSASVGDRVTITCKASQDINTYLS WFQQKPGKAPKSLIYRSNILVDGVPSRFSGSGSG QDFTLTISSLQPEDFAIYYCLQYDDFPYTFGQGT KLEIK |
| 80 | JB94L3 VL | DIQMTQSPSSLSASVGDRVTITCKASQDINTYLS WFQQKPGKSPKSLIYRSNILVDGVPSRFSGSGSG QDYTLTISSLQPEDFAIYYCLQYDDFPYTFGQGT KLEIK |
| 81 | JB94H1 hIgG1 full heavy chain | QVQLVQSGAEVKKPGASVKVSCKASGYTFTSYW MHWVRQAPGQGLEWMGYINPSSGYTKSNQKFK DRVTMTADTSTSTAYMELSSLRSEDTAVYYCGR WLLSAWFAYWGQGTLVTVSSASTKGPSVFPLAPS SKSTSGGTAALGCLVKDYFPEPVTVSWNSGALTS GVHTFPAVLQSSGLYSLSSVVTVPSSSLGTQTYI CNVNHKPSNTKVDKKVEPKSCDKTHTCPPCPAPE LLGGPSVFLFPPKPKDTLMISRTPEVTCVVVDVS HEDPEVKFNWYVDGVEVHNAKTKPREEQYNSTYR VVSVLTVLHQDWLNGKEYKCKVSNKALPAPIEKT ISKAKGQPREPQVYTLPPSRDELTKNQVSLTCLV KGFYPSDIAVEWESNGQPENNYKTTPPVLDSDGS FFLYSKLTVDKSRWQQGNVFSCSVMHEALHNHYT QKSLSLSPGK |
| 82 | JB94H2 hIgG1 full heavy chain | QVQLVQSGAEVKKPGASVKVSCKASGYTFTSYW MHWVRQRPGQGLEWMGYINPSSGYTKSNQKFK DRVTLTADTSTSTAYMELSSLRSEDTAVYYCGRW LLSAWFAYWGQGTLVTVSSASTKGPSVFPLAPSS KSTSGGTAALGCLVKDYFPEPVTVSWNSGALTSG VHTFPAVLQSSGLYSLSSVVTVPSSSLGTQTYIC NVNHKPSNTKVDKKVEPKSCDKTHTCPPCPAPEL LGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALPAPIEKTI SKAKGQPREPQVYTLPPSRDELTKNQVSLTCLVK GFYPSDIAVEWESNGQPENNYKTTPPVLDSDGSF FLYSKLTVDKSRWQQGNVFSCSVMHEALHNHYTQ KSLSLSPGK |
| 83 | JB94H3 hIgG1 full heavy chain | QVQLQQSGAEVKKPGASVKLSCKASGYTFTSYW MHWVRQRPGQGLEWIGYINPSSGYTKSNQKFKD RATLTADTSTSTAYMELSSLRSEDTAVYYCGRWL LSAWFAYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKKVEPKSCDKTHTCPPCPAPELL GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALPAPIEKTIS KAKGQPREPQVYTLPPSRDELTKNQVSLTCLVKG FYPSDIAVEWESNGQPENNYKTTPPVLDSDGSFF LYSKLTVDKSRWQQGNVFSCSVMHEALHNHYTQK SLSLSPGK |
| 84 | JB94L1 hkappa full light chain | DIQMTQSPSSLSASVGDRVTITCKASQDINTYLS WFQQKPGKAPKSLIYRSNILVDGVPSRFSGSGSG QDFTLTISSLQPEDFAIYYCLQYDDFPYTFGQGT KLEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 85 | JB94L3 hkappa full light chain | DIQMTQSPSSLSASVGDRVTITCKASQDINTYLS WFQQKPGKSPKSLIYRSNILVDGVPSRFSGSGSG QDYTLTISSLQPEDFAIYYCLQYDDFPYTFGQGT KLEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| 86 | JB94H1 mIgG1 full heavy chain | QVQLVQSGAEVKKPGASVKVSCKASGYTFTSYW MHWVRQAPGQGLEWMGYINPSSGYTKSNQKFK DRVTMTADTSTSTAYMELSSLRSEDTAVYYCGR WLLSAWFAYWGQGTLVTVSSAKTTPPSVYPLAP GSAAQTNSMVTLGCLVKGYFPEPVTVTWNSGSLS SGVHTFPAVLQSDLYTLSSSVTVPSSTWPSETVT CNVAHPASSTKVDKKIVPRDCGCKPCICTVPEVS SVFIFPPKPKDVLTITLTPKVTCVVVDISKDDPE VQFSWFVDDVEVHTAQTQPREEQFNSTFRSVSEL PIMHQDWLNGKEFKCRVNSAAFPAPIEKTISKTK GRPKAPQVYTIPPPKEQMAKDKVSLTCMITDFFP EDITVEWQWNGQPAENYKNTQPIMDTDGSYFVYS KLNVQKSNWEAGNTFTCSVLHEGLHNHHTEKSLS HSPGK |
| 87 | JB94H3 mIgG1 full heavy chain | QVQLQQSGAEVKKPGASVKLSCKASGYTFTSYW MHWVRQRPGQGLEWIGYINPSSGYTKSNQKFKD RATLTADTSTSTAYMELSSLRSEDTAVYYCGRWL LSAWFAYWGQGTLVTVSSAKTTPPSVYPLAPGSA AQTNSMVTLGCLVKGYFPEPVTVTWNSGSLSSGV HTFPAVLQSDLYTLSSSVTVPSSTWPSETVTCNV AHPASSTKVDKKIVPRDCGCKPCICTVPEVSSVF IFPPKPKDVLTITLTPKVTCVVVDISKDDPEVQF SWFVDDVEVHTAQTQPREEQFNSTFRSVSELPIM HQDWLNGKEFKCRVNSAAFPAPIEKTISKTKGRP KAPQVYTIPPPKEQMAKDKVSLTCMITDFFPEDI TVEWQWNGQPAENYKNTQPIMDTDGSYFVYSKLN VQKSNWEAGNTFTCSVLHEGLHNHHTEKSLSHSP GK |
| 88 | JB94L1 mkappa full light chain | DIQMTQSPSSLSASVGDRVTITCKASQDINTYLS WFQQKPGKAPKSLIYRSNILVDGVPSRFSGSGSG QDFTLTISSLQPEDFAIYYCLQYDDFPYTFGQGT KLEIKRADAAPTVSIFPPSSEQLTSGGASVVCFL NNFYPKDINVKWKIDGSERQNGVLNSWTDQDSKD STYSMSSTLTLTKDEYERHNSYTCEATHKTSTSP IVKSFNRNEC |
| 89 | JB94L3 mkappa full | DIQMTQSPSSLSASVGDRVTITCKASQDINTYLS WFQQKPGKSPKSLIYRSNILVDGVPSRFSGSGSG QDYTLTISSLQPEDFAIYYCLQYDDFPYTFGQGT |

TABLE I-continued

Description of the antibody sequence listing of the invention

| SEQ ID NO: | Sequence Description | Sequence |
|---|---|---|
| | light chain | KLEIKRADAAPTVSIFPPSSEQLTSGGASVVCFL NNFYPKDINVKWKIDGSERQNGVLNSWTDQDSKD STYSMSSTLTLTKDEYERHNSYTCEATHKTSTSP IVKSFNRNEC |
| 90 | JB94H1 hIgG1mt full heavy chain | QVQLVQSGAEVKKPGASVKVSCKASGYTFTSYW MHWVRQAPGQGLEWMGYINPSSGYTKSNQKFK DRVTMTADTSTSTAYMELSSLRSEDTAVYYCGR WLLSAWFAYWGQGTLVTVSSASTKGPSVFPLAPS SKSTSGGTAALGCLVKDYFPEPVTVSWNSGALTS GVHTFPAVLQSSGLYSLSSVVTVPSSSLGTQTYI CNVNHKPSNTKVDKRVEPKSCDKTHTCPPCPAPE FEGGPSVFLFPPKPKDTLMISRTPEVTCVVVDVS HEDPEVKFNWYVDGVEVHNAKTKPREEQYNSTYR VVSVLTVLHQDWLNGKEYKCKVSNKALPASIEKT ISKAKGQPREPQVYTLPPSREEMTKNQVSLTCLV KGFYPSDIAVEWESNGQPENNYKTTPPVLDSDGS FFLYSKLTVDKSRWQQGNVFSCSVMHEALHNHYT QKSLSLSPGK |
| 91 | JB94H3 hIgG1mt full heavy chain | QVQLQQSGAEVKKPGASVKLSCKASGYTFTSYW MHWVRQRPGQGLEWIGYINPSSGYTKSNQKFKD RATLTADTSTSTAYMELSSLRSEDTAVYYCGRWL LSAWFAYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKRVEPKSCDKTHTCPPCPAPEFE GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALPASIEKTIS KAKGQPREPQVYTLPPSREEMTKNQVSLTCLVKG FYPSDIAVEWESNGQPENNYKTTPPVLDSDGSFF LYSKLTVDKSRWQQGNVFSCSVMHEALHNHYTQK SLSLSPGK |
| 92 | JB24H2 VH nt | CAGGTGCAGCTGGTGCAGAGCGGCGCCGAGGT GAAGAAGCCCGGCGCCAGCGTGAAGATGAGCT GCAAGGCCAGCGGCTACACCTTCACCGACTACA ACATGCACTGGGTGAGACAGAGCCCCGGCAAG AGCCTGGAGTGGATCGGCTACATCAAGCCCCAC AACGCCGGCACCACCTACAACCCCAAGTTCGA GGGCAGAGCCACCCTGACCGTGGACACCAGCG CCAGCACCGCCTACATGGAGCTGAGCAGCCTGA GAAGCGAGGACACCGCCGTGTACTACTGCGTA AGAAGCGACTTCCTGTACTGGTACTTCGACGTG TGGGGCCAGGGCACCACCGTGACCGTGTCCTCA |
| 93 | JB24H3 VH nt | CAGGTGCAGCTGGTGCAGAGCGGCGCCGAGGT GAAGAAGCCCGGCGCCAGCGTGAAGATGAGCT GCAAGGCCAGCGGCTACACCTTCACCGACTACA ACATGCACTGGGTGAAGCAGAGCCACGGCAAG AGCCTGGAGTGGATCGGCTACATCAAGCCCCAC AACGCCGGCACCACCTACAACCCCAAGTTCGA GGGCAGAGCCACCCTGACCGTGGACACCAGCG CCAGCACCGCCTACATGGAGCTGAGAAGCCTG AGAAGCGAGGACACCGCCGTGTACTACTGCGT AAGAAGCGATTTTCTCTACTGGTATTTCGATGT CTGGGGCCAGGGCACCACCGTGACCGTGTCCTC A |
| 94 | JB24L1 VL nt | GACATCCAGATGACCCAGAGCCCCAGCAGCCT GAGCGCCAGCGTGGGCGACAGAGTGACCATCA CCTGCACCGCCAGCAGCAGCGTGAGCAGCAGC TACCTGCACTGGTACCAGCAGAAGCCCGGCAA GGCCCCCAAGCTGCTGATCTACAGCACCAGCAA CCTGGCCAGCGGCGTGCCCAGCAGATTCAGCGGC CAGCGGCAGCGGCACCGACTTCACCCTGACCAT CAGCAGCCTGCAGCCCGAGGACTTCGCCACCTA CTACTGCCACCAGTATCATCGTTCCCCGCTCAC GTTCGGCGCCGGCACCAAGCTGGAGATCAAG |
| 95 | JB24L2 VL nt | GACATCCAGATGACCCAGAGCCCCAGCAGCCT GAGCGCCAGCGTGGGCGACAGAGTGACCATCA CCTGCACCGCCAGCAGCAGCGTGAGCAGCAGC TACCTGCACTGGTACCAGCAGAAGCCCGGCAGC GCCCCCAAGCTGTGGATCTACAGCACCAGCAAC CTGGCCAGCGGCGTGCCCAGCAGATTCAGCGGC AGCGGCAGCGGCACCGACTACACCCTGACCAT CAGCAGCCTGCAGCCCGAGGACTTCGCCACCTA CTACTGCCACCAGTATCATCGTTCCCCGCTCAC GTTCGGCGCCGGCACCAAGCTGGAGATCAAG |
| 96 | JB24L3 VL nt | GACATCGTGATGACCCAGAGCCCCAGCAGCCTG AGCGCCAGCGTGGGCGACAGAGTGACCATCAC CTGCACCGCCAGCAGCAGCGTGAGCAGCAGCT ACCTGCACTGGTACCAGCAGAAGCCCGGCAGC AGCCCCAAGCTGTGGATCTACAGCACCAGCAAC CTGGCCAGCGGCGTGCCCAGCAGATTCAGCGGC AGCGGCAGCGGCACCGACTACACCCTGACCAT CAGCAGCCTGCAGCCCGAGGACTTCGCCACCTA CTACTGCCACCAGTATCATCGTTCCCCGCTCAC GTTCGGCGCCGGCACCAAGCTGGAGATCAAG |
| 97 | JB24H2 hIgG1 full heavy chain nt | CAGGTGCAGCTGGTGCAGAGCGGCGCCGAGGT GAAGAAGCCCGGCGCCAGCGTGAAGATGAGCT GCAAGGCCAGCGGCTACACCTTCACCGACTACA ACATGCACTGGGTGAGACAGAGCCCCGGCAAG AGCCTGGAGTGGATCGGCTACATCAAGCCCCAC AACGCCGGCACCACCTACAACCCCAAGTTCGA GGGCAGAGCCACCCTGACCGTGGACACCAGCG CCAGCACCGCCTACATGGAGCTGAGCAGCCTGA GAAGCGAGGACACCGCCGTGTACTACTGCGTA AGAAGCGACTTCCTGTACTGGTACTTCGACGTG TGGGGCCAGGGCACCACCGTGACCGTGTCCAGC GCCTGACCAGCGGCGTGCACACCTTCCCGGCT GTCCTACAGTCCTCAGGACTCTACTCCCTCAGC AGCGTGGTGACCGTGCCCTCCAGCAGCTTGGGC ACCCAGACCTACATCTGCAACGTGAATCACAAG CCCAGCAACACCAAGGTGGACAAGAAAGTTGA GCCCAAATCTTGTGACAAAACTCACACATGCCC ACCGTGCCCAGCACCTGAACTCCTGGGGGGACC GTCAGTCTTCCTCTTCCCCCCAAAACCCAAGGA CACCCTCATGATCTCCCGGACCCCTGAGGTCAC ATGCGTGGTGGTGGACGTGAGCCACGAAGACC CTGAGGTCAAGTTCAACTGGTACGTGGACGGCG TGGAGGTGCATAATGCCAAGACAAAGCCGCGG GAGGAGCAGTACAACAGCACGTACCGTGTGGT CAGCGTCCTCACCGTCCTGCACCAGGACTGGCT GAATGGCAAGGAGTACAAGTGCAAGGTCTCCA ACAAAGCCCTCCCAGCCCCCATCGAGAAAACC ATCTCCAAAGCCAAAGGGCAGCCCCGAGAACC ACAGGTGTACACCCTGCCCCCATCCCGGGATGA GTTGACCAAGAACCAGGTCAGCCTGACCTGCCT GGTCAAAGGCTTCTATCCCAGCGACATCGCCGT GGAGTGGGAGAGCAATGGGCAGCCGGAGAACA ACTACAAGACCACGCCTCCCGTGCTGGACTCCG ACGGCTCCTTCTTCCTCTACAGCAAGCTCACCG TGGACAAGAGCAGGTGGCAGCAGGGGAACGTC TTCTCATGCTCCGTGATGCATGAGGCTCTGCAC AACCACTACACGCAGAAGAGCCTCTCCCTGTCT CCGGGTAAA |
| 98 | JB24H3 hIgG1 full heavy chain nt | CAGGTGCAGCTGGTGCAGAGCGGCGCCGAGGT GAAGAAGCCCGGCGCCAGCGTGAAGATGAGCT GCAAGGCCAGCGGCTACACCTTCACCGACTACA ACATGCACTGGGTGAAGCAGAGCCACGGCAAG AGCCTGGAGTGGATCGGCTACATCAAGCCCCAC AACGCCGGCACCACCTACAACCCCAAGTTCGA GGGCAGAGCCACCCTGACCGTGGACACCAGCG CCAGCACCGCCTACATGGAGCTGAGAAGCCTG AGAAGCGAGGACACCGCCGTGTACTACTGCGT AAGAAGCGATTTTCTCTACTGGTATTTCGATGT |

TABLE I-continued

Description of the antibody sequence listing of the invention

| SEQ ID NO: | Sequence Description | Sequence |
|---|---|---|
| | | CTGGGGCCAGGGCACCACCGTGACCGTGTCCTC AGCTAGCACCAAGGGCCCATCGGTCTTCCCCCT GGCACCCTCCTCCAAGAGCACCTCTGGGGGCAC AGCGGCCCTGGGCTGCCTGGTCAAGGACTACTT CCCCGAACCGGTGACGGTGTCGTGGAACTCAGG CGCCCTGACCAGCGGCGTGCACACCTTCCCGGC TGTCCTACAGTCCTCAGGACTCTACTCCCTCAG CAGCGTGGTGACCGTGCCCTCCAGCAGCTTGGG CACCCAGACCTACATCTGCAACGTGAATCACAA GCCCAGCAACACCAAGGTGGACAAGAAAGTTG AGCCCAAATCTTGTGACAAAACTCACACATGCC CACCGTGCCCAGCACCTGAACTCCTGGGGGGAC CGTCAGTCTTCCTCTTCCCCCCAAAACCCAAGG ACACCCTCATGATCTCCCGGACCCCTGAGGTCA CATGCGTGGTGGTGGACGTGAGCCACGAAGAC CCTGAGGTCAAGTTCAACTGGTACGTGGACGGC GTGGAGGTGCATAATGCCAAGACAAAGCCGCG GGAGGAGCAGTACAACAGCACGTACCGTGTGG TCAGCGTCCTCACCGTCCTGCACCAGGACTGGC TGAATGGCAAGGAGTACAAGTGCAAGGTCTCC AACAAAGCCCTCCCAGCCCCCATCGAGAAAAC CATCTCCAAAGCCAAAGGGCAGCCCCGAGAAC CACAGGTGTACACCCTGCCCCCATCCCGGGATG AGTTGACCAAGAACCAGGTCAGCCTGACCTGCC TGGTCAAAGGCTTCTATCCCAGCGACATCGCCG TGGAGTGGGAGAGCAATGGGCAGCCGGAGAAC AACTACAAGACCACGCCTCCCGTGCTGGACTCC GACGGCTCCTTCTTCCTCTACAGCAAGCTCACC GTGGACAAGAGCAGGTGGCAGCAGGGGAACGT CTTCTCATGCTCCGTGATGCATGAGGCTCTGCA CAACCACTACACGCAGAAGAGCCTCTCCCTGTC TCCGGGTAAA |
| 99 | JB24L1 hkappa full light chain nt | GACATCCAGATGACCCAGAGCCCCAGCAGCCT GAGCGCCAGCGTGGGCGACAGAGTGACCATCA CCTGCACCGCCAGCAGCAGCGTGAGCAGCAGC TACCTGCACTGGTACCAGCAGAAGCCCGGCAA GGCCCCCAAGCTGCTGATCTACAGCACCAGCAA CCTGGCCAGCGGCGTGCCCAGCAGATTCAGCGG CAGCGGCAGCGGCACCGACTTCACCCTGACCAT CAGCAGCCTGCAGCCCGAGGACTTCGCCACCTA CTACTGCCACCAGTATCATCGTTCCCCGCTCAC GTTCGGCGCCGGCACCAAGCTGGAGATCAAGC GTACGGTGGCTGCACCATCTGTCTTCATCTTCC GCCATCTGATGAGCAGTTGAAATCTGGAACTGC CTCTGTTGTGTGCCTGCTGAATAACTTCTATCCC AGAGAGGCCAAAGTACAGTGGAAGGTGGATAA CGCCCTCCAATCGGGTAACTCCCAGGAGAGTGT CACAGAGCAGGACAGCAAGGACAGCACCTACA GCCTCAGCAGCACCCTGACGCTGAGCAAAGCA GACTACGAGAAACACAAAGTCTACGCCTGCGA AGTCACCCATCAGGGCCTGAGCTCGCCCGTCAC AAAGAGCTTCAACAGGGGAGAGTGT |
| 100 | JB24L2 hkappa full light chain nt | GACATCCAGATGACCCAGAGCCCCAGCAGCCT GAGCGCCAGCGTGGGCGACAGAGTGACCATCA CCTGCACCGCCAGCAGCAGCGTGAGCAGCAGC TACCTGCACTGGTACCAGCAGAAGCCCGGCAGC GCCCCCAAGCTGTGGATCTACAGCACCAGCAAC CTGGCCAGCGGCGTGCCCAGCAGATTCAGCGGC AGCGGCAGCGGCACCGACTACACCCTGACCAT CAGCAGCCTGCAGCCCGAGGACTTCGCCACCTA CTACTGCCACCAGTATCATCGTTCCCCGCTCAC GTTCGGCGCCGGCACCAAGCTGGAGATCAAGC GTACGGTGGCTGCACCATCTGTCTTCATCTTCCC GCCATCTGATGAGCAGTTGAAATCTGGAACTGC CTCTGTTGTGTGCCTGCTGAATAACTTCTATCCC AGAGAGGCCAAAGTACAGTGGAAGGTGGATAA CGCCCTCCAATCGGGTAACTCCCAGGAGAGTGT CACAGAGCAGGACAGCAAGGACAGCACCTACA GCCTCAGCAGCACCCTGACGCTGAGCAAAGCA GACTACGAGAAACACAAAGTCTACGCCTGCGA AGTCACCCATCAGGGCCTGAGCTCGCCCGTCAC AAAGAGCTTCAACAGGGGAGAGTGT |
| 101 | JB24L3 hkappa full light chain nt | GACATCGTGATGACCCAGAGCCCCAGCAGCCTG AGCGCCAGCGTGGGCGACAGAGTGACCATCAC CTGCACCGCCAGCAGCAGCGTGAGCAGCAGCT ACCTGCACTGGTACCAGCAGAAGCCCGGCAGC AGCCCCAAGCTGTGGATCTACAGCACCAGCAAC CTGGCCAGCGGCGTGCCCGGCAGATTCAGCGGC AGCGGCAGCGGCACCGACTACACCCTGACCAT CAGCAGCCTGCAGCCCGAGGACTTCGCCACCTA CTACTGCCACCAGTATCATCGTTCCCCGCTCAC GTTCGGCGCCGGCACCAAGCTGGAGATCAAGC GTACGGTGGCTGCACCATCTGTCTTCATCTTCCC GCCATCTGATGAGCAGTTGAAATCTGGAACTGC CTCTGTTGTGTGCCTGCTGAATAACTTCTATCCC AGAGAGGCCAAAGTACAGTGGAAGGTGGATAA CGCCCTCCAATCGGGTAACTCCCAGGAGAGTGT CACAGAGCAGGACAGCAAGGACAGCACCTACA GCCTCAGCAGCACCCTGACGCTGAGCAAAGCA GACTACGAGAAACACAAAGTCTACGCCTGCGA AGTCACCCATCAGGGCCTGAGCTCGCCCGTCAC AAAGAGCTTCAACAGGGGAGAGTGT |
| 102 | JB94H1 VH nt | CAGGTGCAGCTGGTGCAGAGCGGCGCCGAGGT GAAGAAGCCCGGCGCCAGCGTGAAGGTGAGCT GCAAGGCCAGCGGCTACACCTTCACCAGCTACT GGATGCACTGGGTGAGACAGGCCCCCGGCCAG GGCCTGGAGTGGATGGGCTACATCAACCCCAGC AGCGGCTACACCAAGAGCAACCAGAAGTTCAA GGACAGAGTGACCATGACCGCCGACACCAGCA CCAGCACCGCCTACATGGAGCTGAGCAGCCTGA GAAGCGAGGACACCGCCGTGTACTACTGCGGA AGATGGTTACTTTCGGCCTGGTTTGCTTACTGG GGCCAGGGCACCCTGGTGACCGTGAGCAGC |
| 103 | JB94H2 VH nt | CAGGTGCAGCTGGTGCAGAGCGGCGCCGAGGT GAAGAAGCCCGGCGCCAGCGTGAAGGTGAGCT GCAAGGCCAGCGGCTACACCTTCACCAGCTACT GGATGCACTGGGTGAGACAGAGACCCGGCCAG GGCCTGGAGTGGATGGGCTACATCAACCCCAGC AGCGGCTACACCAAGAGCAACCAGAAGTTCAA GGACAGAGTGACCGCCGCCGACACCAGCA CCAGCACCGCCTACATGGAGCTGAGCAGCCTGA GAAGCGAGGACACCGCCGTGTACTACTGCGGC AGATGGCTGCTGAGCGCCTGGTTCGCCTACTGG GGCCAGGGCACCCTGGTGACCGTGAGCAGC |
| 104 | JB94H3 VH nt | CAGGTGCAGCTGCAGCAGAGCGGCGCCGAGGT GAAGAAGCCCGGCGCCAGCGTGAAGCTGAGCT GCAAGGCCAGCGGCTACACCTTCACCAGCTACT GGATGCACTGGGTGAGACAGAGACCCGGCCAG GGCCTGGAGTGGATCGGCTACATCAACCCCAGC AGCGGCTACACCAAGAGCAACCAGAAGTTCAA GGACAGAGCACCCTGACCGCCGACACCAGCA CCAGCACCGCCTACATGGAGCTGAGCAGCCTGA GAAGCGAGGACACCGCCGTGTACTACTGCGGC AGATGGCTGCTGAGCGCCTGGTTCGCCTACTGG GGCCAGGGCACCCTGGTGACCGTGAGCAGC |
| 105 | JB94L1 VL nt | GACATCCAGATGACCCAGAGCCCCAGCAGCCT GAGCGCCAGCGTGGGCGACAGAGTGACCATCA CCTGCAAGGCCAGCCAGGACATCAACACCTAC CTGAGCTGGTTCCAGCAGAAGCCCGGCAAGGC CCCCAAGAGCCTGATCTACAGAAGCAACATCCT GGTGGACGGCGTGCCCAGCAGATTCAGCGGCA GCGGCAGCGGCCAGGACTTCACCCTGACCATCA GCAGCCTGCAGCCCGAGGACTTCGCCATCTACT ACTGCCTACAGTATGATGACTTTCCGTACACGT TCGGCCAGGGCACCAAGCTGGAGATCAAG |

TABLE I-continued

Description of the antibody sequence listing of the invention

| SEQ ID NO: | Sequence Description | Sequence |
|---|---|---|
| 106 | JB94L3 VL nt | GACATCCAGATGACCCAGAGCCCCAGCAGCCT GAGCGCCAGCGTGGGCGACAGAGTGACCATCA CCTGCAAGGCCAGCCAGGACATCAACACCTAC CTGAGCTGGTTCCAGCAGAAGCCCGGCAAGAG CCCCAAGAGCCTGATCTACAGAAGCAACATCCT GGTGGACGGCGTGCCCAGCAGATTCAGCGGCA GCGGCAGCGGCCAGGACTACACCCTGACCATC AGCAGCCTGCAGCCCGAGGACTTCGCCATCTAC TACTGCCTACAGTATGATGACTTTCCGTACACG TTCGGCCAGGGCACCAAGCTGGAGATCAAG |
| 107 | JB94H1 hIgG1 full heavy chain nt | CAGGTGCAGCTGGTGCAGAGCGGCGCCGAGGT GAAGAAGCCCGGCGCCAGCGTGAAGGTGAGCT GCAAGGCCAGCGGCTACACCTTCACCAGCTACT GGATGCACTGGGTGAGACAGGCCCCCGGCCAG GGCCTGGAGTGGATGGGCTACATCAACCCCAGC AGCGGCTACACCAAGAGCAACCAGAAGTTCAA GGACAGAGTGACCATGACCGCCGACACCAGCA CCAGCACCGCCTACATGGAGCTGAGCAGCCTGA GAAGCGAGGACACCGCCGTGTACTACTGCGGA AGATGGTTACTTTCGGCCTGGTTTGCTTACTGG GGCCAGGGCACCCTGGTGACCGTGAGCAGCGC TAGCACCAAGGGCCCATCGGTCTTCCCCCTGGC ACCCTCCTCCAAGAGCACCTCTGGGGGCACAGC GGCCCTGGGCTGCCTGGTCAAGGACTACTTCCC CGAACCGGTGACGGTGTCGTGGAACTCAGGCG CCCTGACCAGCGGCGTGCACACCTTCCCGGCTG TCCTACAGTCCTCAGGACTCTACTCCCTCAGCA GCGTGGTGACCGTGCCCTCCAGCAGCTTGGGCA CCCAGACCTACATCTGCAACGTGAATCACAAGC CCAGCAACACCAAGGTGGACAAGAAAGTTGAG CCCAAATCTTGTGACAAAACTCACACATGCCCA CCGTGCCCAGCACCTGAACTCCTGGGGGGACCG TCAGTCTTCCTCTTCCCCCCAAAACCCAAGGAC ACCCTCATGATCTCCCGGACCCCTGAGGTCACA TGCGTGGTGGTGGACGTGAGCCACGAAGACCCT GAGGTCAAGTTCAACTGGTACGTGGACGGCGTG GAGGTGCATAATGCCAAGACAAAGCCGCGGGA GGAGCAGTACAACAGCACGTACCGTGTGGTCA GCGTCCTCACCGTCCTGCACCAGGACTGGCTGA ATGGCAAGGAGTACAAGTGCAAGGTCTCCAAC AAAGCCCTCCCAGCCCCCATCGAGAAAACCATC TCCAAAGCCAAAGGGCAGCCCCGAGAACCACA GGTGTACACCCTGCCCCCATCCCGGGATGAGTT GACCAAGAACCAGGTCAGCCTGACCTGCCTGGT CAAAGGCTTCTATCCCAGCGACATCGCCGTGGA GTGGGAGAGCAATGGGCAGCCGGAGAACAACT ACAAGACCACGCCTCCCGTGCTGGACTCCGACG GCTCCTTCTTCCTCTACAGCAAGCTCACCGTGG ACAAGAGCAGGTGGCAGCAGGGGAACGTCTTC TCATGCTCCGTGATGCATGAGGCTCTGCACAAC CACTACACGCAGAAGAGCCTCTCCCTGTCTCCG GGTAAA |
| 108 | JB94H2 hIgG1 full heavy chain nt | CAGGTGCAGCTGGTGCAGAGCGGCGCCGAGGT GAAGAAGCCCGGCGCCAGCGTGAAGGTGAGCT GCAAGGCCAGCGGCTACACCTTCACCAGCTACT GGATGCACTGGGTGAGACAGAGACCCGGCCAG GGCCTGGAGTGGATGGGCTACATCAACCCCAGC AGCGGCTACACCAAGAGCAACCAGAAGTTCAA GGACAGAGTGACCCTGACCGCCGACACCAGCA CCAGCACCGCCTACATGGAGCTGAGCAGCCTGA GAAGCGAGGACACCGCCGTGTACTACTGCGGC AGATGGCTGCTGAGCGCCTGGTTCGCCTACTGG GGCCAGGGCACCCTGGTGACCGTGAGCAGCGC TAGCACCAAGGGCCCATCGGTCTTCCCCCTGGC ACCCTCCTCCAAGAGCACCTCTGGGGGCACAGC GGCCCTGGGCTGCCTGGTCAAGGACTACTTCCC CGAACCGGTGACGGTGTCGTGGAACTCAGGCG CCCTGACCAGCGGCGTGCACACCTTCCCGGCTG TCCTACAGTCCTCAGGACTCTACTCCCTCAGCA GCGTGGTGACCGTGCCCTCCAGCAGCTTGGGCA CCCAGACCTACATCTGCAACGTGAATCACAAGC CCAGCAACACCAAGGTGGACAAGAAAGTTGAG CCCAAATCTTGTGACAAAACTCACACATGCCCA CCGTGCCCAGCACCTGAACTCCTGGGGGGACCG TCAGTCTTCCTCTTCCCCCCAAAACCCAAGGAC ACCCTCATGATCTCCCGGACCCCTGAGGTCACA TGCGTGGTGGTGGACGTGAGCCACGAAGACCCT GAGGTCAAGTTCAACTGGTACGTGGACGGCGTG GAGGTGCATAATGCCAAGACAAAGCCGCGGGA GGAGCAGTACAACAGCACGTACCGTGTGGTCA GCGTCCTCACCGTCCTGCACCAGGACTGGCTGA ATGGCAAGGAGTACAAGTGCAAGGTCTCCAAC AAAGCCCTCCCAGCCCCCATCGAGAAAACCATC TCCAAAGCCAAAGGGCAGCCCCGAGAACCACA GGTGTACACCCTGCCCCCATCCCGGGATGAGTT GACCAAGAACCAGGTCAGCCTGACCTGCCTGGT CAAAGGCTTCTATCCCAGCGACATCGCCGTGGA GTGGGAGAGCAATGGGCAGCCGGAGAACAACT ACAAGACCACGCCTCCCGTGCTGGACTCCGACG GCTCCTTCTTCCTCTACAGCAAGCTCACCGTGG ACAAGAGCAGGTGGCAGCAGGGGAACGTCTTC TCATGCTCCGTGATGCATGAGGCTCTGCACAAC CACTACACGCAGAAGAGCCTCTCCCTGTCTCCG GGTAAA |
| 109 | JB94H3 hIgG1 full heavy chain nt | CAGGTGCAGCTGCAGCAGAGCGGCGCCGAGGT GAAGAAGCCCGGCGCCAGCGTGAAGCTGAGCT GCAAGGCCAGCGGCTACACCTTCACCAGCTACT GGATGCACTGGGTGAGACAGAGACCCGGCCAG GGCCTGGAGTGGATCGGCTACATCAACCCCAGC AGCGGCTACACCAAGAGCAACCAGAAGTTCAA GGACAGAGCCACCCTGACCGCCGACACCAGCA CCAGCACCGCCTACATGGAGCTGAGCAGCCTGA GAAGCGAGGACACCGCCGTGTACTACTGCGGC AGATGGCTGCTGAGCGCCTGGTTCGCCTACTGG GGCCAGGGCACCCTGGTGACCGTGAGCAGCGC TAGCACCAAGGGCCCATCGGTCTTCCCCCTGGC ACCCTCCTCCAAGAGCACCTCTGGGGGCACAGC GGCCCTGGGCTGCCTGGTCAAGGACTACTTCCC CGAACCGGTGACGGTGTCGTGGAACTCAGGCG CCCTGACCAGCGGCGTGCACACCTTCCCGGCTG TCCTACAGTCCTCAGGACTCTACTCCCTCAGCA GCGTGGTGACCGTGCCCTCCAGCAGCTTGGGCA CCCAGACCTACATCTGCAACGTGAATCACAAGC CCAGCAACACCAAGGTGGACAAGAAAGTTGAG CCCAAATCTTGTGACAAAACTCACACATGCCCA CCGTGCCCAGCACCTGAACTCCTGGGGGGACCG TCAGTCTTCCTCTTCCCCCCAAAACCCAAGGAC ACCCTCATGATCTCCCGGACCCCTGAGGTCACA TGCGTGGTGGTGGACGTGAGCCACGAAGACCCT GAGGTCAAGTTCAACTGGTACGTGGACGGCGTG GAGGTGCATAATGCCAAGACAAAGCCGCGGGA GGAGCAGTACAACAGCACGTACCGTGTGGTCA GCGTCCTCACCGTCCTGCACCAGGACTGGCTGA ATGGCAAGGAGTACAAGTGCAAGGTCTCCAAC AAAGCCCTCCCAGCCCCCATCGAGAAAACCATC TCCAAAGCCAAAGGGCAGCCCCGAGAACCACA GGTGTACACCCTGCCCCCATCCCGGGATGAGTT GACCAAGAACCAGGTCAGCCTGACCTGCCTGGT CAAAGGCTTCTATCCCAGCGACATCGCCGTGGA GTGGGAGAGCAATGGGCAGCCGGAGAACAACT ACAAGACCACGCCTCCCGTGCTGGACTCCGACG GCTCCTTCTTCCTCTACAGCAAGCTCACCGTGG ACAAGAGCAGGTGGCAGCAGGGGAACGTCTTC TCATGCTCCGTGATGCATGAGGCTCTGCACAAC CACTACACGCAGAAGAGCCTCTCCCTGTCTCCG GGTAAA |
| 110 | JB94L1 hkappa full light | GACATCCAGATGACCCAGAGCCCCAGCAGCCT GAGCGCCAGCGTGGGCGACAGAGTGACCATCA CCTGCAAGGCCAGCCAGGACATCAACACCTAC CTGAGCTGGTTCCAGCAGAAGCCCGGCAAGGC |

TABLE I-continued

Description of the antibody sequence listing of the invention

| SEQ ID NO: | Sequence Description | Sequence |
|---|---|---|
| | chain nt | CCCCAAGAGCCTGATCTACAGAAGCAACATCCT GGTGGACGGCGTGCCCAGCAGATTCAGCGGCA GCGGCAGCGGCCAGGACTTCACCCTGACCATCA GCAGCCTGCAGCCCGAGGACTTCGCCATCTACT ACTGCCTACAGTATGATGACTTTCCGTACACGT TCGGCCAGGGCACCAAGCTGGAGATCAAGCGT ACGGTGGCTGCACCATCTGTCTTCATCTTCCCGC CATCTGATGAGCAGTTGAAATCTGGAACTGCCT CTGTTGTGTGCCTGCTGAATAACTTCTATCCCAG AGAGGCCAAAGTACAGTGGAAGGTGGATAACG CCCTCCAATCGGGTAACTCCCAGGAGAGTGTCA CAGAGCAGGACAGCAAGGACAGCACCTACAGC CTCAGCAGCACCCTGACGCTGAGCAAAGCAGA CTACGAGAAACAAAGTCTACGCCTGCGAAG TCACCCATCAGGGCCTGAGCTCGCCCGTCACAA AGAGCTTCAACAGGGGAGAGTGT |
| 111 | JB94L3 hkappa full light chain nt | GACATCCAGATGACCCAGAGCCCCAGCAGCCT GAGCGCCAGCGTGGGCGACAGAGTGACCATCA CCTGCAAGGCCAGCCAGGACATCAACACCTAC CTGAGCTGGTTCCAGCAGAAGCCCGGCAAGAG CCCCAAGAGCCTGATCTACAGAAGCAACATCCT GGTGGACGGCGTGCCCAGCAGATTCAGCGGCA GCGGCAGCGGCCAGGACTACACCCTGACCATC AGCAGCCTGCAGCCCGAGGACTTCGCCATCTAC TACTGCCTACAGTATGATGACTTTCCGTACACG TTCGGCCAGGGCACCAAGCTGGAGATCAAGCG TACGGTGGCTGCACCATCTGTCTTCATCTTCCCG CCATCTGATGAGCAGTTGAAATCTGGAACTGCC TCTGTTGTGTGCCTGCTGAATAACTTCTATCCCA GAGAGGCCAAAGTACAGTGGAAGGTGGATAAC GCCCTCCAATCGGGTAACTCCCAGGAGAGTGTC ACAGAGCAGGACAGCAAGGACAGCACCTACAG CCTCAGCAGCACCCTGACGCTGAGCAAAGCAG ACTACGAGAAACAAAGTCTACGCCTGCGAA GTCACCCATCAGGGCCTGAGCTCGCCCGTCACA AAGAGCTTCAACAGGGGAGAGTGT |
| 112 | JB94H1 mIgG1 full heavy chain nt | CAGGTGCAGCTGGTGCAGAGCGGCGCCGAGGT GAAGAAGCCCGGCGCCAGCGTGAAGGTGAGCT GCAAGGCCAGCGGCTACACCTTCACCAGCTACT GGATGCACTGGGTGAGACAGGCCCCCGGCCAG GGCCTGGAGTGGATGGGCTACATCAACCCCAGC AGCGGCTACACCAAGAGCAACCAGAAGTTCAA GGACAGAGTGACCATGACCGCCGACACCAGCA CCAGCACCGCCTACATGGAGCTGAGCAGCCTGA GAAGCGAGGACACCGCCGTGTACTACTGCGGA AGATGGTTACTTTCGGCCTGGTTTGCTTACTGG GGCCAGGGCACCCTGGTGACCGTGAGCAGCGC CAAGACCACCCCTCCTTCCGTGTATCCTCTGGCT CCAGGATCCGCCGCTCAGACAAACTCCATGGTG ACCCTGGGTTGCCTGGTGAAGGGCTACTTCCCT GAGCCAGTGACCGTGACTTGGAACTCCGGCTCT CTGTCTTCCGGAGTGCACACATTTCCAGCCGTG CTGCAGAGCGACCTGTACACACTGTCCTCCTCC GTGACCGTGCCTTCTTCCACTTGGCCTTCCGAG ACCGTGACTTGCAACGTGGCCCACCCAGCCTCT TCTACCAAGGTGGACAAGAAGATCGTCCCCCGG GATTGCGGTTGCAAGCCTTGCATTTGCACCGTG CCCGAGGTGTCCTCCGTGTTCATCTTCCCTCCCA AGCCTAAGGACGTGCTGACCATCACCCTGACCC CCAAAGTGACTTGCGTGGTGGTGGACATCTCTA AGGACGACCCCGAGGTGCAGTTCTCTTGGTTCG TGGACGACGTGGAGGTGCACACAGCTCAGACA CAGCCCCGGGAGGAGCAGTTCAACTCCACCTTC CGGAGCGTGTCCGAGCTGCCCATCATGCACCAG GATTGGCTGAACGGCAAGGAGTTCAAGTGCCG CGTGAACAGCGCCGCTTTTCCAGCCCCTATCGA AGAACCATCTCCAAGACCAAGGGCAGGCCCA AGGCTCCTCAGGTGTACACCATCCCTCCCCCTA AGGAGCAGATGGCCAAGGACAAGGTGTCCCTG ACTTGCATGATCACCGACTTCTTCCCCGAGGAC ATCACAGTCGAGTGGCAGTGGAACGGCCAGCC AGCCGAGAACTACAAGAACACCCAGCCCATCA TGGATACCGACGGCTCTTACTTCGTGTACTCCA AGCTGAACGTGCAGAAGTCCAATTGGGAGGCC GGCAACACCTTCACTTGCTCCGTGCTGCACGAG GGACTGCATAACCACCACACCGAGAAGTCCCTG TCCCACTCTCCCGGCAAG |
| 113 | JB94H3 mIgG1 full heavy chain nt | CAGGTGCAGCTGCAGCAGAGCGGCGCCGAGGT GAAGAAGCCCGGCGCCAGCGTGAAGCTGAGCT GCAAGGCCAGCGGCTACACCTTCACCAGCTACT GGATGCACTGGGTGAGACAGAGACCCGGCCAG GGCCTGGAGTGGATCGGCTACATCAACCCCAGC AGCGGCTACACCAAGAGCAACCAGAAGTTCAA GGACAGAGCCACCCTGACCGCCGACACCAGCA CCAGCACCGCCTACATGGAGCTGAGCAGCCTGA GAAGCGAGGACACCGCCGTGTACTACTGCGGC AGATGGCTGCTGAGCGCCTGGTTCGCCTACTGG GGCCAGGGCACCCTGGTGACCGTGAGCAGCGC CAAGACCACCCCTCCTTCCGTGTATCCTCTGGCT CCAGGATCCGCCGCTCAGACAAACTCCATGGTG ACCCTGGGTTGCCTGGTGAAGGGCTACTTCCCT GAGCCAGTGACCGTGACTTGGAACTCCGGCTCT CTGTCTTCCGGAGTGCACACATTTCCAGCCGTG CTGCAGAGCGACCTGTACACACTGTCCTCCTCC GTGACCGTGCCTTCTTCCACTTGGCCTTCCGAG ACCGTGACTTGCAACGTGGCCCACCCAGCCTCT TCTACCAAGGTGGACAAGAAGATCGTCCCCCGG GATTGCGGTTGCAAGCCTTGCATTTGCACCGTG CCCGAGGTGTCCTCCGTGTTCATCTTCCCTCCCA AGCCTAAGGACGTGCTGACCATCACCCTGACCC CCAAAGTGACTTGCGTGGTGGTGGACATCTCTA AGGACGACCCCGAGGTGCAGTTCTCTTGGTTCG TGGACGACGTGGAGGTGCACACAGCTCAGACA CAGCCCCGGGAGGAGCAGTTCAACTCCACCTTC CGGAGCGTGTCCGAGCTGCCCATCATGCACCAG GATTGGCTGAACGGCAAGGAGTTCAAGTGCCG CGTGAACAGCGCCGCTTTTCCAGCCCCTATCGA AGAACCATCTCCAAGACCAAGGGCAGGCCCA AGGCTCCTCAGGTGTACACCATCCCTCCCCCTA AGGAGCAGATGGCCAAGGACAAGGTGTCCCTG ACTTGCATGATCACCGACTTCTTCCCCGAGGAC ATCACAGTCGAGTGGCAGTGGAACGGCCAGCC AGCCGAGAACTACAAGAACACCCAGCCCATCA TGGATACCGACGGCTCTTACTTCGTGTACTCCA AGCTGAACGTGCAGAAGTCCAATTGGGAGGCC GGCAACACCTTCACTTGCTCCGTGCTGCACGAG GGACTGCATAACCACCACACCGAGAAGTCCCTG TCCCACTCTCCCGGCAAG |
| 114 | JB94L1 mkappa full light chain nt | GACATCCAGATGACCCAGAGCCCCAGCAGCCT GAGCGCCAGCGTGGGCGACAGAGTGACCATCA CCTGCAAGGCCAGCCAGGACATCAACACCTAC CTGAGCTGGTTCCAGCAGAAGCCCGGCAAGGC CCCCAAGAGCCTGATCTACAGAAGCAACATCCT GGTGGACGGCGTGCCCAGCAGATTCAGCGGCA GCGGCAGCGGCCAGGACTTCACCCTGACCATCA GCAGCCTGCAGCCCGAGGACTTCGCCATCTACT ACTGCCTACAGTATGATGACTTTCCGTACACGT TCGGCCAGGGCACCAAGCTGGAGATCAAGAGA GCCGACGCCGCTCCTACAGTGTCTATCTTCCC CCTTCTTCCGAGCAGCTGACCTCTGGAGGAGCC TCCGTCGTGTGTTTCCTCAACAACTTCTACCCCA AGGACATCAACGTCAAGTGGAAGATCGACGGC TCCGAGAGGCAGAACGGCGTGCTGAACTCTTGG ACCGACCAGGACTCCAAGGACTCCACCTACTCC ATGTCCTCCACCCTGACCCTGACCAAGGACGAG TACGAGCGGCACAACTCCTACACTTGCGAGGCT ACCCACAAGACCTCTACCTCCCCCATCGTGAAG AGCTTCAACCGCAACGAGTGT |
| 115 | JB94L3 mkappa full | GACATCCAGATGACCCAGAGCCCCAGCAGCCT GAGCGCCAGCGTGGGCGACAGAGTGACCATCA CCTGCAAGGCCAGCCAGGACATCAACACCTAC |

TABLE I-continued

Description of the antibody sequence listing of the invention

| SEQ ID NO: | Sequence Description | Sequence |
|---|---|---|
| | light chain nt | CTGAGCTGGTTCCAGCAGAAGCCCGGCAAGAG CCCCAAGAGCCTGATCTACAGAAGCAACATCCT GGTGGACGGCGTGCCCAGCAGATTCAGCGGCA GCGGCAGCGGCCAGGACTACACCCTGACCATC AGCAGCCTGCAGCCCGAGGACTTCGCCATCTAC TACTGCCTACAGTATGATGACTTTCCGTACACG TTCGGCCAGGGCACCAAGCTGGAGATCAAGAG AGCCGACGCCGCTCCTACAGTGTCTATCTTCCC CCCCTTCTTCCGAGCAGCTGACCTCTGGAGGAGC CTCCGTCGTGTGTTTCCTCAACAACTTCTACCCC AAGGACATCAACGTCAAGTGGAAGATCGACGG CTCCGAGAGGCAGAACGGCGTGCTGAACTCTTG GACCGACCAGGACTCCAAGGACTCCACCTACTC CATGTCCTCCACCCTGACCCTGACCAAGGACGA GTACGAGCGGCACAACTCCTACACTTGCGAGGC TACCCACAAGACCTCTACCTCCCCCATCGTGAA GAGCTTCAACCGCAACGAGTGT |
| 116 | JB94H1 hIgG1mt full heavy chain nt | CAGGTGCAGCTGGTGCAGAGCGGCGCCGAGGT GAAGAAGCCCGGCGCCAGCGTGAAGGTGAGCT GCAAGGCCAGCGGCTACACCTTCACCAGCTACT GGATGCACTGGGTGAGACAGGCCCCCGGCCAG GGCCTGGAGTGGATGGGCTACATCAACCCCAGC AGCGGCTACACCAAGAGCAACCAGAAGTTCAA GGACAGAGTGACCATGACCGCCGACACCAGCA CCAGCACCGCCTACATGGAGCTGAGCAGCCTGA GAAGCGAGGACACCGCCGTGTACTACTGCGGA AGATGGTTACTTTCGGCCTGGTTTGCTTACTGG GGCCAGGGCACCCTGGTGACCGTGAGCAGCGC TAGCACAAAAGGACCTTCCGTGTTTCCTCTGGC TCCTTCTTCTAAGTCTACCAGCGGAGGAACAGC AGCTCTGGGTTGTCTGGTGAAAGATTACTTCCC AGAGCCAGTGACAGTGTCTTGGAATTCAGGAGC TCTGACATCAGGAGTGCATACATTTCCAGCAGT GCTGCAGTCTTCAGGTCTGTATTCTCTGTCCTCA GTGGTGACAGTGCCTTCTTCTTCTCTGGGAACC CAGACCTACATCTGTAACGTGAACCACAAGCCT TCCAACACCAAGGTGGATAAGAGAGTGGAGCC CAAGTCTTGCGATAAGACCCATACTTGCCCCTCC TTGTCCAGCTCCAGAATTTGAAGGAGGACCATC AGTGTTCCTGTTTCCTCCTAAGCCTAAGGACAC CCTGATGATCTCCCGGACCCCAGAAGTGACTTG TGTGGTGGTGGACGTGTCTCACGAAGATCCCGA GGTGAAGTTCAATTGGTACGTGGACGGAGTGG AAGTGCATAACGCTAAGACAAAGCCTAGAGAG GAGCAGTACAACTCCACATACAGAGTGGTGTCA GTGCTGACAGTGCTGCATCAGGATTGGCTGAAC GGAAAGGAGTACAAGTGCAAGGTGTCTAACAA GGCTCTGCCAGCTTCTATCGAGAAGACCATCTC CAAGGCTAAGGGACAGCCTAGAGAACCTCAGG TGTACACCCTGCCTCCTTCCCGGGAGGAGATGA CAAAGAACCAGGTCTCTCTGACTTGTCTGGTGA AGGGCTTTTACCCTTCCGACATCGCCGTGGAAT GGGAATCTAACGGACAGCCAGAGAACAACTAC AAGACCACACCTCCAGTGCTGGATTCCGACGGC TCCTTCTTCCTGTACTCCAAGCTGACCGTGGATA AATCTCGTTGGCAGCAGGGAAACGTGTTCTCTT GTAGCGTGATGCACGAAGCTCTGCACAATCACT ACACCCAGAAGTCCCTGTCTCTGTCTCCAGGAA AA |
| 117 | JB94H3 hIgG1mt full heavy chain nt | CAGGTGCAGCTGCAGCAGAGCGGCGCCGAGGT GAAGAAGCCCGGCGCCAGCGTGAAGCTGAGCT GCAAGGCCAGCGGCTACACCTTCACCAGCTACT GGATGCACTGGGTGAGACAGGCCCCGGCCAG GGCCTGGAGTGGATCGGCTACATCAACCCCAGC AGCGGCTACACCAAGAGCAACCAGAAGTTCAA GGACAGAGTGACCATGACCGCCGACACCAGCA CCAGCACCGCCTACATGGAGCTGAGCAGCCTGA GAAGCGAGGACACCGCCGTGTACTACTGCGGA AGATGGCTGCTGAGCGCCTGGTTCGCCTACTGG GGCCAGGGCACCCTGGTGACCGTGAGCAGCGC TAGCACAAAAGGACCTTCCGTGTTTCCTCTGGC | |

TABLE I-continued

Description of the antibody sequence listing of the invention

| SEQ ID NO: | Sequence Description | Sequence |
|---|---|---|
| | | TCCTTCTTCTAAGTCTACCAGCGGAGGAACAGC AGCTCTGGGTTGTCTGGTGAAAGATTACTTCCC AGAGCCAGTGACAGTGTCTTGGAATTCAGGAGC TCTGACATCAGGAGTGCATACATTTCCAGCAGT GCTGCAGTCTTCAGGTCTGTATTCTCTGTCCTCA GTGGTGACAGTGCCTTCTTCTTCTCTGGGAACC CAGACCTACATCTGTAACGTGAACCACAAGCCT TCCAACACCAAGGTGGATAAGAGAGTGGAGCC CAAGTCTTGCGATAAGACCCATACTTGCCCCTCC TTGTCCAGCTCCAGAATTTGAAGGAGGACCATC AGTGTTCCTGTTTCCTCCTAAGCCTAAGGACAC CCTGATGATCTCCCGGACCCCAGAAGTGACTTG TGTGGTGGTGGACGTGTCTCACGAAGATCCCGA GGTGAAGTTCAATTGGTACGTGGACGGAGTGG AAGTGCATAACGCTAAGACAAAGCCTAGAGAG GAGCAGTACAACTCCACATACAGAGTGGTGTCA GTGCTGACAGTGCTGCATCAGGATTGGCTGAAC GGAAAGGAGTACAAGTGCAAGGTGTCTAACAA GGCTCTGCCAGCTTCTATCGAGAAGACCATCTC CAAGGCTAAGGGACAGCCTAGAGAACCTCAGG TGTACACCCTGCCTCCTTCCCGGGAGGAGATGA CAAAGAACCAGGTCTCTCTGACTTGTCTGGTGA AGGGCTTTTACCCTTCCGACATCGCCGTGGAAT GGGAATCTAACGGACAGCCAGAGAACAACTAC AAGACCACACCTCCAGTGCTGGATTCCGACGGC TCCTTCTTCCTGTACTCCAAGCTGACCGTGGATA AATCTCGTTGGCAGCAGGGAAACGTGTTCTCTT GTAGCGTGATGCACGAAGCTCTGCACAATCACT ACACCCAGAAGTCCCTGTCTCTGTCTCCAGGAA AA |
| 118 | 66F2A8D6 mIgG1 full heavy chain | QVHLQQSGAELAKPGASVNLSCKASGYAFTSYW MHWVKQRPGQGLEWIGYINPSSGLAKYNQKFKD KATLTTDKSSNTAYMQLSSLTYDDSAVYYCGRW LLSAWFAYWGQGTLVTVSAAKTTPPSVYPLAPGS AAQTNSMVTLGCLVKGYFPEPVTVTWNSGSLSSG VHTFPAVLQSDLYTLSSSVTVPSSTWPSETVTCN VAHPASSTKVDKKIVPRDCGCKPCICTVPEVSSV FIFPPKPKDVLTITLTPKVTCVVVDISKDDPEVQ FSWFVDDVEVHTAQTQPREEQFNSTFRSVSELPI MHQDWLNGKEFKCRVNSAAFPAPIEKTISKTKGR PKAPQVYTIPPPKEQMAKDKVSLTCMITDFFPED ITVEWQWNGQPAENYKNTQPIMDTDGSYFVYSKL NVQKSNWEAGNTFTCSVLHEGLHNHHTEKSLSHS PGK |
| 119 | 66F2A8D6 mkappa full light chain | DIKMTQSPSSIYASLGERVTITCKASQGINTYLS WFQQKPGKSPKTLIYRANILVDGVPSRFSGSGSG QDYSLTINSLEYEDMGIYYCLQYDEFPYTFGGGT KLEIKRADAAPTVSIFPPSSEQLTSGGASVVCFL NNFYPKDINVKWKIDGSERQNGVLNSWTDQDSKD STYSMSSTLTLTKDEYERHNSYTCEATHKTSTSP IVKSFNRNEC |
| 120 | 94A12G11F2 mIgG1 full heavy chain | QVQLQQSGAELAKPGASVKLSCKASGYTFTSYW MHWVKQRPGQGLEWIGYINPSSGYTKSNQKFKD KATLTADKSSSTAYMQLSSLTYEDSAVYYCGRW LLSAWFAYWGQGTLVTVSAAKTTPPSVYPLAPGS AAQTNSMVTLGCLVKGYFPEPVTVTWNSGSLSSG VHTFPAVLQSDLYTLSSSVTVPSSTWPSETVTCN VAHPASSTKVDKKIVPRDCGCKPCICTVPEVSSV FIFPPKPKDVLTITLTPKVTCVVVDISKDDPEVQ FSWFVDDVEVHTAQTQPREEQFNSTFRSVSELPI MHQDWLNGKEFKCRVNSAAFPAPIEKTISKTKGR PKAPQVYTIPPPKEQMAKDKVSLTCMITDFFPED ITVEWQWNGQPAENYKNTQPIMDTDGSYFVYSKL NVQKSNWEAGNTFTCSVLHEGLHNHHTEKSLSHS PGK |

TABLE I-continued

Description of the antibody sequence listing of the invention

| SEQ ID NO: | Sequence Description | Sequence |
|---|---|---|
| 121 | 94A12G11F2 mkappa full light chain | DIRMTQSPSSMYASLGERVTITCKASQDINTYLS WFQQKPGKSPKSLIYRSNILVDGVPSRFSGSGSG QDYSLTISSLEYEDMGIYYCLQYDDFPYTFGGGT KLEIKRADAAPTVSIFPPSSEQLTSGGASVVCFL NNFYPKDINVKWKIDGSERQNGVLNSWTDQDSKD STYSMSSTLTLTKDEYERHNSYTCEATHKTSTSP IVKSFNRNEC |
| 122 | 191C3A8B9 mIgG1 full heavy chain | QVQLKESGPGLVAPSQSLSITCTVSGFSLTNYGV HWVRQPPGKGLEWLGVIWAGGSTNYNSALMSRLS ISKDNSKSQLFLKMNSLQADDTAMYYCARERGSS WGTMDYWGQGTSVTVSSAKTTPPSVYPLAPGSA AQTNSMVTLGCLVKGYFPEPVTVTWNSGSLSSGV HTFPAVLQSDLYTLSSSVTVPSSTWPSETVTCNV AHPASSTKVDKKIVPRDCGCKPCICTVPEVSSVF IFPPKPKDVLTITLTPKVTCVVVDISKDDPEVQF SWFVDDVEVHTAQTQPREEQFNSTFRSVSELPIM HQDWLNGKEFKCRVNSAAFPAPIEKTISKTKGRP KAPQVYTIPPPKEQMAKDKVSLTCMITDFFPEDI TVEWQWNGQPAENYKNTQPIMDTDGSYFVYSKLN VQKSNWEAGNTFTCSVLHEGLHNHHTEKSLSHSP GK |
| 123 | 191C3MB9 mkappa full light chain | QIVLTQSPAIMSASPGEKVTMTCSASSRVSYMHW YQQKSGTSPKRWIYDTSQLASGVPARFSGSGSGT SYSLTISSMEAEDAATYYCQQWSSNPYTFGGGTK LEMRRADAAPTVSIFPPSSEQLTSGGASVVCFLN NFYPKDINVKWKIDGSERQNGVLNSWTDQDSKDS TYSMSSTLTLTKDEYERHNSYTCEATHKTSTSPI VKSFNRNEC |
| 124 | JB94H1 hIgG2 full heavy chain | QVQLVQSGAEVKKPGASVKVSCKASGYTFTSYW MHWVRQAPGQGLEWMGYINPSSGYTKSNQKFK DRVTMTADTSTSTAYMELSSLRSEDTAVYYCGR WLLSAWFAYWGQGTLVTVSSASTKGPSVFPLAPC SRSTSESTAALGCLVKDYFPEPVTVSWNSGALTS GVHTFPAVLQSSGLYSLSSVVTVPSSNFGTQTYT CNVDHKPSNTKVDKTVERKCCVECPPCPAPPVAG PSVFLFPPKPKDTLMISRTPEVTCVVVDVSHEDP EVQFNWYVDGVEVHNAKTKPREEQFNSTFRVVSV LTVVHQDWLNGKEYKCKVSNKGLPAPIEKTISKT KGQPREPQVYTLPPSREEMTKNQVSLTCLVKGFY PSDIAVEWESNGQPENNYKTTPPMLDSDGSFFLY SKLTVDKSRWQQGNVFSCSVMHEALHNHYTQKSL SLSPGK |
| 125 | JB94H1 hIgG4 full heavy chain | QVQLVQSGAEVKKPGASVKVSCKASGYTFTSYW MHWVRQAPGQGLEWMGYINPSSGYTKSNQKFK DRVTMTADTSTSTAYMELSSLRSEDTAVYYCGR WLLSAWFAYWGQGTLVTVSSASTKGPSVFPLAPC SRSTSESTAALGCLVKDYFPEPVTVSWNSGALTS GVHTFPAVLQSSGLYSLSSVVTVPSSSLGTKTYT CNVDHKPSNTKVDKRVESKYGPPCPPCPAPEFLG GPSVFLFPPKPKDTLMISRTPEVTCVVVDVSQED PEVQFNWYVDGVEVHNAKTKPREEQFNSTYRVVS VLTVLHQDWLNGKEYKCKVSNKGLPSSIEKTISK AKGQPREPQVYTLPPSQEEMTKNQVSLTCLVKGF YPSDIAVEWESNGQPENNYKTTPPVLDSDGSFFL YSRLTVDKSRWQEGNVFSCSVMHEALHNYTQKS LSLSLGK |
| 126 | JB94H3 hIgG2 full heavy chain | QVQLQQSGAEVKKPGASVKLSCKASGYTFTSYW MHWVRQRPGQGLEWIGYINPSSGYTKSNQKFKD RATLTADTSTSTAYMELSSLRSEDTAVYYCGRWL LSAWFAYWGQGTLVTVSSASTKGPSVFPLAPCSR STSESTAALGCLVKDYFPEPVTVSWNSGALTSGV HTFPAVLQSSGLYSLSSVVTVPSSNFGTQTYTCN VDHKPSNTKVDKTVERKCCVECPPCPAPPVAGPS VFLFPPKPKDTLMISRTPEVTCVVVDVSHEDPEV QFNWYVDGVEVHNAKTKPREEQFNSTFRVVSVLT VVHQDWLNGKEYKCKVSNKGLPAPIEKTISKTKG QPREPQVYTLPPSREEMTKNQVSLTCLVKGFYPS DIAVEWESNGQPENNYKTTPPMLDSDGSFFLYSK LTVDKSRWQQGNVFSCSVMHEALHNHYTQKSLSL SPGK |
| 127 | JB94H3 hIgG4 full heavy chain | QVQLQQSGAEVKKPGASVKLSCKASGYTFTSYW MHWVRQRPGQGLEWIGYINPSSGYTKSNQKFKD RATLTADTSTSTAYMELSSLRSEDTAVYYCGRWL LSAWFAYWGQGTLVTVSSASTKGPSVFPLAPCSR STSESTAALGCLVKDYFPEPVTVSWNSGALTSGV HTFPAVLQSSGLYSLSSVVTVPSSSLGTKTYTCN VDHKPSNTKVDKRVESKYGPPCPPCPAPEFLGGP SVFLFPPKPKDTLMISRTPEVTCVVVDVSQEDPE VQFNWYVDGVEVHNAKTKPREEQFNSTYRVVSVL TVLHQDWLNGKEYKCKVSNKGLPSSIEKTISKAK GQPREPQVYTLPPSQEEMTKNQVSLTCLVKGFYP SDIAVEWESNGQPENNYKTTPPVLDSDGSFFLYS RLTVDKSRWQEGNVFSCSVMHEALHNHYTQKSLS LSLGK |

Notes:
Unless specified otherwise herein, all amino acid numbers are according to the EU index of the Kabat system (Kabat, E. A., et al. (1991) Sequences of Proteins of Immunological Interest, Fifth Edition, U.S. Department of Health and Human Services, NIH Publication No. 91-3242). aa: amino acid, nt: nucleotide.

DETAILED DESCRIPTION

Figure 1:
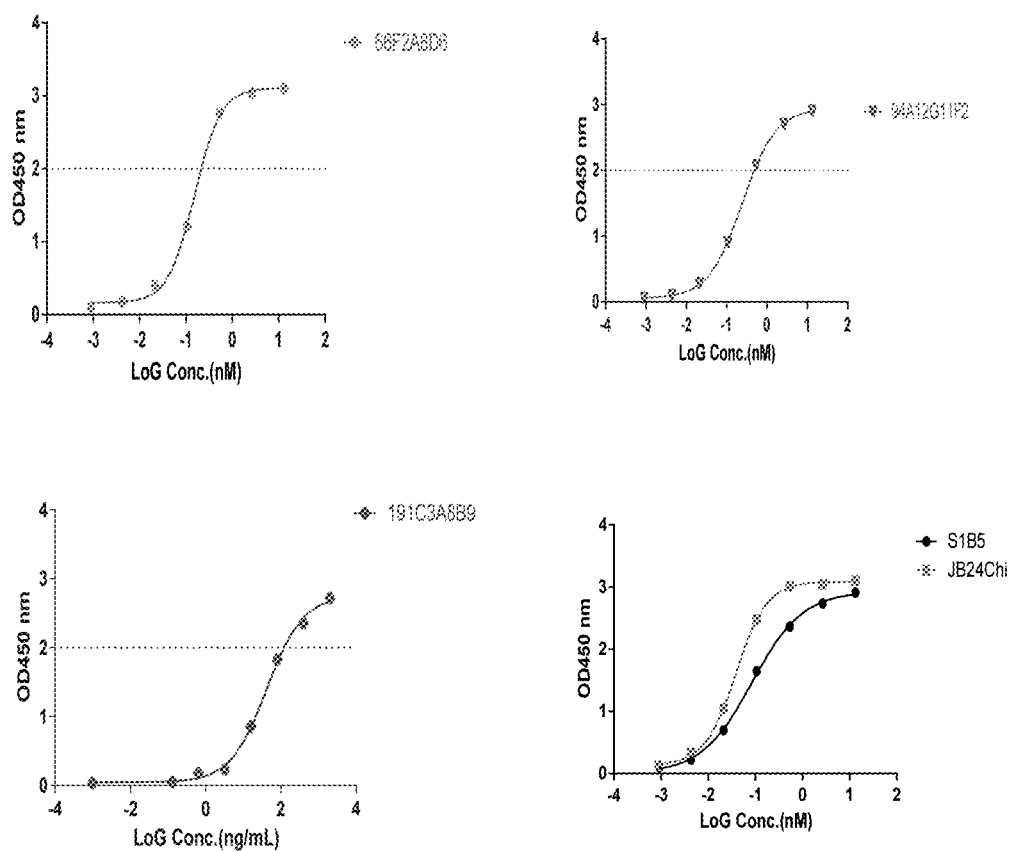
FIG. 1 shows the binding ability assay of positive clones and soluble huCD73 protein.

Described herein are isolated antibodies, particularly monoclonal antibodies, e.g., human monoclonal antibodies, which specifically bind to CD73 and thereby reduce CD73 activity ("antagonist anti-CD73 antibodies"). In certain embodiments, the antibodies described herein are derived from specific heavy and light chain germline sequences and/or comprise specific structural features such as CDR regions comprising specific amino acid sequences. Provided herein are isolated antibodies, methods of preparing such antibodies. Also provided herein are methods of using the antibodies for reducing tumor growth, alone or in combination with other therapeutic agents (e.g., antibodies) and/or cancer therapies. Accordingly, the anti-CD73 antibodies described herein may be used in a treatment of a wide variety of therapeutic applications, including, for example, inhibition of tumor growth, inhibition of metastasis, and enhancement of an immune response against a tumor.

Definitions

In order that the present description may be more readily understood, certain terms are firstly defined. Additional definitions are set forth throughout the detailed description.

The term "Cluster of Differentiation 73" or "CD73" as used herein refers to an enzyme (nucleotidase) capable of converting extracellular nucleoside 5' monophosphates to nucleosides, namely converting adenosine monophosphate (AMP) to adenosine. CD73 is usually found as a dimer anchored to the cell membrane through a glycosylphosphatidylinositol (GPI) bond, has ecto-enzyme activity and plays a role in signal transduction. The primary function of CD73 is converting extracellular nucleotides (e.g., 5'-AMP) to adenosine, which is a highly immunosuppressive molecule. Thus, ecto-5'-nucleotidase catalyzes the dephosphorylation of purine and pyrimidine ribo- and deoxyribonulceoside monophosphates to the corresponding nucleoside. Although CD73 has broad substrate specificity, it prefers purine ribonucleosides.

CD73 is also referred to as ecto-5'nuclease (ecto-5'NT, EC 3.1.3.5). The term "CD73" includes any variants or isoforms of CD73 which are naturally expressed by cells. Accordingly, antibodies described herein may cross-react with CD73 from species other than human (e.g., cynomolgus CD73). Alternatively, the antibodies may be specific for human CD73 and may not exhibit any cross-reactivity with other species. CD73 or any variants and isoforms thereof, may either be isolated from cells or tissues which naturally express them or be recombinantly produced using well-known techniques in the art and/or those described herein.

Two isoforms of human CD73 have been identified, both of which share the same N-terminal and C-terminal portions. Isoform 1 (Accession No. NP 002517.1; SEQ ID NO: 1) represents the longest protein, consisting of 574 amino acids and 9 exons. Isoform 2 (Accession No. NP 001191742.1) encodes a shorter protein, consisting of 524 amino acids, lacking amino acids 404-453. Isoform 2 lacks an alternate in-frame exon, resulting in a transcript with only 8 exons, but with the same N- and C-terminal sequences.

The cynomolgus (cyno) CD73 protein sequence is provided as SEQ ID NO: 2. The terms cynomolgus and cyno both refer to the *Macaca fascicularis* species and are used interchangeably throughout the description.

The term "antibody" as used herein may include whole antibodies and any antigen binding fragments (i.e., "antigen-binding portions") or single chains thereof. An "antibody" refers, in one embodiment, to a glycoprotein or an antigen binding portion thereof comprising at least two heavy (H) chains and two light (L) chains inter-connected by disulfide bonds. Each heavy chain is comprised of a heavy chain variable region (abbreviated herein as VH) and a heavy chain constant region. In some certain naturally occurring IgG, IgD and IgA antibodies, the heavy chain constant region is comprised of three domains, CH1, CH2 and CH3. In some certain naturally occurring antibodies, each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), and regions that are more conserved, termed framework regions (FR), both of which are intermingled arrangement. Herein, the CDRs of the VH region are abbreviated as HCDR, that is, the three CDRs of the VH region can be abbreviated as HCDR1, HCDR2, and HCDR3; the CDRs of the VL region are abbreviated as LCDR, that is, the three CDRs of the VL region can be abbreviated as LCDR1, LCDR2. LCDR3. Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system (C1q).

The heavy chain of an antibody may or may not contain a terminal lysine (K), or a terminal glycine and lysine (GK). Thus, any of the heavy chain sequences and heavy chain constant region sequences provided herein can end in either GK or G[ob1], or lack K or GK, regardless of what the last amino acid of the sequence provides. This is because the terminal lysine and sometimes glycine and lysine are cleaved during expression of the antibody.

Antibodies typically bind specifically to their cognate antigen with high affinity, reflected by a dissociation constant ($K_D$) of $10^{-7}$ to $10^{-11}$M or less. Any $K_D$ greater than about $10^{-6}$ M is generally considered to indicate binding nonspecifically. As used herein, an antibody that "binds specifically" to an antigen refers to an antibody that binds to the antigen and substantially identical antigens with high affinity, which means having a $K_D$ of $10^{-7}$M or less, preferably $10^{-8}$M or less, even more preferably $5\times10^{-9}$M or less, and most preferably between $10^{-8}$M and $10^{-10}$M or less, but does not bind with high affinity to unrelated antigens. An antigen is "substantially identical" to a given antigen if it exhibits a high degree of sequence identity to the given antigen, for example, if it exhibits at least 80%, at least 90%, at least 95%, at least 97%, or at least 99% or greater sequence identity to the sequence of the given antigen. By way of example, an antibody that binds specifically to human CD73 may also cross-react with CD73 from some non-human primate species (e.g., cynomolgus), but may not cross-react with CD73 from other species, or with an antigen other than CD73.

An immunoglobulin may be from any of the commonly known isotypes, including but not limited to IgA, secretory IgA, IgG and IgM. The IgG isotype is divided in subclasses in some species: IgG1, IgG2, IgG3 and IgG4 in humans, and IgG1, IgG2a, IgG2b and IgG3 in mice. In certain embodiments, the anti-CD73 antibodies described herein are of the human IgG1 or IgG2 subtype. Immunoglobulins, e.g., human IgG1, exist in several allotypes, which differ from each other in at most a few amino acids. "Antibody" may include, by way of example, both naturally occurring and non-naturally occurring antibodies; monoclonal and polyclonal antibodies; chimeric and humanized antibodies; human and nonhuman antibodies; wholly synthetic antibodies; and single chain antibodies.

The term "antigen-binding portion" of an antibody, as used herein, refers to one or more fragments of an antibody that retain the ability to specifically bind to an antigen (e.g., human CD73). It has been shown that the antigen-binding function of an antibody can be performed by fragments of a full-length antibody. Examples of binding fragments encompassed within the term "antigen-binding portion" of an antibody, e.g., an anti-CD73 antibody described herein, include (i) a Fab fragment, which is a monovalent fragment consisting of the VL, VH, CL and CH1 domains; (ii) a F(ab')2 fragment, which is a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) or (vii) a combination of two or more isolated CDRs which may optionally be linked by a synthetic linker. Furthermore, although the two domains of the Fv fragment, VL and VH, are encoded by different genes, they can be linked, using recombinant methods, by a synthetic linker that enables them to be made as a single protein chain in which the VL and VH regions pair to form monovalent molecules known as single chain Fv (scFv); see e.g., Bird et al. (1988) Science 242:423-426; and Huston et al. (1988) *Proc. Natl. Acad. Sci. USA* 85:5879-5883). Such single chain antibodies are also intended to be encompassed within the term "antigen-binding portion" of an antibody. These and other potential constructs are described at Chan & Carter (2010) *Nat. Rev. Immunol.* 10:301. These antibody fragments are obtained using conventional techniques known to those with skill in the art, and the fragments are screened for utility in the same manner as intact antibodies. Antigen-binding portions can be produced by recombinant DNA techniques, or by enzymatic or chemical cleavage of intact immunoglobulins.

The term "amino acid sequence of conservative modifications form" refers to the amino acid modifications that do not significantly affect or alter the binding characteristics of the antibody containing the amino acid sequence, and the modifications include amino acid substitutions, additions and deletions. Modifications can be introduced into an antibody of the invention by standard techniques, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function using the functional assays described herein. Preferably, the conservative modifications are no more than one or two in number.

A "bispecific" or "bifunctional antibody" is an artificial hybrid antibody having two different heavy/light chain pairs, giving rise to two antigen binding sites with specificity for different antigens. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

The term "monoclonal antibody," as used herein, refers to an antibody that displays a single binding specificity and affinity for a specific epitope or a composition of antibodies in which all antibodies display a single binding specificity and affinity for a specific epitope. Typically such monoclonal antibodies will be derived from a single antibody encoding cell or nucleic acid, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell derived from a transgenic or transchromosomal non-human animal (e.g., a transgenic mouse having a genome comprising a human heavy chain transgene and a light chain transgene), with an immortalized cell.

The term "recombinant human antibody," as used herein, includes all human antibodies that are prepared, expressed, produced or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, produced or isolated by any other means that involve splicing of human immunoglobulin gene sequences to other DNA sequences. Such recombinant human antibodies comprise variable and constant regions that utilize specific human germline immunoglobulin sequences and are encoded by the germline genes, but include subsequent rearrangements and mutations that occur, for example, during antibody maturation. As known in the art (see, e.g., Lonberg (2005) Nature Biotech. 23(9): 1117-1125), the variable region contains the antigen binding domain, which is encoded by various genes that rearrange to form an antibody specific for a exogenous antigen. In addition to rearrangement, the variable region can be further modified by multiple single amino acid changes (referred to as somatic mutation or hypermutation) to increase the affinity of the antibody to the exogenous antigen. The constant region will change in further response to an antigen (i.e., isotype switch). Therefore, the rearranged and somatically mutated nucleic acid sequences that encode the light chain and heavy chain immunoglobulin polypeptides in response to an antigen may not be identical to the original germline sequences, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region is also derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody are replaced with corresponding amino acids derived from human immunoglobulins. In one embodiment of an antibody in humanized form, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a specific antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

A "modified heavy chain constant region" refers to a heavy chain constant region comprising the constant domains CH1, hinge, CH2, and CH3, wherein one or more of the constant domains are from a different isotype (e.g. IgG1, IgG2, IgG3, IgG4). In some embodiments, the modified constant region includes a human IgG2 CH1 domain and a human IgG2 hinge fused to a human IgG1 CH2 domain and a human IgG1 CH3 domain. In certain embodiments, such modified constant regions also include amino acid modifications within one or more of the domains relative to the wildtype amino acid sequence.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants in a specific isotype group, which variants differ in a few amino acids (see, e.g., Jefferis et al. (2009) mAbs 1: 1). Antibodies described herein may be of any allotype.

Unless specified otherwise herein, all amino acid numbers are according to the EU index of the Kabat system (Kabat, E. A., et al. (1991) Sequences of Proteins of Immunological Interest, Fifth Edition, U.S. Department of Health and Human Services, NIH Publication No. 91-3242).

The terms "an antibody recognizing an antigen" and "an antibody specific for an antigen" are used interchangeably herein with the term "an antibody which binds specifically to an antigen."

The term "an isolated antibody," as used herein, is intended to refer to an antibody that is substantially free of other antibodies having different antigenic specificities (e.g., an isolated antibody that specifically binds to CD73 is substantially free of antibodies that specifically bind antigens other than CD73). An isolated antibody that specifically binds to an epitope of CD73 may, however, have cross-reactivity to other CD73 proteins from different species.

As used herein, an antibody that "inhibits CD73" refers to an antibody that inhibits a biological and/or enzymatic function of CD73. These functions include, for example, the ability of an antibody to inhibit CD73 enzymatic activity, e.g., CD73-regulated production of adenosine or reduction of cAMP production.

As used herein, an antibody that "internalizes" refers to an antibody that crosses the cell membrane upon binding to a cell-surface antigen. Internalization includes antibody mediated receptor, e.g., CD73, internalization. In some embodiments, the antibody "internalizes" into cells expressing CD73 at a rate of $T_{1/2}$ equal to about 10 min or less.

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated hagocytosis (ADCP), and downregulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating receptors (FcγRI, FcγRIII, and FcγRIV in mice; FcγRIA, FcγRIIA, and FcγRIIIA in humans) and one inhibitory receptor (FcγRIIB). Various properties of human FcγRs are summarized in Table A. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but does not express the inhibitory FcγRIIB in mice and humans. Human IgG1 binds to most human Fc receptors and is considered that the types of activating Fc receptors which it binds to are equivalent to murine IgG2a.

TABLE A

Characteristics of human FcγRs

| Fcγ | Allelic variants | Affinity for human IgG | Isotype preference | Cellular distribution |
|---|---|---|---|---|
| FcγRI | None described | High ($K_D$~ 10 nM) | IgG1 = 3 > 4 >> 2 | Monocytes, macrophages, activated neutrophils, dentritic cells |
| FcγRIIA | H131 | Low to medium | IgG1 > 3 > 2 > 4 | Neutrophils, monocytes, macrophages, eosinophils, |
|  | R131 | Low | IgG1 > 3 > 4 > 2 | dentritic cells, platelets |
| FcγRIIIA | V158 | Medium | IgG1 = 3 >> 4 > 2 | NK cell, monocytes, |
|  | F158 | Low | IgG1 = 3 >> 4 > 2 | macrophages, mast cells, eosinophils, dentritic cell |
| FcγRIIB | I232 | Low | IgG1 = 3 = 4 > 2 | B cells, monocytes, |
|  | T232 | Low | IgG1 = 3 = 4 > 2 | macrophages, dentritic cells, mast cells |

A "hinge", "hinge domain" or "hinge region" or "antibody hinge region" refers to the domain of a heavy chain constant region that links the CH1 domain to the CH2 domain and includes the upper, middle, and lower portions of the hinge (Roux et al. J. Immunol. 1998 161:4083). The hinge provides varying levels of flexibility between the binding and effector regions of an antibody and also provides sites for intermolecular disulfide bonding between the two heavy chain constant regions. The term "hinge" includes wildtype hinges, as well as variants thereof (e.g., non-naturally-occurring hinges or modified hinges). For example, the term "IgG2 hinge" includes wildtype IgG2 hinge, and variants having 1, 2, 3, 4, 5, 1-3, 1-5, 3-5 and/or at most 5, 4, 3, 2, or 1 mutations, e.g., substitutions, deletions or additions.

The term "CH1 domain" refers to the heavy chain constant region linking the variable domain to the hinge in a heavy chain constant domain. The term "CH1 domain" includes wildtype CH1 domains, as well as variants thereof (e.g., non-naturally-occurring CH1 domains or modified CH1 domains). For example, the term "CH1 domain" includes wildtype CH1 domains and variants thereof having 1, 2, 3, 4, 5, 1-3, 1-5, 3-5 and/or at most 5, 4, 3, 2, or 1 mutations, e.g., substitutions, deletions or additions. Exemplary CH1 domains include CH1 domains with mutations that change a biological activity of an antibody, such as ADCC, CDC or half-life period. Modifications to the CH1 domain that affect a biological activity of an antibody are provided herein.

The term "CH2 domain" refers to the heavy chain constant region linking the hinge in a heavy chain constant domain to the CH3 domain. The term "CH2 domain" includes wildtype CH2 domains, as well as variants thereof (e.g., non-naturally-occurring CH2 domains or modified CH2 domains). For example, the term "CH2 domain" includes wildtype CH2 domains and variants thereof having 1, 2, 3, 4, 5, 1-3, 1-5, 3-5 and/or at most 5, 4, 3, 2, or 1 mutations, e.g., substitutions, deletions or additions. Exemplary CH2 domains include CH2 domains with mutations that change a biological activity of an antibody, such as ADCC, CDC or half-life.

The term "CH3 domain" refers to the heavy chain constant region that is C-terminal to the CH2 domain in a heavy chain constant domain. The term "CH3 domain" includes wildtype CH3 domains, as well as variants thereof (e.g., non-naturally-occurring CH3 domains or modified CH3 domains). For example, the term "CH3 domain" includes wildtype CH3 domains and variants thereof having 1, 2, 3, 4, 5, 1-3, 1-5, 3-5 and/or at most 5, 4, 3, 2, or 1 mutations, e.g., substitutions, deletions or additions. Exemplary CH3 domains include CH3 domains with mutations that change a biological activity of an antibody, such as ADCC, CDC or half-life. Modifications to the CH3 domain that affect a biological activity of an antibody are provided herein.

A "CL domain" refers to the constant domain of a light chain. The term "CL domain" includes wildtype CL domains and variants thereof.

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc includes the various allotypes of Fcs (see, e.g., Jefferis et al. (2009) mAbs 1: 1).

The term "epitope" or "antigenic determinant" refers to a site on an antigen (e.g., CD73) to which an immunoglobulin or antibody specifically binds. Epitopes within protein antigens can be formed both from contiguous amino acids (usually a linear epitope) or noncontiguous amino acids juxtaposed by tertiary folding of the protein (usually a conformational epitope). Epitopes formed from contiguous amino acids are typically, but not always, retained when exposing to denaturing solvents, whereas epitopes formed by tertiary folding are typically lost when treating with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation analysis, wherein overlapping or contiguous peptides (e.g., from CD73) are tested for reactivity with a given antibody (e.g., anti-CD73 antibody). Methods of determining spatial conformation of epitopes include techniques in the art and those described herein, for example, x-ray crystallography, 2-dimensional nuclear magnetic resonance and HDX-MS (see, e.g., Epitope Mapping Protocols in Methods in Molecular Biology, Vol. 66, G. E. Morris, Ed. (1996)).

The term "epitope mapping" refers to the process of identification of the molecular determinants on the antigen involved in antibody-antigen recognition.

The term "binds to the same epitope" with reference to two or more antibodies means that the antibodies bind to the same segment of amino acid residues, as determined by a given method. Techniques for determining whether antibodies bind to the "same epitope on CD73" of the antibodies described herein include, for example, epitope mapping methods, such as, x-ray analyses of crystals of antigen: antibody complexes, which provide atomic resolution of the epitope, and hydrogen/deuterium exchange mass spectrometry (HDX-MS). Other methods that monitor the binding of the antibody to antigen fragments (e.g. proteolytic fragments) or to mutated variations of the antigen where loss of binding due to a modification of an amino acid residue in the antigen sequence is often considered an indication of an epitope component (e.g. alanine scanning mutagenesis—Cunningham & Wells (1985) Science 244: 1081). In addition, computational combinatorial methods for epitope mapping can also be used. These methods rely on the ability of the antibody of interest from combinatorial phage display peptide libraries to affinity isolate specific short peptides.

Antibodies that "compete with another antibody for binding to a target" refer to antibodies that inhibit (partially or completely inhibit) the binding of another antibody to the target. Whether the two antibodies compete with each other for binding to a target, i.e., whether and to what extent one antibody inhibits the binding of another antibody to a target, may be determined using known competition experiments, such as those described in the Examples. In certain embodiments, an antibody competes with another antibody, and inhibit at least 10%, 20%, 30%, 40%, 50%, 60%, 70%, 80%, 90% or 100% of the binding. The extent of inhibition or competition may be different depending on which antibody is the "blocking antibody" (i.e., the cold antibody that is incubated first with the target). Competition assays can be conducted as described, for example, in Ed Harlow and David Lane, Cold Spring Harb Pro toe; 2006; doi: 10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, the overlapping epitope or the adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich analysis (see Harlow and Lane, Antibodies: A Laboratory Manual, Cold Spring Harbor Press (1988)); solid phase direct label RIA using I-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)).

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$M, such as approximately less than $10^{-8}$M, $10^{-9}$M or $10^{-10}$M or even lower when determined by, e.g., surface plasmon resonance (SPR) technology in a BIACORE® 2000 surface plasmon resonance instrument using the predetermined antigen, e.g., recombinant human CD73, as the analyte and the antibody as the ligand, or Scatchard analysis of binding of the antibody to antigen positive cells, and (ii) binds to the predetermined antigen with an affinity that is at least two-times greater than its affinity for binding to a non-specific antigen (e.g., BSA, casein) other than the predetermined antigen or a closely-related antigen. Accordingly, unless otherwise indicated, an antibody that "specifically binds to human CD73" refers to an antibody that binds to soluble or cell bound human CD73 with a $K_D$ of $10^{-7}$M or less, such as approximately less than $10^{-8}$M, $10^{-9}$M or $10^{-10}$M or even lower. An antibody that "cross-reacts with cynomolgus CD73" refers to an antibody that binds to cynomolgus CD73 with a $K_D$ of $10^{-7}$M or less, such as less than $10^{-8}$M, $10^{-9}$M or $10^{-10}$M or even lower. In certain embodiments, antibodies that do not cross-react with CD73 from a non-human species exhibit essentially undetectable binding against these proteins in standard binding assays.

The term "Kassoc" or "Ka", as used herein, is intended to refer to the association rate constant of a specific antibody-antigen interaction, whereas the term "Kdis" or "Kd" as used herein, is intended to refer to the dissociation rate constant of a specific antibody-antigen interaction. The term "$K_D$", as used herein, is intended to refer to the equilibrium dissociation constant, which is obtained from the ratio of Kd to Ka (i.e., Kd/Ka) and is expressed as a molar concentration (M). $K_D$ values of antibodies can be determined using methods well established in the art. A preferred method for determining the $K_D$ of an antibody is to analyze by using surface plasmon resonance, preferably using a biosensor system such as a Biacore® surface plasmon resonance system or flow cytometry and Scatchard.

The term "EC50" in the context of an in vitro or in vivo assay using an antibody or antigen binding fragment thereof refers to the concentration of an antibody or an antigen-binding portion thereof that induces a response that is 50% of the maximal response, i.e., halfway between the maximal response and the baseline.

A "rate of internalization" of an antibody or of a receptor, e.g., CD73, as mediated by the antibody, e.g., an anti-CD73 antibody, may be represented, e.g., by $T_{1/2}$ of internalization, e.g., as shown in the Examples. A rate of internalization of an anti-CD73 antibody may be enhanced or increased by at least 10%, 30%, 50%, 75%, 2 times, 3 times, 5 times or more, resulting in a reduction of the $T_{1/2}$ by at least 10%, 30%, 50%, 75%, 2 times, 3 times, 5 times or more by changing the heavy chain constant region of the antibody to a modified heavy chain constant region, e.g., one that contains an IgG2 hinge and IgG2 CH1 domain. For example, instead of having a $T_{1/2}$ of 10 minutes, a modified heavy chain constant region may increase the rate of internalization and thereby reduce the $T_{1/2}$ to 5 minutes (i.e., a two times increase in rate of internalization or a two times decrease in $T_{1/2}$). "$T_{1/2}$" is defined as the time at which half of the maximal internalization is achieved, as measured from the time that the antibody is added to the cells. The maximal level of internalization can be the level of internalization at the plateau of a graph representing the internalization plotted against antibody concentrations. A modified heavy chain constant region may increase the maximal level of internalization of an antibody by at least 10%, 30%, 50%, 75%, 2 times, 3 times, 5 times or more. Another way of comparing internalization efficacies of different antibodies, such as an antibody with, and the same antibody without, a modified heavy chain constant region, is by comparing their level of internalization at a given antibody concentration (e.g., 100 nM) or at a given time (e.g., 2 minutes, 5 minutes, 10 minutes or 30 minutes). Comparing levels of internalization can also be done by comparing the EC50 levels of internalization.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or a disulfide bond. A "protein" may comprise one or more polypeptides.

The term "nucleic acid molecule," as used herein, is intended to include DNA molecules and RNA molecules. A nucleic acid molecule may be a single chain or a double chain, and may be cDNA. Also provided are "conservative sequence modifications" of the sequences set forth in SEQ ID NOs described herein, i.e., nucleotide and amino acid sequence modifications which do not abrogate the binding of the antibody encoded by the nucleotide sequence or containing the amino acid sequence to the antigen. Such conservative sequence modifications include conservative nucleotide and amino acid substitutions, as well as, nucleotide and amino acid additions and deletions. For example, modifications can be introduced into SEQ ID NOs described herein by standard techniques known in the art, such as site-directed mutagenesis and PCR-mediated mutagenesis. Conservative sequence modifications include conservative amino acid substitutions, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-CD73 antibody is preferably replaced with another amino acid residue from the same side chain family. Methods of identifying nucleotide and amino acid conservative substitutions that do not eliminate antigen binding are well-known in the art (see, e.g., Brummell et al., Biochem. 32: 1180-1187 (1993); Kobayashi et al. Protein Eng. 12(10): 879-884 (1999); and Burks et al. Proc. Natl. Acad. Sci. USA 94:412-417 (1997)). Alternatively, in another embodiment, mutations can be introduced randomly along all or part of an anti-CD73 antibody encoding sequence, such as by saturation mutagenesis, and the resulting modified anti-CD73 antibodies can be screened through improved binding activity.

For nucleic acids, the term "substantial identity" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial identity exists when the segments will hybridize under selective hybridization conditions, to the complement of the chain.

For polypeptides, the term "substantial identity" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The identity % between two sequences is a function of the number of identical positions shared by the sequences when the sequences are optimally aligned (i.e., identity %=number of identical positions/total number of positions×100), with optimal alignment determined taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the algorithm of Needleman and Wunsch (J. Mol. Biol. (48): 444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform searches against public databases to, for example, identify related sequences. Such searches can be performed with the NBLAST and) (BLAST programs (version 2.0) of Altschul, et al. (1990) J. Mol. Biol. 215:403-10. BLAST nucleotide searches can be performed with the NBLAST program, score=100, wordlength=12 to obtain nucleotide sequences identical to the nucleic acid molecules described herein. BLAST protein searches can be performed with the) (BLAST program, score=50, wordlength=3 to obtain amino acid sequences identical to the protein molecules described herein. To obtain gapped alignments for comparison purposes, Gapped BLAST can be used as described in Altschul et al., (1997) Nucleic Acids Res. 25(17):3389-3402. When using BLAST and Gapped BLAST programs, the default parameters of the respective programs (e.g., XBLAST and NBLAST) can be used. See www.ncbi.nlm.nih.gov.

These nucleic acids may be present in whole cells, in a cell lysate, or in a partially purified or substantially pure form. The nucleic acid is "isolated" or "rendered substantially pure" when purified away from other cellular components or other contaminants, e.g., other cellular nucleic acids (e.g., the other parts of the chromosome) or proteins, by standard techniques including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, may be mutated in accordance with standard techniques to provide gene sequences. For encoding sequences, these mutations may affect amino acid sequence as desired. Specifically, DNA sequences substantially identical to or derived from native V, D, J, constant, switches and other such sequences described herein are contemplated.

The term "vector," as used herein, is intended to refer to a nucleic acid molecule capable of transporting another nucleic acid to which it has been linked. One type of vector is "plasmid," which refers to a circular double chains DNA loop into which other DNA segments may be linked. Another type of vector is viral vector, wherein other DNA segments may be linked into the viral genome. Some vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell when introduced into the host cell, and thereby are replicated along with the host genome. Moreover, some vectors are capable of directing the expression of genes to which they are operatively linked. Such vectors are referred to herein as "recombinant expression vectors" (or simply, "expression vectors"). In general, expression vectors used in recombinant DNA techniques are often in the form of plasmids. In the present description, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and may be a cell into which a recombinant expression vector has been introduced. It should be understood that such terms are intended to refer not only to the specific subject cell but to the progeny of such a cell. Since certain modifications may occur in succeeding generations due to either mutation or environmental influences, such progeny may not, in fact, be identical to the parent cell, but are still included within the scope of the term "host cell" as used herein.

As used herein, the term "antigen" refers to any natural or synthetic immunogenic substance, such as a protein, peptide, or hapten. An antigen may be CD73 or a fragment thereof.

An "immune response" refers to a biological response in a vertebrate for exogenous agents, such response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement), the action results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune response or reaction includes, e.g., activation or inhibition of a T cell, e.g., an effector T cell or a Th cell, such as a CD4+ or CD8+ T cell, or inhibition of a Treg cell.

An "immunomodulator" or "immunoregulator" refers to an agent, e.g., a component of a signaling pathway, which may be involved in modulating, regulating, or modifying an immune response. "Modulating," "regulating," or "modifying" an immune response refers to any changes in a cell of the immune system or in the activity of such cell (e.g., an effector T cell). Such modulation includes stimulation or suppression of the immune system which may be manifested by an increase or decrease in the number of various cell types, an increase or decrease in the activity of these cells, or any other changes which can occur within the immune system. Both inhibitory and stimulatory immunomodulators have been identified, some of which may have enhanced function in a tumor microenvironment. The immunomodulator may be located on the surface of a T cell. An "immunomodulatory target" or "immunoregulatory target" is an immunomodulator that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

An increased ability of stimulating an immune response, or the immune system can result from an enhanced agonist activity of T cell co-stimulatory receptors and/or an enhanced antagonist activity of inhibitory receptors. An increased ability of stimulating an immune response or the immune system may be reflected by a time increase of the EC50 or maximal level of activity in an assay that measures an immune response, e.g., an assay that measures changes in cytokine or chemokine release, cytolytic activity (determined directly on target cells or indirectly via detecting CD 107a or granzymes) and proliferation. The ability of stimulating an immune response or the immune system activity may be enhanced by at least 10%, 30%, 50%, 75%, 2 times, 3 times, 5 times or more.

"Immunotherapy" refers to the treatment of a subject afflicted with, or at risk of contracting or suffering a recurrence of, a disease by a method comprising inducing, enhancing, suppressing or otherwise modifying an immune response.

"Immuno stimulating therapy" or "immuno stimulatory therapy" refers to a therapy that results in increasing (inducing or enhancing) an immune response in a subject for, e.g., treating cancer.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

"T effector" ("Teff") cells refers to T cells (e.g., CD4+ and CD8+ T cells) as well as T helper (Th) cells with cytolytic activities, which secrete cytokines and activate and direct other immune cells, but does not include regulatory T cells (Treg cells).

As used herein, the term "linkage" refers to the association of two or more molecules. The linkage can be covalent or non-covalent. The linkage also can be genetic (i.e., recombinantly fused). Such linkages can be achieved using a wide variety of art recognized techniques, such as chemical coupling and recombinant protein production.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, but not limited, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the term "T cell-mediated response" refers to a response mediated by T cells, including effector T cells (e.g., CD8+ cells) and helper T cells (e.g., CD4+ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by CD8+ T cells.

As used herein, the terms "inhibition" or "blocking" (e.g., referring to inhibition/blocking of CD73 binding or activity) are used interchangeably and encompass both partial and complete inhibition/blocking.

As used herein, "cancer" refers a broad group of diseases characterized by the uncontrolled growth of abnormal cells in the body. Since unregulated cell division may result in the formation of malignant tumors or cells, they would invade neighboring tissues and may metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Prophylaxis refers to administration to a subject who does not have a disease, to prevent the disease from occurring or minimize its effects if it does.

A "hematological malignancy" includes lymphoma, leukemia, myeloma or lymphoid malignancy, as well as cancers of the spleen and lymph nodes. Exemplary lymphomas include both B cell lymphomas and T cell lymphomas. B-cell lymphomas include both Hodgkin's lymphomas and most non-Hodgkin's lymphomas. Non-limiting examples of B cell lymphomas include diffuse large B-cell lymphoma, follicular lymphoma, mucosa-associated lymphatic tissue lymphoma, small cell lymphocytic lymphoma (overlaps with chronic lymphocytic leukemia), mantle cell lymphoma (MCL), Burkitt's lymphoma, mediastinal large B cell lymphoma, Waldenstrom macroglobulinemia, nodal marginal zone B cell lymphoma, splenic marginal zone lymphoma, intravascular large B-cell lymphoma, primary effusion lymphoma, lymphomatoid granulomatosis. Non-limiting examples of T cell lymphomas include extranodal T cell lymphoma, cutaneous T cell lymphomas, anaplastic large cell lymphoma, and angioimmunoblastic T cell lymphoma. Hematological malignancies also include leukemia, such as, but not limited to, secondary leukemia, chronic lymphocytic leukemia, acute myelogenous leukemia, chronic myelogenous leukemia, and acute lymphoblastic leukemia. Hematological malignancies further include myelomas, such as, but not limited to, multiple myeloma and smoldering multiple myeloma. Other hematological and/or B cell- or T-cell-related cancers are encompassed by the term hematological malignancy.

The term "effective dose" or "effective dosage" is defined as an amount sufficient to achieve or at least partially achieve a desired effect. A "therapeutically effective dose" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective dose" or a "prophylactically effective dosage" of a drug is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to those skilled in the art, such as in human subjects during clinical trials, in animal model systems predictive of efficacy in humans, or by assaying the activity of the agent in in-vitro assays.

By way of example, an anti-cancer agent is a drug that slows cancer progression or promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms. Pharmacological effectiveness refers to the ability of the drug to promote cancer regression in the patient. Physiological safety refers to an acceptably low level of toxicity, or other adverse physiological effects at the cellular, organ and/or organism level (adverse effects) resulting from administration of the drug.

By way of example, for the treatment of tumors, a therapeutically effective dose or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective dose or dosage of the drug completely inhibits cell growth or tumor growth, i.e., preferably inhibits cell growth or tumor growth by 100%. The ability of a compound to inhibit tumor growth can be evaluated using the assays described infra. Alternatively, this characteristic of a composition can be evaluated by examining the ability of the compound to inhibit cell growth, such inhibition can be measured in vitro by assays known to the skilled practitioner. In other preferred embodiments described herein, tumor regression may be observed and may continue for a period of at least about 20 days, more preferably at least about 40 days, or even more preferably at least about 60 days.

The terms "patient" and "subject" refer to any human or non-human animal that receives either prophylactic or therapeutic treatment. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

"Pharmaceutically acceptable" is intended to refer to the substance or composition that must be chemically and/or toxicologically compatible with the other ingredients comprising the formulation and/or the mammal being treated with it.

"Pharmaceutically acceptable vectors" encompasses pharmaceutically acceptable vectors, excipients, and diluents, and is intended to refer to materials, compositions, or vehicles that involve carrying or transporting pharmaceutical agents from one organ or body part of a subject to another organ or body part of a subject, such as liquid or solid fillers, diluents, excipients, solvents or encapsulating materials.

EXAMPLES

Example 1: Screening and Identification of Anti-CD73 Antibodies

C57/BL6 mice were immunized with human CD73 ectodomain recombinant protein (huCD73, SEQ ID NO: 1). Performing the first immunization (intraperitoneal injection) with an emulsion of 50 µg huCD73 protein plus Freund's complete adjuvant, performing the second immunization (subcutaneous injection) with an emulsion of 25 huCD73 protein plus incomplete Freund's adjuvant, performing the third immunization (intraperitoneal injection) with an emulsion of 25 µg huCD73 protein plus incomplete Freund's adjuvant, performing the fourth immunization (subcutaneous injection) with an emulsion of 25 µg huCD73 protein plus incomplete Freund's adjuvant, and finally, performing the final boost immunization (intraperitoneal injection) with 50 µg huCD73 protein. Four days after the boost, the immune spleen cells were fused with SP2/0 cells by electrofusion to prepare hybridoma cells. Mice were immunized in the same way and phage library antibodies were prepared. Primary screening was performed by ELISA and flow cytometry, 32 hybridoma antibodies and 2 phage antibodies were obtained to bind human CD73 and cynomolgus CD73. Then, 293T/17 cells expressing huCD73 (293T/17-huCD73) were used to further screen the blockade enzyme activity, and finally 5 clones with function of blockade of CD73 enzyme activity were obtained.

Example 2: Indirect Assay of the Binding of Antibodies to CD73 by ELISA

The indirect ELISA method was applied to evaluate the binding ability of each positive clone to soluble huCD73 protein. Soluble huCD73 was coated, and gradient diluted samples were incubated, then HPR-labeled secondary antibody was added, finally TMB was added to develop the color, and OD450 was read after termination. As shown in FIG. 1, the result showed that all three cloned antibodies of 66F2A8D6 (SEQ ID NOs: 118 and 119), 94A12G11F2 (SEQ ID NOs: 120 and 121), 191C3A8B9 (SEQ ID NOs: 122 and 123) and two phage antibodies of S1B5 (SEQ ID NOs: 13 and 14) and JB24Chi (SEQ ID NOs: 26 and 28) bind to soluble recombinant CD73 with sub-nanomolar affinity.

TABLE 1

Binding ability of positive clones to soluble huCD73 protein

| Ab | Bottom | Top | $EC_{50}$ (nM) |
|---|---|---|---|
| 66F2A8D6 | 0.1646 | 3.108 | 0.153 |
| 94A12G11F2 | 0.0566 | 2.941 | 0.242 |
| 191C3A8B9 | 0.0498 | 2.748 | 0.279 |
| S1B5 | 0.0070 | 2.926 | 0.085 |
| JB24Chi | 0.1360 | 3.086 | 0.039 |

Figure 2:
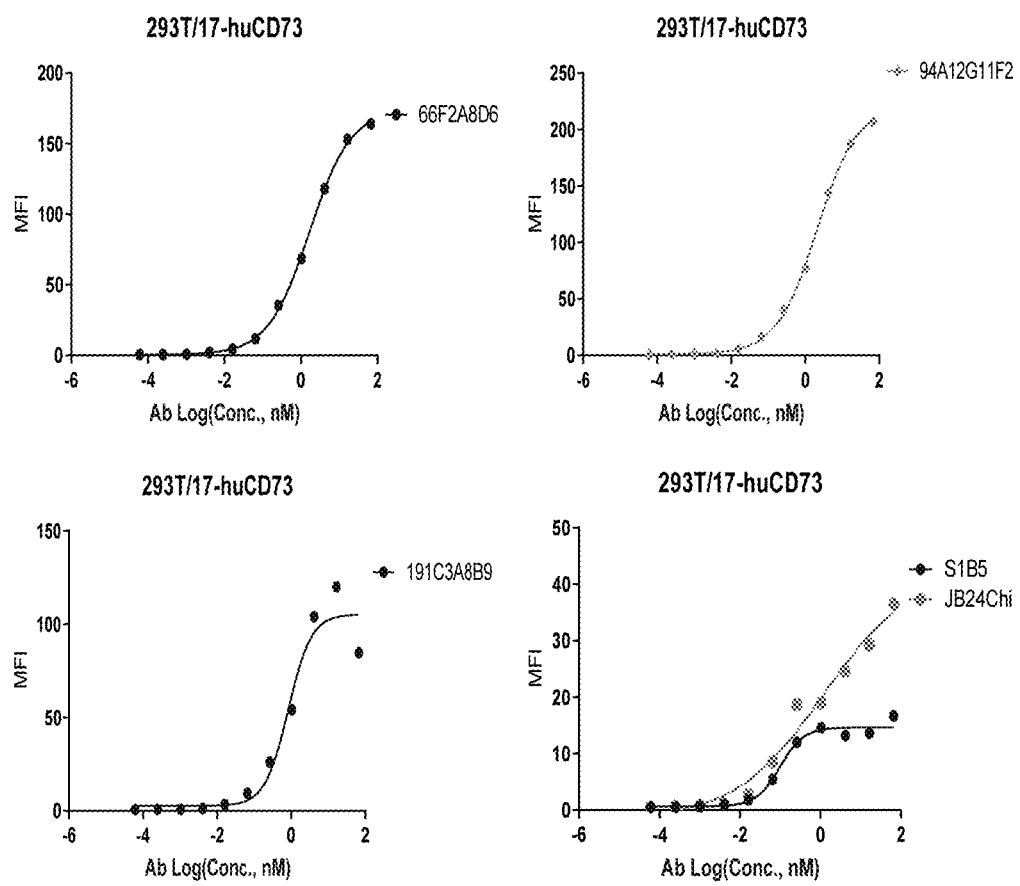
FIG. 2 shows the binding ability assay of the positive clones and the natural CD73 protein.

Example 3: Assay of the Binding of Antibodies to Natural CD73 Cell Surface by Flow Cytometry 293T/17-huCD73 cells were used to evaluate the binding ability of five antibodies to natural CD73 on cell surface. After incubating gradient diluted antibodies with 293T/17-huCD73 cells, fluorescently labeled detection antibody was added, the fluorescence intensity value was read, and $EC_{50}$ was calculated. As shown in FIG. 2, the results showed that all antibodies bind to CD73 on cell surface with nanomolar or sub-nanomolar affinity.

TABLE 2

Binding ability of positive clones to natural CD73 protein

| Ab | Bottom | Top | $EC_{50}$ (nM) |
|---|---|---|---|
| 66F2A8D6 | 0.5465 | 174.2 | 1.664 |
| 94A12G11F2 | 1.132 | 221.7 | 2.077 |
| 191C3A8B9 | 2.671 | 105.4 | 0.828 |
| S1B5 | 0.6408 | 14.66 | 0.099 |
| JB24Chi | −1.467 | 41.98 | 1.135 |

Example 4: Evaluation of Blockade of Soluble CD73 Recombinant Protease Activity

Figure 3:
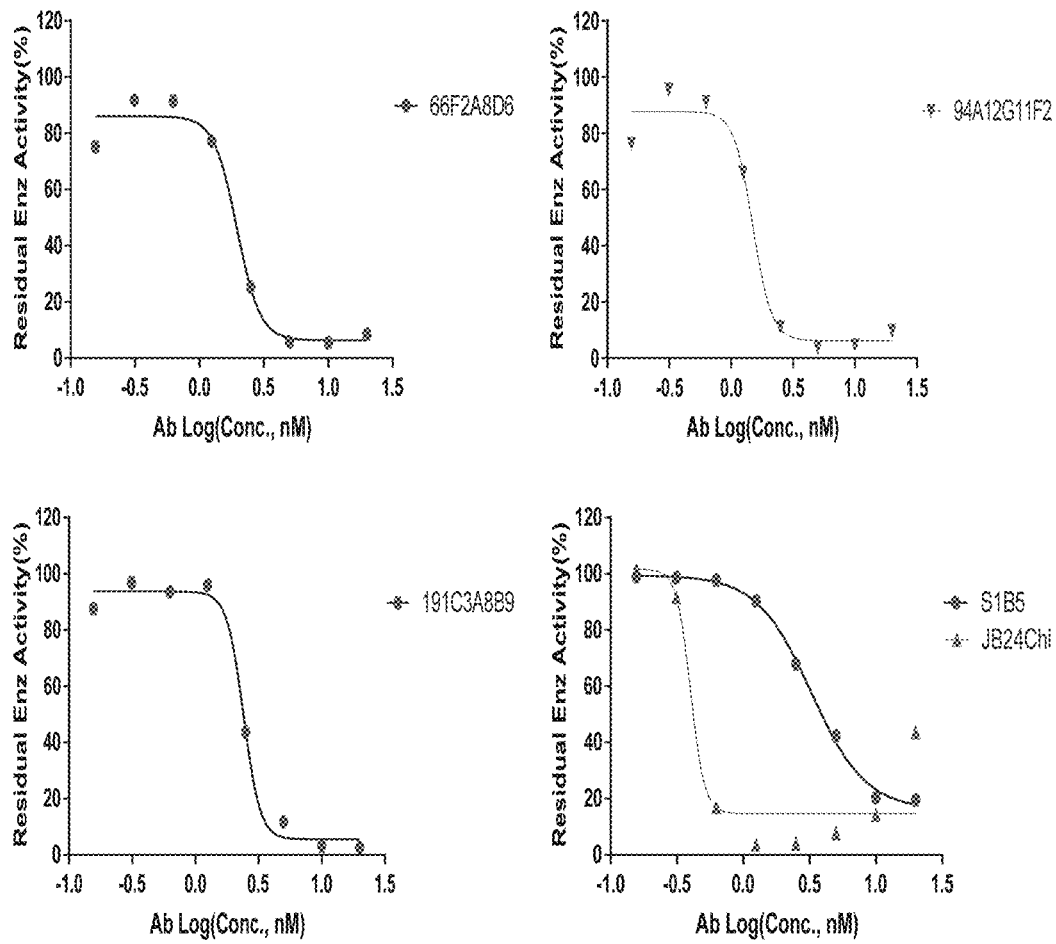
FIG. 3 showing the enzyme activity blockage of soluble recombinant human CD73.

This assay evaluates the blockade ability of CD73 antibodies to the 5'exonuclease of soluble huCD73 recombinant protease. The binding of antibodies blocks the activity of huCD73 recombinant protein to hydrolysis AMP into adenosine and inorganic phosphate, while the competition of AMP with ATP inhibits the ability of luciferase to emit light. Thus, blocking antibodies attenuate light emission and results in reduced RLU values. As shown in FIG. 3, 66F2A8D6, 94A12G11F2, 191C3A8B9, antibody S1B5 and JB24Chi all have inhibitory effects on the activity of soluble CD73 recombinant protein, and the $IC_{50}$ were at the nanomolar or subnanomolar level.

TABLE 3

The ability of CD73 antibodies to block soluble CD73 recombinant protease activity

| Ab | Bottom | Top | $IC_{50}$ (nM) |
|---|---|---|---|
| 66F2A8D6 | 6.361 | 86.08 | 1.956 |
| 94A12G11F2 | 6.213 | 87.77 | 1.496 |
| 191C3A8B9 | 5.553 | 93.72 | 2.407 |
| S1B5 | 16.180 | 99.47 | 3.259 |
| JB24Chi | 14.710 | 101.70 | 0.401 |

Figure 4:
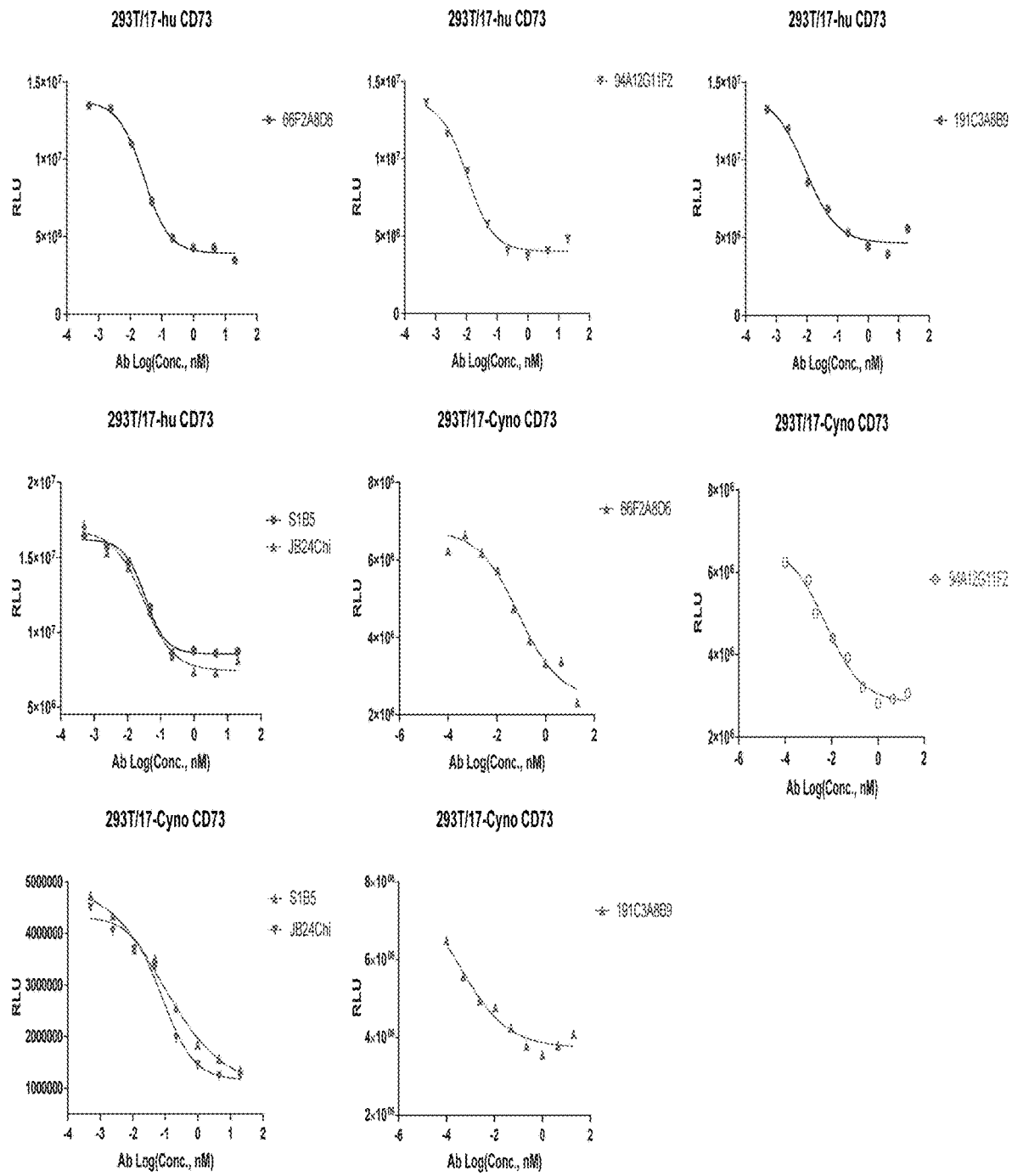
FIG. 4 shows the cell-based enzyme activity blocking experiment.

Example 5: Blockade of 5' Exonuclease on the Cell Surface Activity Against CD73 Antibody This method was based on 293T/17-huCD73 and 293T/17-cynoCD73 cells to evaluate the blockade ability of CD73 antibodies to 5'exonuclease on the cell surface activity, to further confirm the biochemical activities of the five antibodies. As shown in FIG. 4, all antibodies could inhibit the 5'exonuclease on the cell surface activity. Among them, the inhibitory activity of 191C3A8B9 against huCD73 was weaker than that of cynomolgus CD73, the others had similar inhibitory activity on human/cynomolgus CD73. The $IC_{50}$ values of all antibodies were $10^{-11}$~$10^{-12}$M (Table 4).

TABLE 4

The ability of CD73 antibodies to block 5' exonuclease on the cell surface activity

| | 293T/17-HuCD73 | | | 293T/17-cyno CD73 | | |
|---|---|---|---|---|---|---|
| Ab | Bottom | Top | $IC_{50}$ (nM) | Bottom | Top | $IC_{50}$ (nM) |
| 66F2A8D6 | 3935659 | 13777015 | 0.027 | 2542560 | 6682235 | 0.077 |
| 94A12G11F2 | 4013533 | 13788420 | 0.011 | 2845459 | 6641976 | 0.006 |
| 191C3A8B9 | 4644137 | 14192084 | 0.009 | 3764123 | 7369545 | 0.001 |
| S1B5 | 8532921 | 16191747 | 0.034 | 1044320 | 4968902 | 0.085 |
| JB24Chi | 7418313 | 16806180 | 0.031 | 1156967 | 4317630 | 0.084 |

Example 6: Reverse Effect of CD73 Antibody on Amp-Mediated Human CD4+t Cell Proliferation Inhibition Antibodies blocked the enzymatic activity of CD73, and the production of adenosine was inhibited, thereby releasing the proliferation inhibition of human CD4+ T cells adenosine. This method confirmed the ability of CD73 antibody to release AMP-mediated CD4+ T cell proliferation inhibition in vitro; at the same time, the blockade of CD73 antibodies to CD4+ T cell CD73 was detected by CellTiter-Glo (Promega) reagent; and the IFN-γ levels in cell culture supernatant were detected by ELISA.

Figure 5:
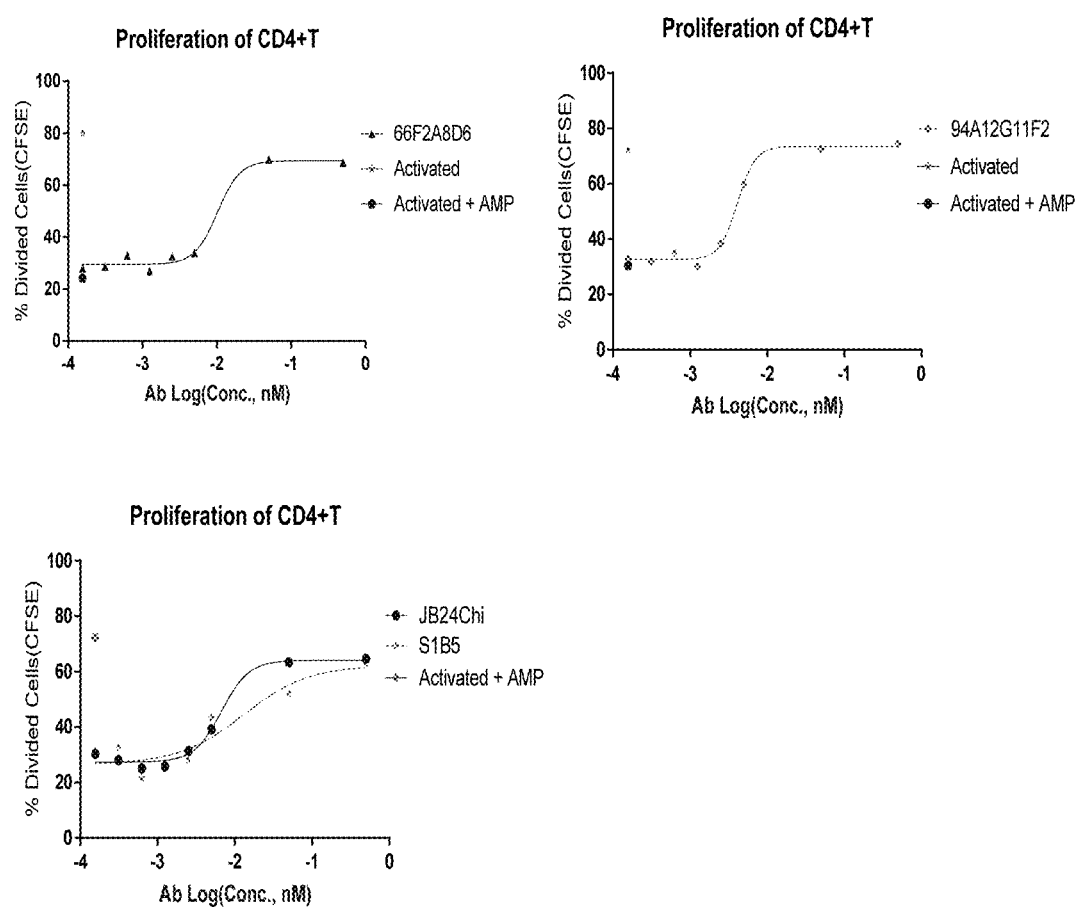
FIG. 5 shows CD4+ T cell proliferation reversed by CD73 antibody.

The results showed that 66F2A8D6, 94A12G11F2, S1B5, and JB24Chi can reverse the AMP-mediated CD4+ T cell proliferation inhibition (FIG. 5), and the $EC_{50}$ values were relatively close, all in $10^{-11}$~$10^{-12}$M (Table 5)

TABLE 5

The ability of CD73 antibodies reversing AMP-mediated human CD4 + T cell proliferation inhibition

| Ab | Bottom | Top | $EC_{50}$ (nM) |
|---|---|---|---|
| 66F2A8D6 | 29.55 | 69.45 | 0.010 |
| 94A12G11F2 | 32.63 | 73.53 | 0.004 |
| S1B5 | 27.36 | 64.14 | 0.013 |
| JB24Chi | 26.58 | 62.33 | 0.007 |

Figure 6:
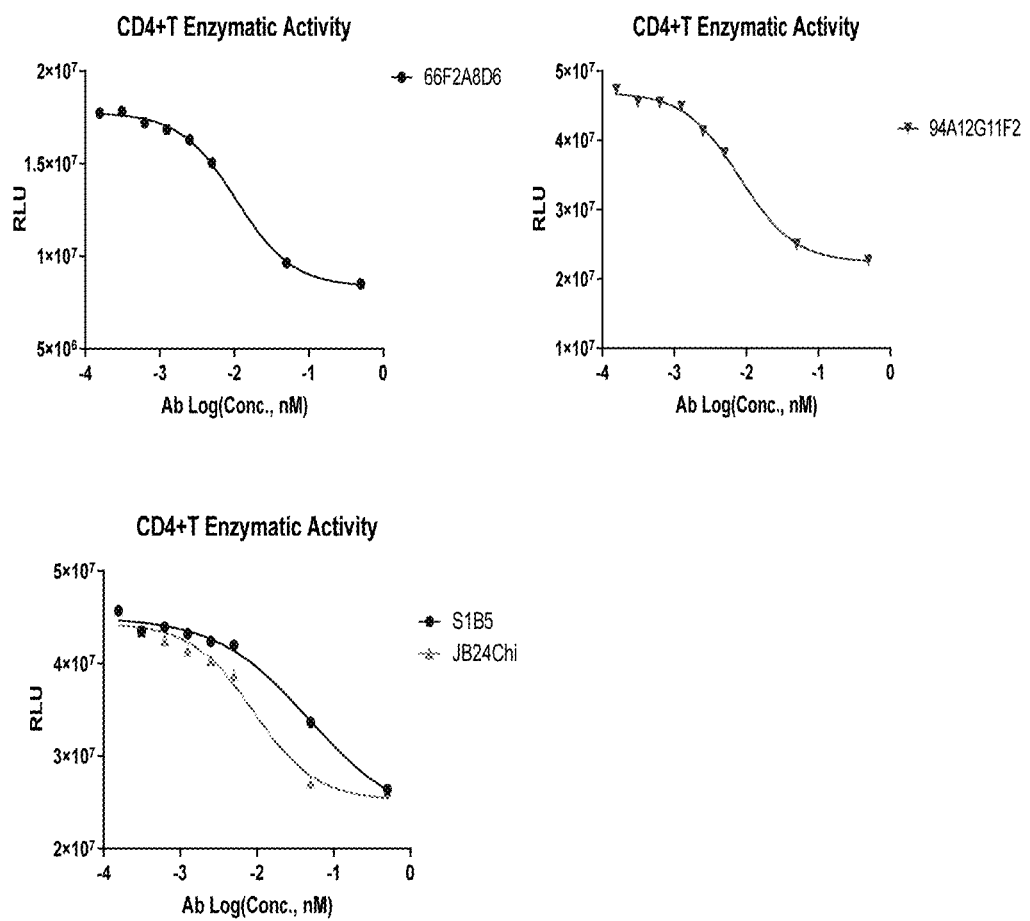
FIG. 6 shows CD73 enzyme activity of CD4+ T cells blocked by antibody.

Similar to the results of CD4+ T cell proliferation experiments, 66F2A8D6, 94A12G11F2, S1B5, and JB24Chi all had potent inhibitory effects on enzyme activity (FIG. 6), and the inhibitory ability were $10^{-11}$~$10^{-12}$M (Table 6).

TABLE 6

The ability of antibodies blocking CD4 + T cell

| Ab | Bottom | Top | $IC_{50}$ (nM) |
|---|---|---|---|
| 66F2A8D6 | 8353547 | 17766093 | 0.011 |
| 94A12G11F2 | 22404704 | 46921097 | 0.008 |
| S1B5 | 22907851 | 25212940 | 0.048 |
| JB24Chi | 45017675 | 44400168 | 0.009 |

Figure 7:
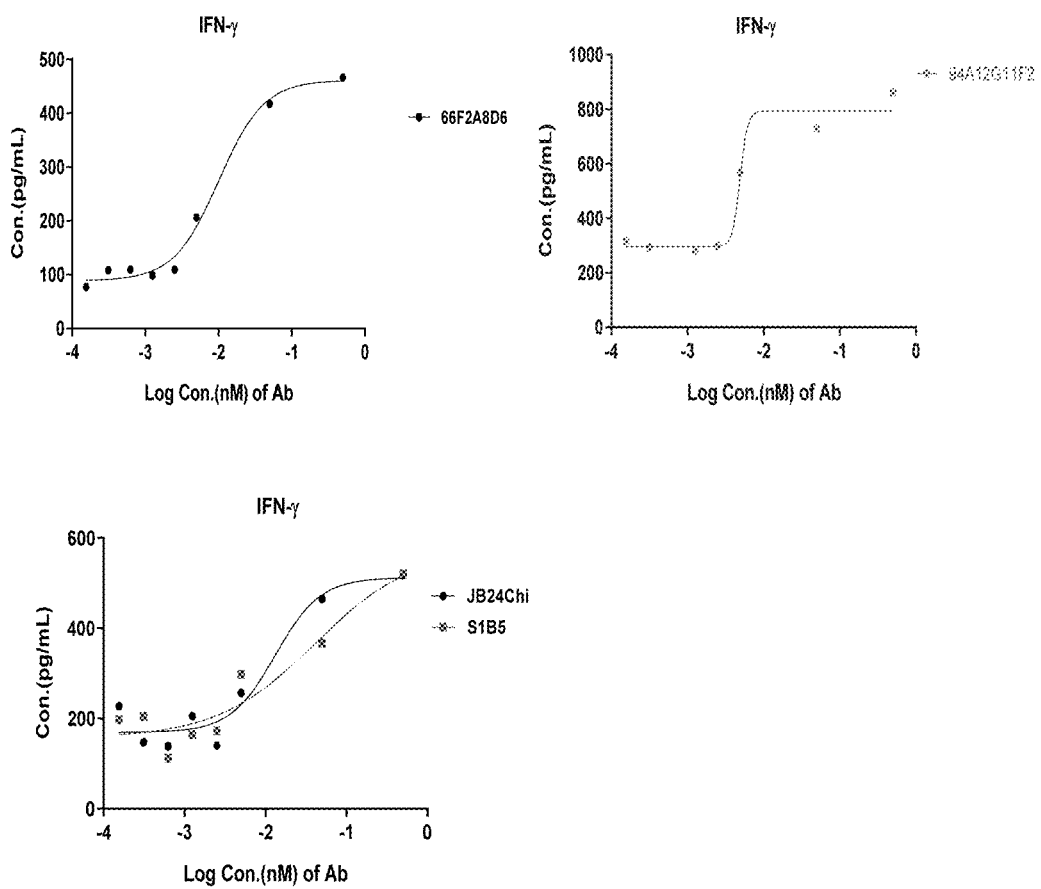
FIG. 7 shows IFN-γ releasing from CD4+ T cells reversed by antibody.

ELISA detection kit (Dakewe) was used to detect supernatant IFN-γ, as shown in FIG. 7, 66F2A8D6, 94A12G11F2, S1B5 and JB24Chi can stimulate CD4+ T cells to release IFN-γ, and the $EC_{50}$ of each antibody stimulated T cells to secrete IFN-γ was in the range of $10^{-11}$~$10^{-12}$M (Table 7).

TABLE 7

The ablity of antibodies to reverse the release of IFN-γ from CD4 + T cells

| Ab | Bottom | Top | $EC_{50}$ (nM) |
|---|---|---|---|
| 66F2A8D6 | 88.7 | 461.4 | 0.0101 |
| 94A12G11F2 | 296.6 | 794.6 | 0.0049 |
| S1B5 | 156.6 | 576.3 | 0.0411 |
| JB24Chi | 169.1 | 512.1 | 0.0132 |

Example 7: Experiment of CD73 Antibody-Mediated CD73 Internalization

Figure 8:
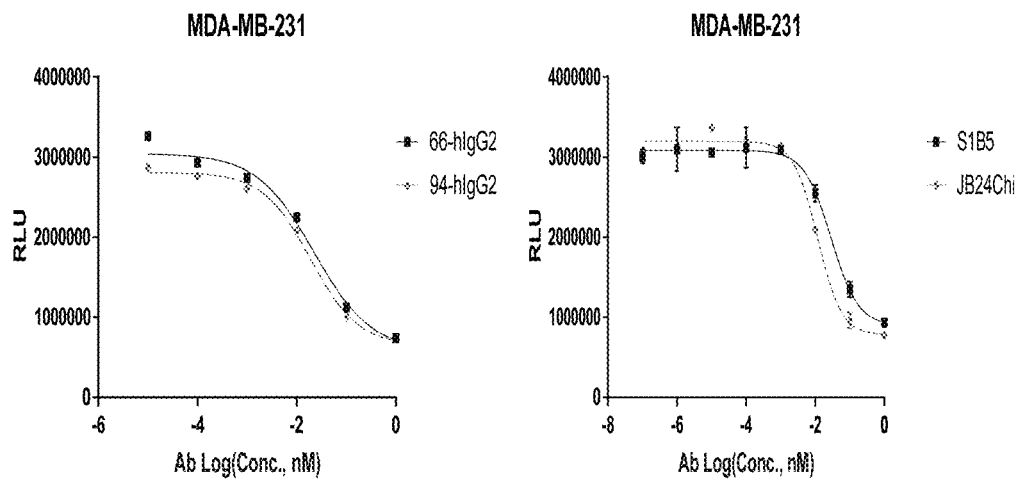
FIG. 8 shows CD73 endocytosis mediated by CD73 antibody.

66-IgG2 (SEQ ID NOs: 39 and 40), 94-IgG2 (SEQ ID NOs: 51 and 53), S1B5, JB24Chi antibodies mediated internalization effect on MDA-MB-231 cell was detected using the Fab-ZAP saporin conjugate (Advanced Targeting Systems). As shown in FIG. 8, all four chimeric antibodies mediated the internalization effect of CD73 in a dose-dependent manner, and the $IC_{50}$ of each antibody was about $10^{-11}$M.

TABLE 8

The ability of antibody-mediated internalization of CD73

| Ab | Bottom | Top | $IC_{50}$ (nM) |
|---|---|---|---|
| 66-hIgG2 | 581873 | 3044537 | 0.022 |
| 94-hIgG2 | 649643 | 2809795 | 0.019 |
| S1B5 | 896346 | 3084741 | 0.029 |
| JB24Chi | 779820 | 3197304 | 0.012 |

Example 8: Humanization of Antibodies

The CDR and framework regions are numbered, and the amino acids of each antibody in the CDR regions and framework regions are numbered according to the Kabat system (see Table I). Two antibodies 94A12E7D5 and JB24Chi were humanized by CDR grafting method. The sequence identity and structural similarity of two murine antibodies and human antibodies were analyzed respectively, and the CDRs of the murine antibodies were grafted to a series of human antibody templates based on the above. After preliminary screening by ELISA, three humanized antibodies of JB24Chi and three humanized antibodies of 94A12E7D5 were obtained, which named as JB24H2L1 (SEQ ID NOs: 71 and 73), JB24H3L2 (SEQ ID NOs: 72 and 74), JB24H3L3 (SEQ ID NOs: 72 and 75), JB94H1L3 (SEQ ID NOs: 81 and 85), JB94H2L1 (SEQ ID NOs: 82 and 84), and JB94H3L3 (SEQ ID NOs: 83 and 85) respectively. Chimeric antibodies consisting of mouse-derived antibodies' FAT of 94A12G11F and human IgG1 and human kappa constant regions were named JB94Chi (SEQ ID NOS: 52 and 53).

Figure 9:
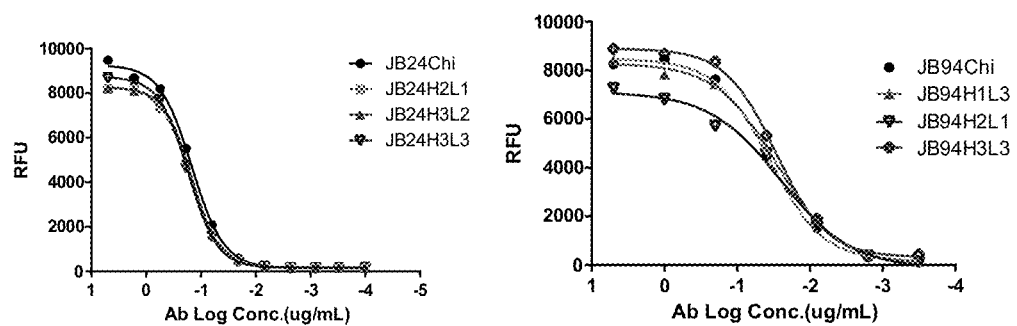
FIG. 9 shows the affinity of humanized antibodies and chimeric antibodies detected by ELISA.

Example 9: The Assay of Affinity of Humanized Antibodies and Chimeric Antibodies The affinity of humanized antibodies was determined by indirect ELISA: 96-well ELISA plates were coated with 1 μg/ml huCD73recombinant protein, 50 ul/well, washed the plate 3 times with 200 ul PBST per well, blocked with 200 ul/well of 1% BSA for 1 h at room temperature, and the plates were washed 3 times with 200 ul/well of PBST. Incubated with gradient diluted 100 μL/well of antibodies for 1 h at room temperature. After the plates were washed 3 times with 200 ul/well of PBST, 100 ul of diluted HRP-labeled secondary antibody at a ratio of 1:5000 was added to each well, and the plates were incubated for 1 hour at room temperature. The plates were washed 3 times with 200 ul/well of PBST, 100 ul of TMB was added to each well and reacted for 5 minutes at room temperature in the dark. Excitation at 530 nm, emission at 590 nm, cut-off at 570 nm, read the OD value. The results were shown in FIG. 9. The affinity of humanized antibodies and parent antibodies were similar to the antigen (table 9).

TABLE 9

The affinity of humanized antibodies to soluble huCD73

| Ab | Bottom | Top | $EC_{50}$ (nM) |
|---|---|---|---|
| JB24Chi | 128.1 | 6601 | 0.0273 |
| JB24H2L1 | 190.9 | 6293 | 0.0248 |
| JB24H3L2 | 89.06 | 7139 | 0.0208 |
| JB24H3L3 | 9.8 | 7306 | 0.0228 |
| JB94Chi | 152 | 8474 | 0.0357 |
| JB94H1L3 | 48.7 | 8288 | 0.0289 |
| JB94H2L1 | −141.9 | 7111 | 0.0252 |
| JB94H3L3 | 320 | 8897 | 0.0292 |

Flow cytometry assay: the huCD73 or cynoCD73-expressing 293T/17 cells were used to evaluate the binding ability of humanized antibodies. $2 \times 10^6$ cells resuspended in PBS buffer were distributed into 96-well plates and incubated with gradient diluted humanized antibodies for 1 h at refrigerator 4° C. or on ice, then the cells was centrifuged for 3 min 1500 rpm at 4° C. and washed three times by PBS, and diluted APC-labeled goat anti-human polyclonal antibody (Biolegend) were incubated for 30 min at refrigerator 4° C.

Figure 10:
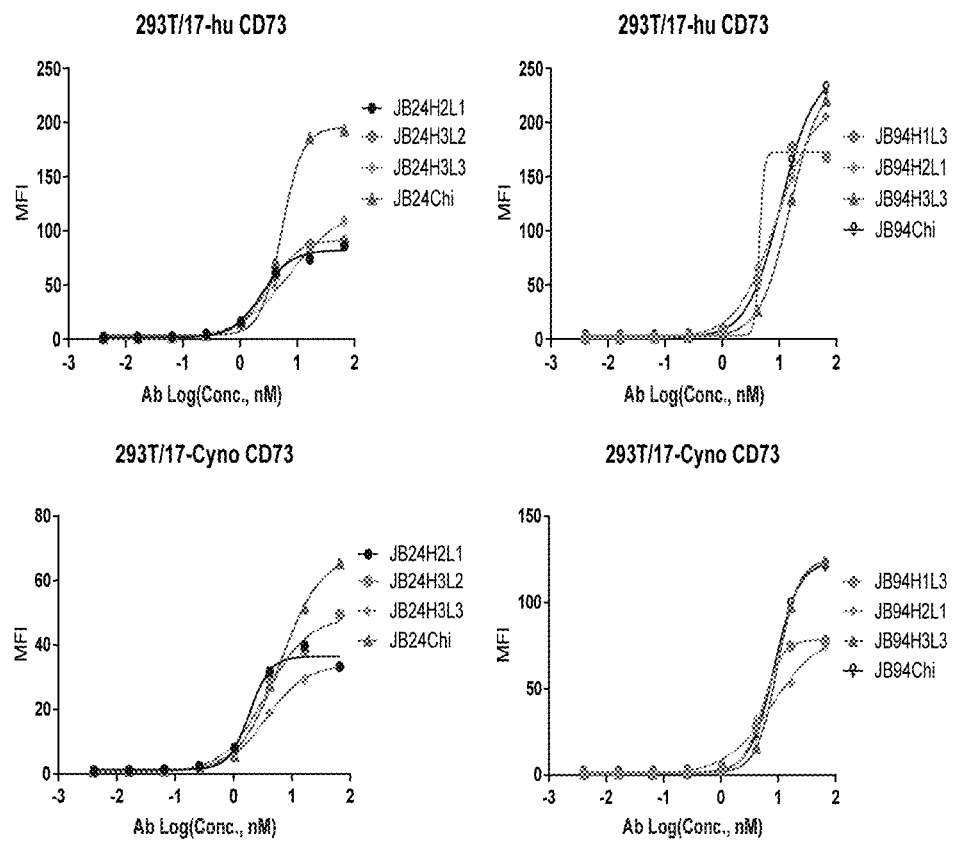
FIG. 10 shows the affinity of humanized antibodies and chimeric antibodies detected by FACs.

Finally, the cells were washed three times with PBS as described above and analyzed on MACSQuant flow cytometer. GraphPad Prism software was used to generate data graphs and statistical affinity data. As shown in FIG. 10, humanized antibodies of JB24Chi and 94A12G11F had similar $EC_{50}$ values to their parent antibodies, both in the $10^{-11}$M to $10^{-12}$M (Table 10).

TABLE 10

Affinity of humanized antibodies and chimeric antibodies to huCD73 and cynoCD73 antigens on cell surface

| | 293T/17-human CD73 | | | 293T/17-Cyno CD73 | | |
|---|---|---|---|---|---|---|
| Ab | Bottom | Top | $EC_{50}$ (nM) | Bottom | Top | $EC_{50}$ (nM) |
| JB24H2L1 | 1.639 | 82.25 | 2.404 | 1.401 | 36.54 | 1.892 |
| JB24H3L2 | 1.779 | 91.74 | 3.009 | 0.509 | 48.67 | 3.593 |
| JB24H3L3 | 0.131 | 120.50 | 7.406 | 0.917 | 34.01 | 3.729 |
| JB24Chi | 3.723 | 195.50 | 5.334 | 0.709 | 68.54 | 6.379 |
| JB94H1L3 | 3.258 | 172.50 | 4.507 | 1.510 | 78.70 | 5.424 |
| JB94H2L1 | 0.604 | 222.80 | 9.152 | 0.220 | 82.03 | 7.974 |
| JB94H3L3 | 1.785 | 239.30 | 15.290 | 1.395 | 125.40 | 9.824 |
| JB94Chi | 1.405 | 246 | 10.630 | 1.445 | 123.90 | 8.588 |

Figure 11:
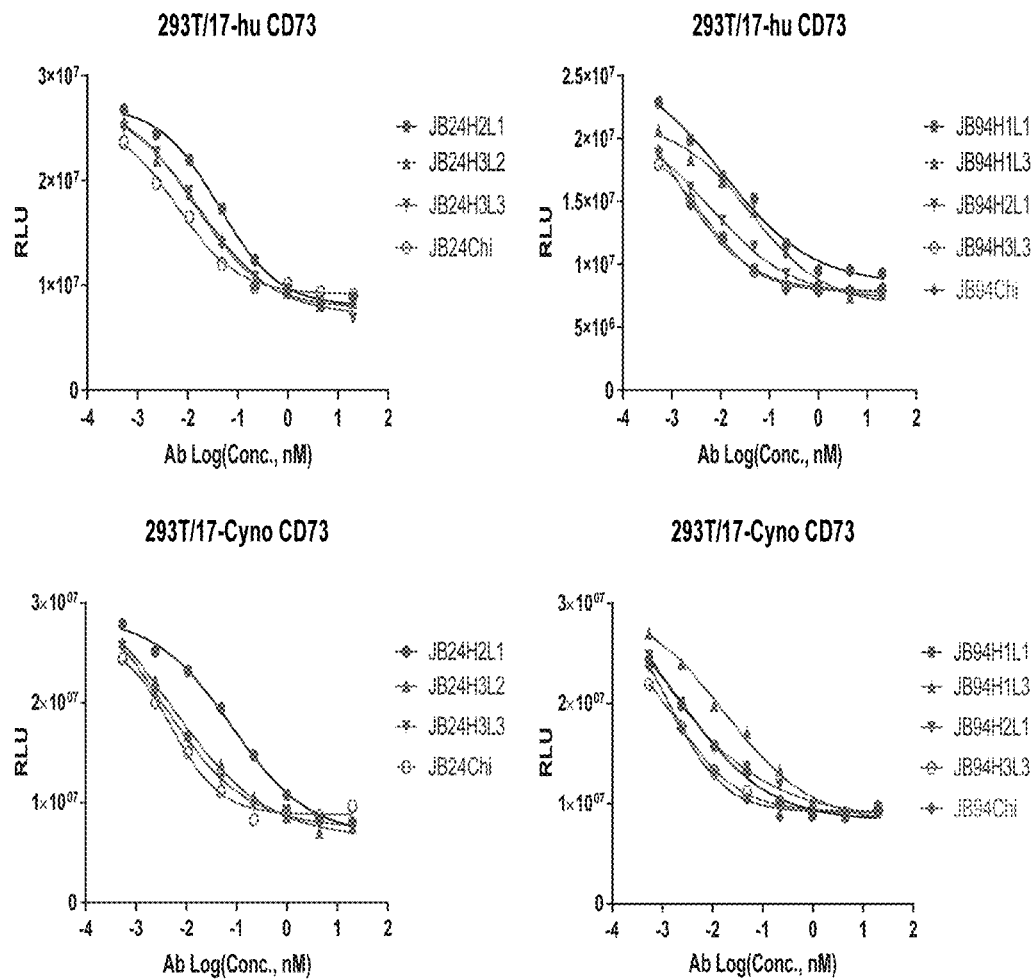
FIG. 11 shows the 5' exonuclease activity on the cell surface blocked by humanized antibody.

Example 10: Blockade of 5'Exonuclease on the Cell Surface Activity Against Humanized Antibodies This method uses 293T/17-huCD73 cells to evaluate the AMP hydrolysis inhibited by CD73, to further confirm the biochemical activities of humanized antibodies. As shown in FIG. 11, the enzymatic blocking activities of all humanized antibodies of JB24H3L3, JB94H1L3, 94H1L3 hIgG2 (SEQ ID NOs:85 and 124) were in the $10^{-11}$-$10^{-12}$M levels (Table 11).

TABLE 11

Blockade activities of 5' exonuclease on the cell surface activity against humanized antibodies

| | 293T/17-human CD73 | | | 293T/17-Cyno CD73 Cells | | |
|---|---|---|---|---|---|---|
| Ab | Bottom | Top | $IC_{50}$ (nM) | Bottom | Top | $IC_{50}$ (nM) |
| JB24H2L1 | 8039545 | 27092351 | 0.042 | 6718233 | 28633058 | 0.079 |
| JB24H3L2 | 7836350 | 27586937 | 0.014 | 6431345 | 33705693 | 0.004 |
| JB24H3L3 | 7183191 | 27666447 | 0.016 | 7462673 | 32900976 | 0.003 |
| JB24Chi | 9147540 | 26077507 | 0.006 | 8819632 | 26477691 | 0.005 |
| JB94H1L3 | 6727576 | 21364881 | 0.042 | 8000768 | 30217678 | 0.017 |
| 94H1L3 hIgG2 | 2016997 | 10921025 | 0.007 | 1213837 | 5673059 | 0.021 |
| JB94H2L1 | 7233354 | 22246467 | 0.005 | 8309853 | 54243915 | 0.0001 |
| JB94H3L3 | 7810738 | 19948965 | 0.004 | 9203356 | 27004932 | 0.002 |
| JB94Chi | 7836630 | 26055691 | 0.001 | 9159630 | 30233789 | 0.001 |

Figure 12:
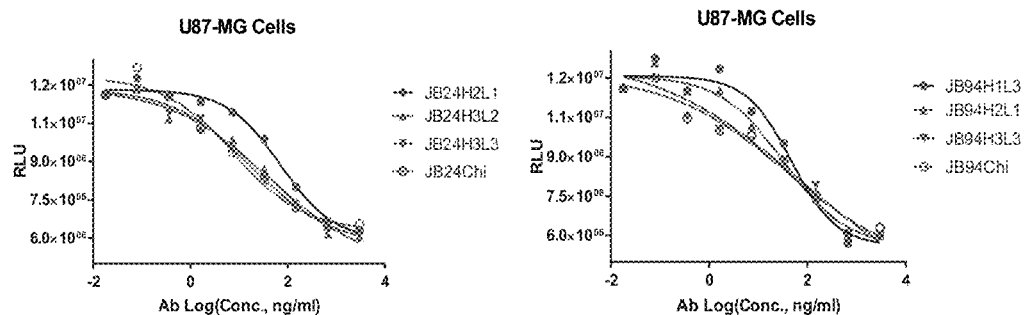
FIG. 12 shows 5' ectonucleotidase activity of U87-MG cell blocked by humanized antibody.

In addition, U87-MG cells were used to evaluate hydrolysis of AMP catalyzed by CD73, and further confirm the biochemical activity of humanized antibodies. After U87-MG cells were digested with trypsin, the cell density was adjusted to $4\times10^5$ cells/ml with MEM medium, and 50 μl/well was added to a 96-well plate. The humanized antibody was gradient diluted by MEM medium, 50 μl/well was added to the wells, and incubated for 1 h at 37° C. 100 μl of 360 μM AMP was added to each well and incubated for 1 h at 37° C. The plates were then centrifuged for 3 min at 1500 rpm, a certain volume of culture supernatants were transferred to a opaque 96-well flat bottom plate (Costar, 3912), and added 2× ATP to make the final reaction concentration of 25 μM. Finally, according to Promega instructions, corresponding volume of CellTiter Glo reagent in a ratio of 1:1 was added. After equilibrated for 5 minutes at room temperature, luminescence value was read on Perkin-Elmer Envision microplate reader and cell CD73 enzyme activity was determined by measuring ATP levels. GraphPad Prism software was used to generate data graphs and statistical enzyme kinetic data. The blocking activities of humanized antibodies of JB24Chi and JB94Chi were shown in FIG. 12, both value of $IC_{50}$ is in the sub-nanomolar class (Table 12).

TABLE 12

Blockade ability of 5 'exonuclease activity of U87-MG cells against humanized antibodies

| Ab | Bottom | Top | IC50 (nM) |
|---|---|---|---|
| JB24H2L1 | 5795303 | 11954887 | 0.474 |
| JB24H3L2 | 4703766 | 12052334 | 0.270 |
| JB24H3L3 | 5596400 | 12116519 | 0.120 |
| JB24Chi | 5780677 | 14683906 | 0.053 |
| JB94H1L3 | 5605512 | 12073719 | 0.314 |
| JB94H2L1 | 5565211 | 12085615 | 0.214 |
| JB94H3L3 | 3402301 | 12844937 | 0.456 |
| JB94Chi | 4653071 | 12168782 | 0.257 |

Example 11: Reverse Effect of Humanized Antibody on AMP-Mediated Human CD4+ T Cell Proliferation Inhibition This method confirmed the ability of humanized CD73 antibody to release AMP-mediated CD4+ T cell proliferation inhibition in vitro; at the same time, the blockade ability of humanized antibodies to CD4+ T cell CD73 enzyme activity was detected by CellTiter-Glo (Promega) reagent; and the IFN-γ levels in cell culture supernatant were detected by ELISA.

Figure 13:
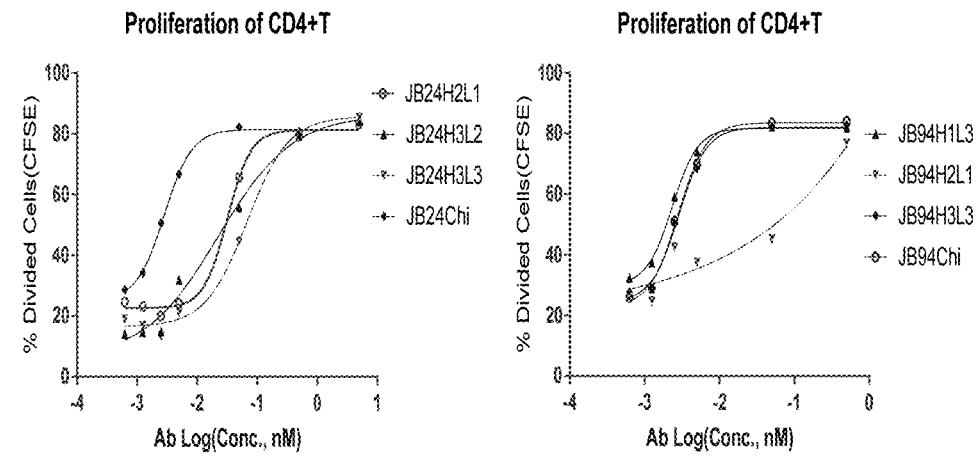
FIG. 13 shows CD4+ T cell proliferation reversed by humanized CD73 antibody.

The results of the activities of humanized antibody of JB24Chi and JB94Chi were shown in FIG. 13. Among them, the activities of JB94H1L3, 94H1L3 hIgG2 and JB94H3L3 were about $10^{-11}$~$10^{-12}$M (Table 13).

TABLE 13

The ability of humanized antibodies reversing AMP-mediated human CD4 + T cell proliferation inhibition

| Ab | Bottom | Top | $EC_{50}$ (nM) |
|---|---|---|---|
| JB24H2L1 | 22.61 | 81.28 | 0.032 |
| JB24H3L2 | 6.097 | 86.32 | 0.022 |
| JB24H3L3 | 16.45 | 85.72 | 0.068 |
| JB24Chi | 25.18 | 81.45 | 0.003 |
| JB94H1L3 | 29.9 | 81.79 | 0.002 |
| 94H1L3 hIgG2 | 0.558 | 103.5 | 0.012 |
| JB94H2L1 | 20.33 | 81.28 | 0.032 |
| JB94H3L3 | 24.47 | 82.01 | 0.003 |
| JB94Chi | 22.86 | 83.57 | 0.003 |

Figure 14:
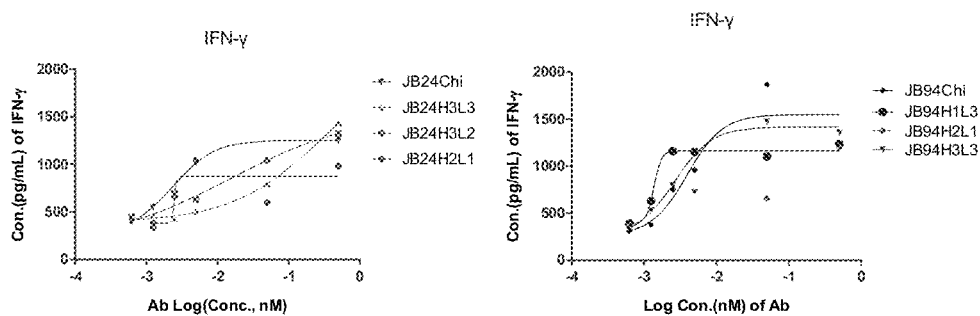
FIG. 14 shows IFN-γ releasing from CD4+ T cells reversed by humanized CD73 antibody.

ELISA detection kit (Dakewe) was used to detect cell supernatant IFN-γ level. As shown in FIG. 14, except for JB24H3L3, each humanized antibody stimulated T cells to secrete IFN-γ with a $EC_{50}$ of $10^{-11}$~$10^{-12}$M (Table 14).

TABLE 14

The ability of humanized Cd73 antibodies reversing the release of IFN-γ from CD4 + T cells

| Ab | Bottom | Top | EC$_5$ (nM) |
|---|---|---|---|
| JB24H2L1 | 380.5 | 875 | 0.002 |
| JB24H3L2 | 164.6 | 1527 | 0.015 |
| JB24H3L3 | 387.6 | 2249 | 0.345 |
| JB24Chi | 474.1 | 1897 | 0.006 |
| JB94H1L3 | 391.1 | 1165 | 0.001 |
| 94H1L3 hIgG2 | 267.7 | 4791 | 0.001 |
| JB94H2L1 | 380.4 | 875 | 0.002 |
| JB94H3L3 | 245.9 | 1419 | 0.003 |
| JB94Chi | 267.4 | 1550 | 0.004 |

ELISA detection kit (Dakewe) was used to detect cell supernatant IFN-γ level. As shown in FIG. 14, except for JB24H3L3, each humanized antibody stimulated T cells to secrete IFN-γ with a EC$_{50}$ of $10^{-11}$~$10^{-12}$M. [ob2]

Figure 15A:
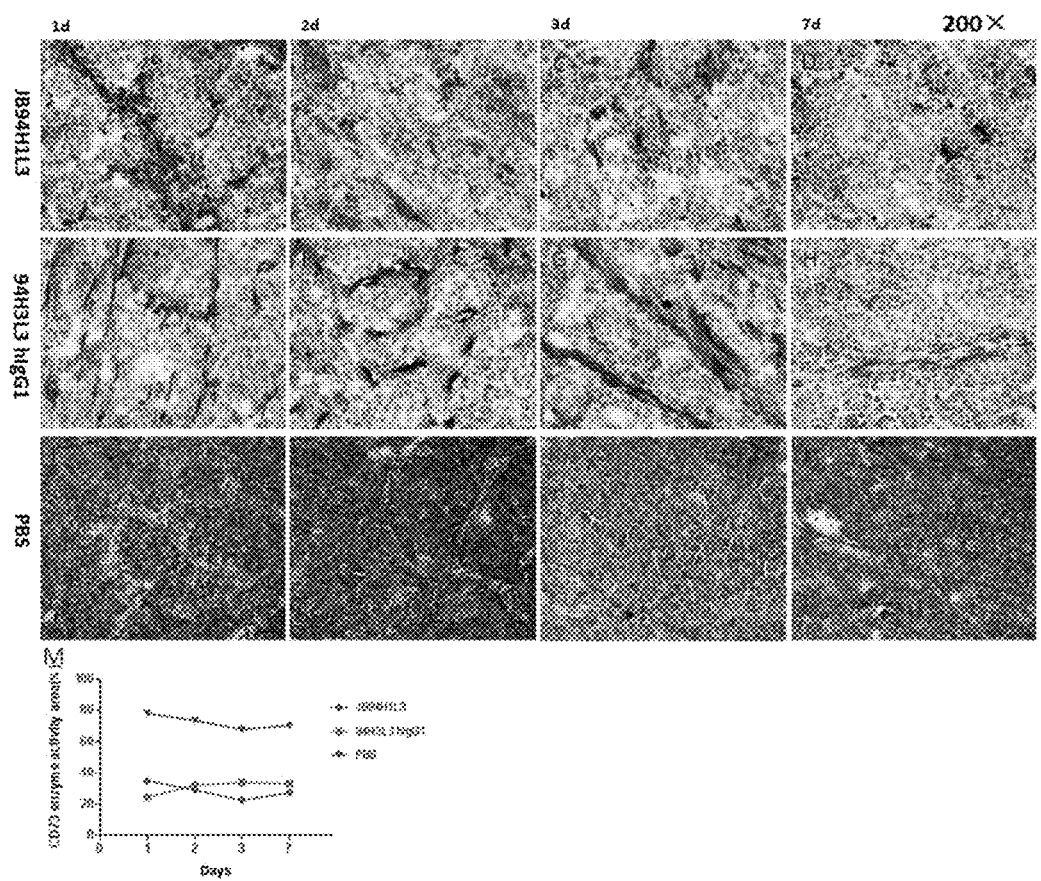
FIG. 15A and FIG. 15B show the inhibitory effect of humanized antibodies against the 5' exonuclease activity of tumors in xenograft animal models.
Figure 15B:
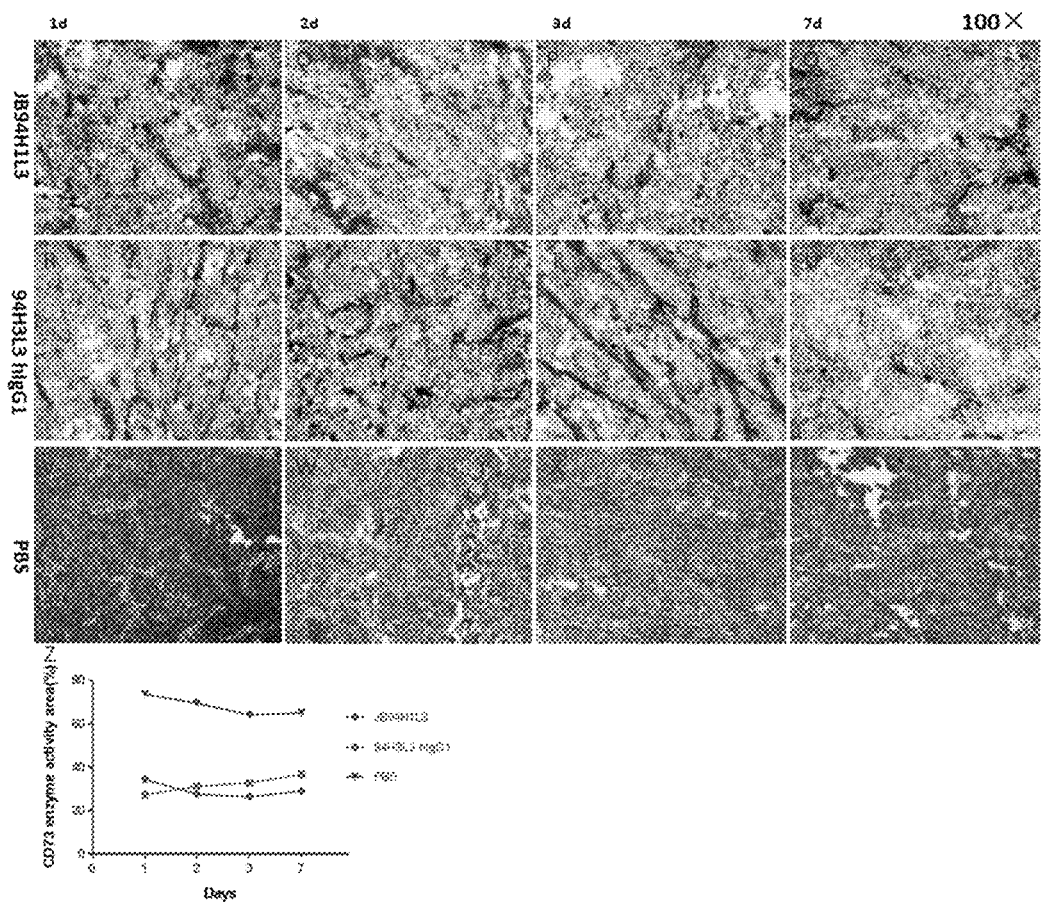

Example 12: Inhibition of 5'Exonuclease Activity in A375 Xenograft Model by Humanized Antibody B-NDG mice (Biocytogen) were subcutaneously inoculated with A375 cells, and 3 days later, the antibodies JB94H1L3, 94H3L3 hIgG1 (SEQ ID NOS: 91 and 85) or PBS were injected intraperitoneally (i.p.) 2 times/week, and dosing for two weeks, tumors were harvested at 1d, 2d, 3d, and 7d after administration. Place fresh tissue in a small cup filled with liquid nitrogen to freeze the tissue quickly, embed it in OCT, cut into 5-6 μm thickness and dry at room temperature. The tumor section is fixed with 4° C. precooled acetone for 20 min. Store at −80° C. after drying. Take the tumor section out of the refrigerator at −80° C., equilibrate at room temperature for 5-10 min, put it into 50 mM Tris-maleic acid buffer (PH7.4, containing 2 mM CaCl$_2$ and 0.25M sucrose), pre-incubate at room temperature for 1 h, remove the pre-incubation buffer after 1 h, and again add 50 mM Tris-maleic acid buffer (PH7.4, containing 5 mM MnCl$_2$, 2 mM lead nitrate, 2.5% dextran T200, 2.5 mM levamisole and 400 μM AMP), incubate at 37° C. for 1.5 h; rinse three times with water, incubate the sections with 1% (NH$_4$)$_2$S for 1 min at room temperature, and then quickly rinse three times with water; the sections were counterstained with hematoxylin and eosin, dehydrated, xylene transparent, and photographed under a microscope. Brown indicates the presence of activated CD73, and deletion of brown indicates that the antibody blocks the enzyme activity of CD73. Results are shown in FIG. 15 [ob3] and FIG. 15B.

The above results show that both JB94H1L3 and 94H3L3 hIgG1 can significantly reduce the 5'exonuclease activity of tumors in xenograft animal models, and are related to the administration time. On the 3rd day after discontinuation, the CD73 enzyme activity in the JB94H1L3 treatment group was reduced to the lowest point, and then slightly increased on the 7th day. The CD73 enzyme activity in the 94H3L3 hIgG1 treatment group gradually increased from the first day after administration. In summary, both antibodies showed good effect on inhibiting CD73 activity.

Figure 16:
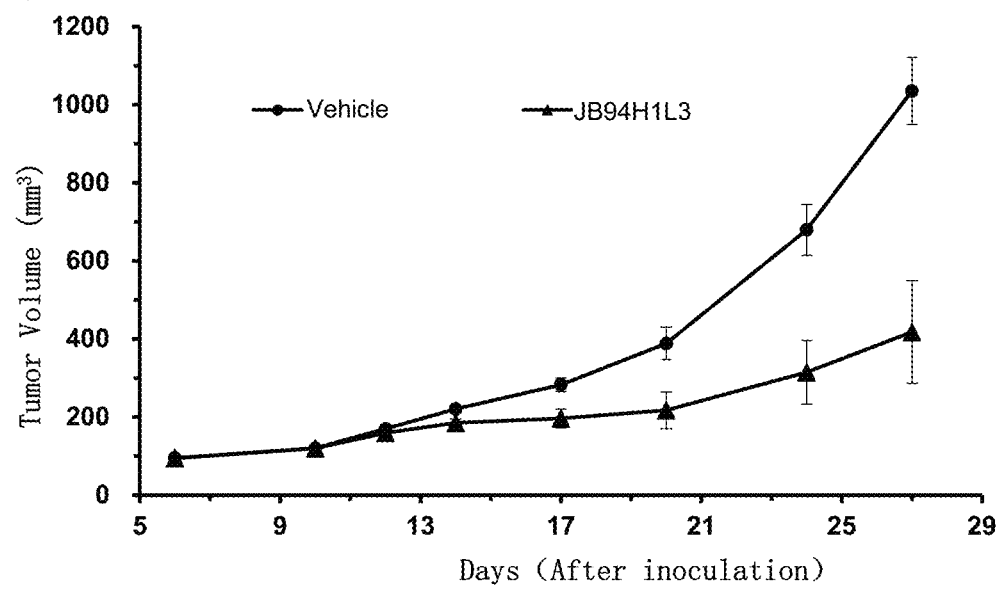
FIG. 16 shows the tumor suppression effect of humanized antibody on A375 human melanoma xenograft model.

Example 13: Tumor Suppressive Effect of Humanized Antibodies on A375 Human Melanoma Xenograft Model A375 human melanoma cells were inoculated subcutaneously in the right hypochondrium of NCG mice, and PBMC were resuspended in PBS and then inoculated in the mice. When the tumors grew to 50-100 mm$^3$, administering in two groups, giving JB94H1L3 (10 mg/kg) or soulvent control. The tumor volume was measured twice a week using vernier calipers to measure the long and short diameters of the tumor, and the volume calculation formula is: volume=0.5× long diameter×short diameter$^2$. As shown in FIG. 16, JB94H1L3 exhibited significant tumor growth inhibition effect.

These Results were Obtained Using the Following Materials and Methods:

Antibody Preparation:

Preparation of hybridoma antibodies: Thawed hybridoma cells were cultured for 7-10 days in 10% FBS-containing DMEM medium, and the cell culture supernatant was collected, centrifuged at 1000 rpm for 10 minutes, then the supernatants was purified with Protein G HP SpinTrap (GE Healthcare). Quantification was performed using an UV5nano (millipore) spectrophotometer.

Preparation of recombinant antibody: ExpiCHO cells (Thermo Fisher Scientific) with a viability of 99% were adjust to a density of 6×10$^6$ cells/ml. The cells were centrifuged at 1500 rpm for 5 min and resuspended. Prepare the expression vector diluent, ExpiFectamine CHO reagent diluent and DNA-ExpiFectamine CHO complex according to the instructions, and transfer the DNA-ExpiFectamine complex to the cell culture solution. Incubate for 8 days at 37° C. in an 8% CO$_2$ shaker. Centrifuge at 11,000 rpm for 10 min to collect the cell supernatant. Antibodies were purified using an NGC chromatography system (Bio-Rad) and rProtein G Beads 4FF pre-assembled columns. Quantification was performed using an UV5nano (millipore) spectrophotometer.

Assay 1: Indirect ELISA 1 ug/ml of recombinant CD73 protein was coated on ELISA plates (Coning), incubate overnight at 4° C. The next day, wash 5 times in PBS and blocked with 200 ul/well 2% skimmed milk, a certain dose range of CD73 antibodies were incubated for 1 h at room temperature. Wash 5 times with PBST washing buffer (PBS, 0.05% Tween 20), add HRP-conjugated goat anti-mouse IgG (H+L) (Promega) and incubate at room temperature for 1 h to detect bound anti-CD73 antibodies; wash the plate 5 times again and add TMB (Life Technologies) for color development for 5 to 10 min; finally the reaction was stopped by adding 1N HCl, and the OD value was measured at 450 nm. GraphPad Prism software was used to generate data graphs and statistical affinity data.

Assay 2: Flow Cytometry

Add 100 μL 2×10$^5$ cells/well expressing huCD73 (293T/17-huCD73), cynoCD73 (293T/17-cynoCD73) or moCD73 (293T/17-moCD73) cells to a 96-well U-shaped cell culture plate. The samples to be tested were incubated for 1 h at 4° C. after gradient dilution. After washing, 100 μL of APC-labeled secondary antibody was added to each well and incubated for 30 min. After washing, detecting on machine and the fluorescence value was read. GraphPad Prism software was used to generate data graphs and statistical affinity data.

Construction of recombinant host cells 293T/17-huCD73, 293T/17-cynoD73, 293T/17-moD73: use the PLVX-EF1a virus vector having huCD73, cynoCD73 and moCD73 genes and puromycin resistance to transfect 293T/17 cells with TransIT®-293 transfection reagent, after about 2 days, replace the complete medium containing puromycin to cultivate, and after the cells are expanded and cultivated, a single cloned cell is selected using a limited gradient dilution method, and PE-labeled anti-huCD73, cynoCD73 and moCD73 antibodies were used to detect cell surface antigens after transfection. Then the cells are expanded and cultivated for enzyme activity assay and flow cytometry.

Assay 3: Soluble CD73 Enzyme Activity Blocking Assay

The blocking function of enzyme activity by antibodies was determined based on the soluble CD73 recombinant protein. In the presence of 500 ng/ml CD73 recombinant protein, a certain dose range of CD73 antibody was added to a 96-well flat bottom plate and incubated at 37° C. for 1 h; then AMP and ATP with a final concentration of 180 uM and 25 uM was added to each well. Incubate for 30 min at 37° C.; transfer a certain volume of cell supernatant to a blank plate, add CellTiterr-Glo (Promega) containing luciferase to the above wells at a ratio of 1:1, at room temperature, equilibrated for 5 minutes in the dark. Finally, the Enspire microplate reader (Perkin Elmer) was used to measure the luminescence value. GraphPad Prism software was used to generate a data graph and statistics of enzyme kinetic data.

Assess the percentage of enzyme inhibition as follows:
ATP+AMP: maxial luciferase inhibition (100%)
ATP+AMP+CD73: no luciferase inhibition (0%)
The formula of resudual CD7 activity was evaluated as follows:

$$\frac{(CD73 + Ab + ATP + AMP) - (ATP + AMP)}{(CD73 + ATP + AMP) - (ATP + AMP)} * 100$$

Assay 4: Cell CD73 Enzyme Activity Blocking Assay

The 293T/17-huCD73 cells were digested, centrifuged at 1500 rpm for 3 minutes, and the supernatant was discarded. The cells were resuspended in serum-free DMEM medium and counted with a Biorad TC20 cell counter. Adjust the cell density, spread the cells into 96-well plates at 8,000 cells, 50 uL/well; add 50 uL gradient diluted antibody solution to the corresponding wells, and incubate in a 5% $CO_2$ incubator for 1 hour at 37° C.; then add 100 uL of AMP solution with a final concentration of 180 uM and incubate in a 5% $CO_2$ at 37° C. for 1 hour; then centrifuge the cell plate at 1500 rpm for 3 minutes and transfer a certain volume of culture supernatant to an opaque 96-well flat bottom plate (Costar, 3912), then add 2× ATP solution to make the final reaction concentration of 25 uM. Finally, add the corresponding volume of CellTiter Glo reagent at a ratio of 1:1 according to Promega's instructions. After equilibrating at room temperature for 5 minutes, read the luminescence value on a Perkin-Elmer Envision microplate reader and determine the cell CD73 enzyme activity by measuring the ATP level. GraphPad Prism software was used to generate data graphs and statistical enzyme kinetic data.

Assay 5: Fab ZAP Endocytosis Experiment

On the first day, 2000 cells/well of MDA-MB-231 cells were plated into 96-well flat bottom plates at 50 ul/well and incubated overnight at 37° C. in 5% $CO_2$; The next day, the antibodies were gradient diluted with 80 nM Fab-ZAP reagent (Advanced Targeting Systems) to a certain dose range, and incubated for 30 min at room temperature to bind Fab-ZAP to the antibody to be tested, then the antibodies were premixed, and 50 uL of the mixture were added to MDA-MB-231 cells wells, after 3 days incubation at 37° C. in 5% CO2, take the cell plate and add CTG reagent (Promega) to lyse the cells for 2 minutes, and then equilibrated the plates at room temperature for 5 minutes. Luminescences were measured using Enspire microplate reader (Perkin Elmer) and cell proliferation curves were analyzed by GraphPad Prism software.

The invention claimed is:

1. An isolated antibody or antigen-binding fragment thereof, that binds CD73, comprising a heavy chain variable region that comprises HCDR1, HCDR2, HCDR3; and a light chain variable region that comprises LCDR1, LCDR2, LCDR3, wherein:
   (a) HCDR1 comprises an amino acid sequence of SEQ ID NO: 43;
   (b) HCDR2 comprises an amino acid sequence of SEQ ID NO:44;
   (c) HCDR3 comprises an amino acid sequence of SEQ ID NO:45;
   (d) LCDR1 comprises an amino acid sequence of SEQ ID NO:48;
   (e) LCDR2 comprises an amino acid sequence of SEQ ID NO:49; and
   (f) LCDR3 comprises an amino acid sequence of SEQ ID NO: 50.

2. The isolated antibody or antigen-binding fragment thereof of claim 1, which comprises:
   a heavy chain variable region (VH) comprising an amino acid sequence which has at least 85% identity to the amino acid sequence of any one of SEQ ID NOs: 41, and 76-78, and comprises HCDR1 comprising SEQ ID NO: 43, HCDR2 comprising SEQ ID NO: 44, and HCDR3 comprising SEQ ID NO: 45; and
   (ii) a light chain variable region (VL) comprising an amino acid sequence which has at least 85% identity to the amino acid sequence of any one of SEQ ID NO: 46, 79 and 80, and comprises LCDR1 comprising SEQ ID NO: 48, LCDR2 comprising SEQ ID NO: 49, and LCDR3 comprising SEQ ID NO: 50.

3. The isolated antibody or antigen-binding fragment thereof of claim 1, which comprises:
   1) a heavy chain variable region (VH) that comprises an amino acid sequence which has at least 85% identity to the amino acid sequences of SEQ ID NO: 41 and comprises HCDR1 comprising SEQ ID NO: 43, HCDR2 comprising SEQ ID NO: 44, and HCDR3 comprising SEQ ID NO: 45, and a light chain variable region (VL) that comprises an amino acid sequence which has at least 85% identity to the amino acid sequences of SEQ ID NO: 46 and comprises LCDR1 comprising SEQ ID NO: 48, LCDR2 comprising SEQ ID NO: 49, and LCDR3 comprising SEQ ID NO: 50;
   2) a heavy chain variable region (VH) that comprises an amino acid sequence which has at least 85% identity to the amino acid sequences of SEQ ID NO: 76 and comprises HCDR1 comprising SEQ ID NO: 43, HCDR2 comprising SEQ ID NO: 44, and HCDR3 comprising SEQ ID NO: 45, and a light chain variable region (VL) that comprises an amino acid sequence which has at least 85% identity to the amino acid sequences of SEQ ID NO: 79 and comprises LCDR1 comprising SEQ ID NO: 48, LCDR2 comprising SEQ ID NO: 49, and LCDR3 comprising SEQ ID NO: 50;
   3) a heavy chain variable region (VH) that comprises an amino acid sequence which has at least 85% identity to the amino acid sequences of SEQ ID NO: 76 and comprises HCDR1 comprising SEQ ID NO: 43, HCDR2 comprising SEQ ID NO: 44, and HCDR3 comprising SEQ ID NO: 45, and a light chain variable region (VL) that comprises an amino acid sequence which has at least 85% identity to the amino acid sequences of SEQ ID NO: 80 and comprises LCDR1 comprising SEQ ID NO: 48, LCDR2 comprising SEQ ID NO: 49, and LCDR3 comprising SEQ ID NO: 50;
   4) a heavy chain variable region (VH) that comprises an amino acid sequence which has at least 85% identity to the amino acid sequences of SEQ ID NO: 77 and comprises HCDR1 comprising SEQ ID NO: 43, HCDR2 comprising SEQ ID NO: 44, and HCDR3 comprising SEQ ID NO: 45, and a light chain variable region (VL) that comprises an amino acid sequence which has at least 85% identity to the amino acid sequences of SEQ ID NO: 79 and comprises LCDR1 comprising SEQ ID NO: 48, LCDR2 comprising SEQ ID NO: 49, and LCDR3 comprising SEQ ID NO: 50;
   5) a heavy chain variable region (VH) that comprises an amino acid sequence which has at least 85% identity to the amino acid sequences of SEQ ID NO: 77 and comprises HCDR1 comprising SEQ ID NO: 43, HCDR2 comprising SEQ ID NO: 44, and HCDR3 comprising SEQ ID NO: 45, and a light chain variable region (VL) that comprises an amino acid sequence which has at least 85% identity to the amino acid sequences of SEQ ID NO: 80 and comprises LCDR1 comprising SEQ ID NO: 48, LCDR2 comprising SEQ ID NO: 49, and LCDR3 comprising SEQ ID NO: 50;
   6) a heavy chain variable region (VH) that comprises an amino acid sequence which has at least 85% identity to the amino acid sequences of SEQ ID NO: 78 and comprises HCDR1 comprising SEQ ID NO: 43, HCDR2 comprising SEQ ID NO: 44, and HCDR3 comprising SEQ ID NO: 45, and a light chain variable region (VL) that comprises an amino acid sequence which has at least 85% identity to the amino acid sequences of SEQ ID NO: 79 and comprises LCDR1 comprising SEQ ID NO: 48, LCDR2 comprising SEQ ID NO: 49, and LCDR3 comprising SEQ ID NO: 50;
   7) a heavy chain variable region (VH) that comprises an amino acid sequence which has at least 85% identity to the amino acid sequences of SEQ ID NO: 78 and comprises HCDR1 comprising SEQ ID NO: 43, HCDR2 comprising SEQ ID NO: 44, and HCDR3 comprising SEQ ID NO: 45, and a light chain variable region (VL) that comprises an amino acid sequence which has at least 85% identity to the amino acid sequences of SEQ ID NO: 80 and comprises LCDR1 comprising SEQ ID NO: 48, LCDR2 comprising SEQ ID NO: 49, and LCDR3 comprising SEQ ID NO: 50.

4. The isolated antibody or antigen-binding fragment thereof of claim 3, which comprises a heavy chain variable region (VH) that comprises an amino acid sequence of SEQ ID NO: 76, and a light chain variable region (VL) that comprises an amino acid sequence of SEQ ID NO: 80.

5. The isolated antibody or antigen-binding fragment thereof of claim 1, wherein the isolated antibody is an IgG.

6. The isolated antibody or antigen-binding fragment thereof of claim 1, wherein the isolated antibody is an IgG1, IgG2 or IgG4.

7. The isolated antibody or antigen-binding fragment thereof of claim 1, wherein the isolated antibody is a monoclonal antibody, a chimeric antibody, a humanized antibody, a human engineered antibody, a human antibody, Fv, a single chain antibody (scFv), Fab, Fab', Fab'-SH or F(ab')$_2$.

8. The isolated antibody or antigen-binding fragment thereof of claim 1, comprising a heavy chain and a light chain, wherein:
   (I) the heavy chain comprising an amino acid sequence which has at least 85% identity to the amino acid sequence selected from the group consisting of SEQ ID NOs: 51, 52, 81, 82, 83, 86, 87, 90, 91, 120, 124, 125, 126 and 127, and comprises HCDR1 comprising SEQ ID NO: 43, HCDR2 comprising SEQ ID NO: 44, and HCDR3 comprising SEQ ID NO: 45; and (II) the light chain comprising an amino acid sequence which has at least 85% identity to the amino acid sequences selected from the group consisting of SEQ ID NOs: 53, 84, 85, 88, 89 and 121, and comprises LCDR1 comprising SEQ ID NO: 48, LCDR2 comprising SEQ ID NO: 49, and LCDR3 comprising SEQ ID NO: 50.

9. The isolated antibody or antigen-binding fragment thereof of claim 1, which comprises:

1) a heavy chain that comprises an amino acid sequence which has at least 85% identity to the amino acid sequences of SEQ ID NO: 51 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 53 and comprises LCDR1 comprising SEQ ID NO: 48, LCDR2 comprising SEQ ID NO: 49, and LCDR3 comprising SEQ ID NO: 50;

2) a heavy chain that comprises an amino acid sequence which has at least 85% identity to the amino acid sequences of SEQ ID NO: 52 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 53 and comprises LCDR1 comprising SEQ ID NO: 48, LCDR2 comprising SEQ ID NO: 49, and LCDR3 comprising SEQ ID NO: 50;

3) a heavy chain that comprises an amino acid sequence which has at least 85% identity to the amino acid sequences of SEQ ID NO: 81 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 84 and comprises LCDR1 comprising SEQ ID NO: 48, LCDR2 comprising SEQ ID NO: 49, and LCDR3 comprising SEQ ID NO: 50;

4) a heavy chain that comprises an amino acid sequence which has at least 85% identity to the amino acid sequences of SEQ ID NO: 81 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 85 and comprises LCDR1 comprising SEQ ID NO: 48, LCDR2 comprising SEQ ID NO: 49, and LCDR3 comprising SEQ ID NO: 50;

5) a heavy chain that comprises an amino acid sequence which has at least 85% identity to the amino acid sequences of SEQ ID NO: 82 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 84 and comprises LCDR1 comprising SEQ ID NO: 48, LCDR2 comprising SEQ ID NO: 49, and LCDR3 comprising SEQ ID NO: 50;

6) a heavy chain that comprises an amino acid sequence which has at least 85% identity to the amino acid sequences of SEQ ID NO: 82 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 85 and comprises LCDR1 comprising SEQ ID NO: 48, LCDR2 comprising SEQ ID NO: 49, and LCDR3 comprising SEQ ID NO: 50;

7) a heavy chain that comprises an amino acid sequence which has at least 85% identity to the amino acid sequences of SEQ ID NO: 83 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 84 and comprises LCDR1 comprising SEQ ID NO: 48, LCDR2 comprising SEQ ID NO: 49, and LCDR3 comprising SEQ ID NO: 50;

8) a heavy chain that comprises an amino acid sequence which has at least 85% identity to the amino acid sequences of SEQ ID NO: 83 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 85 and comprises LCDR1 comprising SEQ ID NO: 48, LCDR2 comprising SEQ ID NO: 49, and LCDR3 comprising SEQ ID NO: 50;

9) a heavy chain that comprises an amino acid sequence which has at least 85% identity to the amino acid sequences of SEQ ID NO: 90 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 84 and comprises LCDR1 comprising SEQ ID NO: 48, LCDR2 comprising SEQ ID NO: 49, and LCDR3 comprising SEQ ID NO: 50;

10) a heavy chain that comprises an amino acid sequence which has at least 85% identity to the amino acid sequences of SEQ ID NO: 90 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 85 and comprises LCDR1 comprising SEQ ID NO: 48, LCDR2 comprising SEQ ID NO: 49, and LCDR3 comprising SEQ ID NO: 50;

11) a heavy chain that comprises an amino acid sequence which has at least 85% identity to the amino acid sequences of SEQ ID NO: 91 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 84 and comprises LCDR1 comprising SEQ ID NO: 48, LCDR2 comprising SEQ ID NO: 49, and LCDR3 comprising SEQ ID NO: 50;

12) a heavy chain that comprises an amino acid sequence which has at least 85% identity to the amino acid sequences of SEQ ID NO: 91 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 85 and comprises LCDR1 comprising SEQ ID NO: 48, LCDR2 comprising SEQ ID NO: 49, and LCDR3 comprising SEQ ID NO: 50;

13) a heavy chain that comprises an amino acid sequence which has at least 85% identity to the amino acid sequences of SEQ ID NO: 86 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 88 and comprises LCDR1 comprising SEQ ID NO: 48, LCDR2 comprising SEQ ID NO: 49, and LCDR3 comprising SEQ ID NO: 50;

14) a heavy chain that comprises an amino acid sequence which has at least 85% identity to the amino acid sequences of SEQ ID NO: 86 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 89 and comprises LCDR1 comprising SEQ ID NO: 48, LCDR2 comprising SEQ ID NO: 49, and LCDR3 comprising SEQ ID NO: 50;

15) a heavy chain that comprises an amino acid sequence which has at least 85% identity to the amino acid sequences of SEQ ID NO: 87 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 88 and comprises LCDR1 comprising SEQ ID NO: 48, LCDR2 comprising SEQ ID NO: 49, and LCDR3 comprising SEQ ID NO: 50;

16) a heavy chain that comprises an amino acid sequence which has at least 85% identity to the amino acid sequences of SEQ ID NO: 87 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 89 and comprises LCDR1 comprising SEQ ID NO: 48, LCDR2 comprising SEQ ID NO: 49, and LCDR3 comprising SEQ ID NO: 50;

17) a heavy chain that comprises an amino acid sequence which has at least 85% identity to the amino acid sequences of SEQ ID NO: 124 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 84 and comprises LCDR1 comprising SEQ ID NO: 48, LCDR2 comprising SEQ ID NO: 49, and LCDR3 comprising SEQ ID NO: 50;

18) a heavy chain that comprises an amino acid sequence which has at least 85% identity to the amino acid sequences of SEQ ID NO: 124 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 85 and comprises LCDR1 comprising SEQ ID NO: 48, LCDR2 comprising SEQ ID NO: 49, and LCDR3 comprising SEQ ID NO: 50;

19) a heavy chain that comprises an amino acid sequence which has at least 85% identity to the amino acid sequences of SEQ ID NO: 125 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 84 and comprises LCDR1 comprising SEQ ID NO: 48, LCDR2 comprising SEQ ID NO: 49, and LCDR3 comprising SEQ ID NO: 50; or 20) a heavy chain that comprises an amino acid sequence which has at least 85% identity to the amino acid sequences of SEQ ID NO: 125 and comprises HCDR1 comprising SEQ ID NO: 43, HCDR2 comprising SEQ ID NO: 44, and HCDR3 comprising SEQ ID NO: 45, and a light chain that comprises an amino acid sequence which has at least 85% identity to the amino acid sequence of SEQ ID NO: 85 and comprises LCDR1 comprising SEQ ID NO: 48, LCDR2 comprising SEQ ID NO: 49, and LCDR3 comprising SEQ ID NO: 50.

10. The isolated antibody or antigen-binding fragment thereof of claim 9, which comprises
1) a heavy chain consisting of SEQ ID NO: 81 and a light chain consisting of SEQ ID NO: 85;
2) a heavy chain consisting of SEQ ID NO: 82 and a light chain consisting of SEQ ID NO: 84;
3) a heavy chain consisting of SEQ ID NO: 83 and a light chain consisting of SEQ ID NO: 85;
4) a heavy chain consisting of SEQ ID NO: 124 and a light chain consisting of SEQ ID NO: 85; or
5) a heavy chain consisting of SEQ ID NO: 125 and a light chain consisting of SEQ ID NO: 85.

11. The isolated antibody or antigen-binding fragment thereof of claim 1, which is an antagonist of CD73 or an antagonist of 5'-nucleotidase of CD73.

12. The isolated antibody or antigen-binding fragment thereof of claim 11, wherein the CD73 is human CD73.

13. A method of decreasing adenosine levels in a subject with tumor, improving a T cell response in a subject with tumor, stimulating an immune response in a subject, or inhibiting the growth of tumor cells in a subject, said method comprises administering a therapeutically effective amount of the isolated antibody or antigen-binding fragment thereof of claim 1 to the subject.

14. The method of claim 13, wherein the subject is the subject with tumor.

15. The method of claim 13, wherein the subject has a tumor cell expressing CD73 and/or a tumor microenvironment containing CD73.

16. A pharmaceutical composition comprising the isolated antibody or antigen-binding fragment thereof of claim 1, and a pharmaceutically acceptable excipient.

17. A method of treating tumor comprising administering a subject in need a therapeutically effective amount of the isolated antibody or antigen-binding fragment thereof of claim 1, or a pharmaceutical composition comprising said isolated antibody or antigen-binding fragment thereof.

18. The method of claim 17, wherein the tumor is selected from solid tumor or hematological tumor.

19. The method of claim 17, wherein the tumor is selected from bladder cancer, breast cancer, cervical cancer, ovarian cancer, prostate cancer, testicular cancer, esophageal cancer, gastrointestinal cancer, pancreatic cancer, colorectal cancer, colon cancer, renal cancer, head and neck cancer, lung cancer (small cell lung cancer or non-small cell lung cancer), stomach cancer, bone cancer, liver cancer, thyroid cancer, skin cancer, central nervous system tumor, lymphoma, leukemia, myeloma, sarcoma, and virus-associated cancer.

* * * * *

SEQUENCE LISTING

```
<160> NUMBER OF SEQ ID NOS: 127

<210> SEQ ID NO 1
<211> LENGTH: 532
<212> TYPE: PRT
<213> ORGANISM: Homo sapiens

<400> SEQUENCE: 1

Trp Glu Leu Thr Ile Leu His Thr Asn Asp Val His Ser Arg Leu Glu
1               5                  10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140
```

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
            165                 170                 175

Glu Val Asp Lys Leu Lys Thr Leu Asn Val Asn Lys Ile Ile Ala Leu
        180                 185                 190

Gly His Ser Gly Phe Glu Met Asp Lys Leu Ile Ala Gln Lys Val Arg
    195                 200                 205

Gly Val Asp Val Val Gly Gly His Ser Asn Thr Phe Leu Tyr Thr
210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Gln Ala Tyr Ala
            245                 250                 255

Phe Gly Lys Tyr Leu Gly Tyr Leu Lys Ile Glu Phe Asp Glu Arg Gly
        260                 265                 270

Asn Val Ile Ser Ser His Gly Asn Pro Ile Leu Leu Asn Ser Ser Ile
    275                 280                 285

Pro Glu Asp Pro Ser Ile Lys Ala Asp Ile Asn Lys Trp Arg Ile Lys
290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
            325                 330                 335

Leu Ile Cys Asp Ala Met Ile Asn Asn Leu Arg His Thr Asp Glu
        340                 345                 350

Met Phe Trp Asn His Val Ser Met Cys Ile Leu Asn Gly Gly Gly Ile
    355                 360                 365

Arg Ser Pro Ile Asp Glu Arg Asn Asn Gly Thr Ile Thr Trp Glu Asn
370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
            405                 410                 415

Gly Gln Ser Thr Gly Glu Phe Leu Gln Val Gly Gly Ile His Val Val
        420                 425                 430

Tyr Asp Leu Ser Arg Lys Pro Gly Asp Arg Val Val Lys Leu Asp Val
    435                 440                 445

Leu Cys Thr Lys Cys Arg Val Pro Ser Tyr Asp Pro Leu Lys Met Asp
450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
            485                 490                 495

Gln Asp Ile Asn Val Val Ser Thr Tyr Ile Ser Lys Met Lys Val Ile
    500                 505                 510

Tyr Pro Ala Val Glu Gly Arg Ile Lys Ala His His His His His
515                 520                 525

His His His His
    530

<210> SEQ ID NO 2
<211> LENGTH: 532

<212> TYPE: PRT
<213> ORGANISM: Macaca fascicularis

<400> SEQUENCE: 2

```
Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Thr Asp Lys Leu Ile Ala Gln Lys Val Arg
        195                 200                 205

Gly Val Asp Val Val Gly Gly His Ser Asn Thr Phe Leu Tyr Thr
210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
        275                 280                 285

Pro Glu Asp Pro Ser Ile Lys Ala Asp Ile Asn Lys Trp Arg Ile Lys
290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Ala Asp Glu
            340                 345                 350

Met Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
370                 375                 380

Leu Ala Ala Val Leu Pro Phe Gly Gly Thr Phe Asp Leu Val Gln Leu
385                 390                 395                 400
```

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
        435                 440                 445

Leu Cys Thr Lys Cys Arg Val Pro Ser Tyr Asp Pro Leu Lys Met Asp
    450                 455                 460

Glu Ile Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys Ala His His His His His His
        515                 520                 525

His His His His
    530

<210> SEQ ID NO 3
<211> LENGTH: 121
<212> TYPE: PRT
<213> ORGANISM: Artificial Sequence
<220> FEATURE:
<223> OTHER INFORMATION: synthetic polypeptide

<400> SEQUENCE: 3

Glu Val Gln Leu Lys Glu Ser Gly Ala Glu Leu Val Lys Pro Gly Ala
1               5                   10                  15

Ser Val Lys Ile Ser Cys Lys Ala Thr Gly Tyr Thr Phe Thr Gly Tyr
            20                  25                  30

Trp Ile Glu Trp Val Lys Gln Arg Pro Gly Arg Gly Leu Glu Trp Ile
        35                  40                  45

Gly Glu Ile Leu Pro Gly Ser Asp Ile Thr Asn Tyr Asn Glu Lys Phe
    50                  55                  60

Lys Gly Lys Ala Thr Ile Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg Arg Gly Tyr Asp Glu Thr Gly Tyr Ala Met Asp Tyr Trp Gly
            100                 105                 110

Gln Gly Thr Ser Val Thr Val Ser Ser
        115                 120

<210> SEQ ID NO 4
<211> LENGTH: 363
<212> TYPE: DNA
<213> ORGANISM: Artificial Sequence
<220> FEATURE:
<223> OTHER INFORMATION: synthetic polynucleotide

<400> SEQUENCE: 4
gaggtgcagc tgaaggagtc tggggctgag ctggtgaagc ctggggcctc agtgaagatt      60
tcctgcaaag ctactggcta tacattcact ggctactgga tagagtgggt aaagcagagg     120
cctggacgtg gccttgagtg gattggagag attttacctg gaagtgatat tactaactac     180
aatgagaagt tcaagggcaa ggccacaatc actgcagata catcctccaa cacagcctac     240

```
atgcaactca gcagcctgac aactgaggac tctgccatct attactgtgc aagaaggggt    300
tacgacgaga cgggctatgc tatggactac tggggtcaag gaacctcagt cacagtctcc    360
tca                                                                  363
```

<210> SEQ ID NO 5
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 5

Gly Tyr Trp Ile Glu
1               5

<210> SEQ ID NO 6
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 6

Glu Ile Leu Pro Gly Ser Asp Ile Thr Asn Tyr Asn Glu Lys Phe Lys
1               5                   10                  15

Gly

<210> SEQ ID NO 7
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 7

Arg Gly Tyr Asp Glu Thr Gly Tyr Ala Met Asp Tyr
1               5                   10

<210> SEQ ID NO 8
<211> LENGTH: 111
<212> TYPE: PRT
<213> ORGANISM: Artificial Sequence
<220> FEATURE:
<223> OTHER INFORMATION: synthetic polypeptide

<400> SEQUENCE: 8

Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile His Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Val Tyr Phe Cys Gln Gln Ser Lys
                85                  90                  95

Glu Val Pro Trp Thr Phe Gly Glu Gly Thr Lys Leu Glu Ile Lys
            100                 105                 110

<210> SEQ ID NO 9
<211> LENGTH: 333
<212> TYPE: DNA
<213> ORGANISM: Artificial Sequence
<220> FEATURE:
<223> OTHER INFORMATION: synthetic polynucleotide

<400> SEQUENCE: 9

```
gacattgtga tgacccaatc tccagcttct ttggctgtgt ctctagggca gagggccacc      60
atctcctgca aggccagcca agtgttgat tatgatggtg atagctatat gaactggtac     120
caacagaaac caggacagcc acccaaactc ctcatccatg ctgcatccaa tctagaatct     180
gggatcccag ccaggtttag tggcagtggg tctgggacag acttcaccct caacatccat     240
cctgtggagg aagaggatgc tgcagtgtat ttctgtcagc aaagtaagga ggttccgtgg     300
acgttcgtgg aagggaccaa gctggaaatc aaa                                  333
```

<210> SEQ ID NO 10
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 10

```
Lys Ala Ser Gln Ser Val Asp Tyr Asp Gly Asp Ser Tyr Met Asn
1               5                   10                  15
```

<210> SEQ ID NO 11
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 11

```
Ala Ala Ser Asn Leu Glu Ser
1               5
```

<210> SEQ ID NO 12
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 12

```
Gln Gln Ser Lys Glu Val Pro Trp Thr
1               5
```

<210> SEQ ID NO 13
<211> LENGTH: 451
<212> TYPE: PRT
<213> ORGANISM: Artificial Sequence
<220> FEATURE:
<223> OTHER INFORMATION: synthetic polypeptide

<400> SEQUENCE: 13

```
Glu Val Gln Leu Lys Glu Ser Gly Ala Glu Leu Val Lys Pro Gly Ala
1               5                   10                  15

Ser Val Lys Ile Ser Cys Lys Ala Thr Gly Tyr Thr Phe Thr Gly Tyr
            20                  25                  30

Trp Ile Glu Trp Val Lys Gln Arg Pro Gly Arg Gly Leu Glu Trp Ile
        35                  40                  45
```

```
Gly Glu Ile Leu Pro Gly Ser Asp Ile Thr Asn Tyr Asn Glu Lys Phe
    50                  55                  60
Lys Gly Lys Ala Thr Ile Thr Ala Asp Thr Ser Ser Asn Thr Ala Tyr
65                  70                  75                  80
Met Gln Leu Ser Ser Leu Thr Thr Glu Asp Ser Ala Ile Tyr Tyr Cys
                85                  90                  95
Ala Arg Arg Gly Tyr Asp Glu Thr Gly Tyr Ala Met Asp Tyr Trp Gly
            100                 105                 110
Gln Gly Thr Ser Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450
```

```
<210> SEQ ID NO 14
<211> LENGTH: 218
<212> TYPE: PRT
<213> ORGANISM: Artificial Sequence
<220> FEATURE:
<223> OTHER INFORMATION: synthetic polypeptide

<400> SEQUENCE: 14

Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile His Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Val Tyr Phe Cys Gln Gln Ser Lys
                85                  90                  95

Glu Val Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 15
<211> LENGTH: 447
<212> TYPE: PRT
<213> ORGANISM: Artificial Sequence
<220> FEATURE:
<223> OTHER INFORMATION: synthetic polypeptide

<400> SEQUENCE: 15

Glu Val Gln Leu Lys Glu Ser Gly Ala Glu Leu Val Lys Pro Gly Ala
1               5                   10                  15

Ser Val Lys Ile Ser Cys Lys Ala Thr Gly Tyr Thr Phe Thr Gly Tyr
            20                  25                  30

Trp Ile Glu Trp Val Lys Gln Arg Pro Gly Arg Gly Leu Glu Trp Ile
        35                  40                  45

Gly Glu Ile Leu Pro Gly Ser Asp Ile Thr Asn Tyr Asn Glu Lys Phe
    50                  55                  60

Lys Gly Lys Ala Thr Ile Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95
```

Ala Arg Arg Gly Tyr Asp Glu Thr Gly Tyr Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 16
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 16

Gln Val Gln Leu Gln Gln Ser Gly Leu Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
         35                  40                  45

Gly Tyr Ile Lys Pro His Asn Gly Gly Thr Thr Tyr Asn Pro Lys Phe
     50                  55                  60

Glu Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
             85                  90                  95

Val Arg Cys Asp Phe Leu Tyr Trp Tyr Phe Asp Val Trp Gly Thr Gly
            100                 105                 110

Thr Thr Val Thr Val Ser Ser
            115

<210> SEQ ID NO 17
<211> LENGTH: 357
<212> TYPE: DNA
<213> ORGANISM: Artificial Sequence
<220> FEATURE:
<223> OTHER INFORMATION: synthetic polynucleotide

<400> SEQUENCE: 17
caggtccaac tgcagcagtc tggacttgag ctggtgaagc ctggggcttc agtgaagatg      60
tcctgcaagg cttctggata cacattcact gactacaaca tgcactgggt gaagcagagc     120
catggaaaga gccttgagtg gattggatat attaagcctc acaatggtgg tactacctac     180
aacccgaagt tcgagggcaa ggccacattg actgtaaaca gtcttccag cacagcctac      240 atggagctcc gcagcctgac atcggaggat tctgcagtct attactgtgt aagatgcgat     300
tttctctact ggtatttcga tgtctgggc acagggacca cggtcaccgt ctcctca        357

<210> SEQ ID NO 18
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 18

Asp Tyr Asn Met His
1               5

<210> SEQ ID NO 19
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 19

Tyr Ile Lys Pro His Asn Gly Gly Thr Thr Tyr Asn Pro Lys Phe Glu
1               5                   10                  15

Gly

<210> SEQ ID NO 20
<211> LENGTH: 10
<212> TYPE: PRT
<213> ORGANISM: Artificial Sequence
<220> FEATURE:
<223> OTHER INFORMATION: synthetic polypeptide -continued

<400> SEQUENCE: 20

Cys Asp Phe Leu Tyr Trp Tyr Phe Asp Val
1               5                   10

<210> SEQ ID NO 21
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 21

Asp Ile Val Met Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Leu Thr Phe Gly Ala Gly Thr Lys Leu Glu Met Lys
            100                 105

<210> SEQ ID NO 22
<211> LENGTH: 324
<212> TYPE: DNA
<213> ORGANISM: Artificial Sequence
<220> FEATURE:
<223> OTHER INFORMATION: synthetic polynucleotide

<400> SEQUENCE: 22
gacattgtga tgacccagtc tccagcaatc atgtctgcat ctctagggga acgggtcacc    60
atgacctgca ctgccagctc aagtgtaagt tccagttact tgcactggta ccagcagaag   120
ccaggatcct cccccaaact ctggatttat agcacatcca acctggcttc tggagtccca   180
ggtcgcttca gtggcagtgg gtctgggacc tcttactctc tcacaatcag cagcatggag   240
gctgaagatg ctgccactta ttactgccac cagtatcatc gttccccgct cacgttcggt   300
gctgggacca agctggaaat gaaa                                          324

<210> SEQ ID NO 23
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 23

Thr Ala Ser Ser Ser Val Ser Ser Ser Tyr Leu His
1               5                   10

<210> SEQ ID NO 24
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 24

Ser Thr Ser Asn Leu Ala Ser
1               5

<210> SEQ ID NO 25
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 25

His Gln Tyr His Arg Ser Pro Leu Thr
1               5

<210> SEQ ID NO 26
<211> LENGTH: 449
<212> TYPE: PRT
<213> ORGANISM: Artificial Sequence
<220> FEATURE:
<223> OTHER INFORMATION: synthetic polypeptide

<400> SEQUENCE: 26

Gln Val Gln Leu Gln Gln Ser Gly Leu Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Asn Met His Trp Val Lys Gln Ser His Gly Lys Ser Leu Glu Trp Ile
            35                  40                  45

Gly Tyr Ile Lys Pro His Asn Gly Gly Thr Thr Tyr Asn Pro Lys Phe
        50                  55                  60

Glu Gly Lys Ala Thr Leu Thr Val Asn Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Val Arg Cys Asp Phe Leu Tyr Trp Tyr Phe Asp Val Trp Gly Thr Gly
                100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 27
<211> LENGTH: 445
<212> TYPE: PRT
<213> ORGANISM: Artificial Sequence
<220> FEATURE:
<223> OTHER INFORMATION: synthetic polypeptide

<400> SEQUENCE: 27

Gln Val Gln Leu Gln Gln Ser Gly Leu Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Lys Pro His Asn Gly Gly Thr Thr Tyr Asn Pro Lys Phe
    50                  55                  60

Glu Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Val Arg Cys Asp Phe Leu Tyr Trp Tyr Phe Asp Val Trp Gly Thr Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 28
<211> LENGTH: 215
<212> TYPE: PRT
<213> ORGANISM: Artificial Sequence
<220> FEATURE:
<223> OTHER INFORMATION: synthetic polypeptide

<400> SEQUENCE: 28

Asp Ile Val Met Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95
```

```
Leu Thr Phe Gly Ala Gly Thr Lys Leu Glu Met Lys Arg Thr Val Ala
                100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 29
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 29

Gln Val His Leu Gln Gln Ser Gly Ala Glu Leu Ala Lys Pro Gly Ala
1               5                   10                  15

Ser Val Asn Leu Ser Cys Lys Ala Ser Gly Tyr Ala Phe Thr Ser Tyr
                20                  25                  30

Trp Met His Trp Val Lys Gln Arg Pro Gly Gln Gly Leu Glu Trp Ile
            35                  40                  45

Gly Tyr Ile Asn Pro Ser Ser Gly Leu Ala Lys Tyr Asn Gln Lys Phe
        50                  55                  60

Lys Asp Lys Ala Thr Leu Thr Thr Asp Lys Ser Ser Asn Thr Ala Tyr
65                  70                  75                  80

Met Gln Leu Ser Ser Leu Thr Tyr Asp Asp Ser Ala Val Tyr Tyr Cys
                85                  90                  95

Gly Arg Trp Leu Leu Ser Ala Trp Phe Ala Tyr Trp Gly Gln Gly Thr
            100                 105                 110

Leu Val Thr Val Ser Ala
        115

<210> SEQ ID NO 30
<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 30
caggtccacc tgcagcagtc tggggctgaa ctggcaaaac ctggggcctc agtgaacctg      60
tcctgcaagg cttctggcta cgcctttact agttactgga tgcactgggt aaaacagagg     120
cctggacagg gtctggaatg gattggatac attaatccta gcagtggtct tgctaagtat     180
aatcagaagt tcaaagacaa ggccacattg actacagaca atcttccaa cacagcctac      240 atgcaactga gcagcctgac atatgacgac tctgcagtct attactgtgg aagatggtta    300
ctttcggcct ggtttgctta ctggggccaa gggactctgg tcactgtctc tgca          354
```

<210> SEQ ID NO 31
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 31

Ser Tyr Trp Met His
1               5

<210> SEQ ID NO 32
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 32

Tyr Ile Asn Pro Ser Ser Gly Leu Ala Lys Tyr Asn Gln Lys Phe Lys
1               5                   10                  15

Asp

<210> SEQ ID NO 33
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 33

Trp Leu Leu Ser Ala Trp Phe Ala Tyr
1               5

<210> SEQ ID NO 34
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 34

Asp Ile Lys Met Thr Gln Ser Pro Ser Ser Ile Tyr Ala Ser Leu Gly
1               5                   10                  15

Glu Arg Val Thr Ile Thr Cys Lys Ala Ser Gln Gly Ile Asn Thr Tyr
                20                  25                  30

Leu Ser Trp Phe Gln Gln Lys Pro Gly Lys Ser Pro Lys Thr Leu Ile
            35                  40                  45

Tyr Arg Ala Asn Ile Leu Val Asp Gly Val Pro Ser Arg Phe Ser Gly
        50                  55                  60

Ser Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 35
<211> LENGTH: 321
<212> TYPE: DNA
<213> ORGANISM: Artificial Sequence
<220> FEATURE:

<223> OTHER INFORMATION: synthetic polynucleotide

<400> SEQUENCE: 35

```
gacatcaaga tgacccagtc tccatcttcc atatatgcat ctctaggaga gagagtcact    60
atcacttgca aggcgagtca gggcattaat acctatttaa gctggttcca gcagaaacca   120
ggaaaatctc ctaagaccct gatctatcgt gcaaacatct tggtagatgg ggtcccatca   180
aggttcagtg gcagtggatc tgggcaagat tattctctca ccatcaacag cctggagtat   240
gaagatatgg gaatttatta ttgtctacag tatgatgagt ttccgtacac gttcggaggg   300
gggaccaagc tggaaataaa a                                             321
```

<210> SEQ ID NO 36
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 36

```
Lys Ala Ser Gln Gly Ile Asn Thr Tyr Leu Ser
1               5                   10
```

<210> SEQ ID NO 37
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 37

```
Arg Ala Asn Ile Leu Val Asp
1               5
```

<210> SEQ ID NO 38
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 38

```
Leu Gln Tyr Asp Glu Phe Pro Tyr Thr
1               5
```

<210> SEQ ID NO 39
<211> LENGTH: 444
<212> TYPE: PRT
<213> ORGANISM: Artificial Sequence
<220> FEATURE:
<223> OTHER INFORMATION: synthetic polypeptide

<400> SEQUENCE: 39

```
Gln Val His Leu Gln Gln Ser Gly Ala Glu Leu Ala Lys Pro Gly Ala
1               5                   10                  15

Ser Val Asn Leu Ser Cys Lys Ala Ser Gly Tyr Ala Phe Thr Ser Tyr
                20                  25                  30

Trp Met His Trp Val Lys Gln Arg Pro Gly Gln Gly Leu Glu Trp Ile
            35                  40                  45

Gly Tyr Ile Asn Pro Ser Ser Gly Leu Ala Lys Tyr Asn Gln Lys Phe
        50                  55                  60

Lys Asp Lys Ala Thr Leu Thr Thr Asp Lys Ser Ser Asn Thr Ala Tyr
65                  70                  75                  80
```

```
Met Gln Leu Ser Ser Leu Thr Tyr Asp Asp Ser Ala Val Tyr Tyr Cys
                85                  90                  95

Gly Arg Trp Leu Leu Ser Ala Trp Phe Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 40
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 40
```

```
Asp Ile Lys Met Thr Gln Ser Pro Ser Ser Ile Tyr Ala Ser Leu Gly
 1               5                  10                  15

Glu Arg Val Thr Ile Thr Cys Lys Ala Ser Gln Gly Ile Asn Thr Tyr
            20                  25                  30

Leu Ser Trp Phe Gln Lys Pro Gly Lys Ser Pro Lys Thr Leu Ile
        35                  40                  45

Tyr Arg Ala Asn Ile Leu Val Asp Gly Val Pro Ser Arg Phe Ser Gly
 50                  55                  60

Ser Gly Ser Gly Gln Asp Tyr Ser Leu Thr Ile Asn Ser Leu Glu Tyr
 65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 41
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 41

Gln Val Gln Leu Gln Gln Ser Gly Ala Glu Leu Ala Lys Pro Gly Ala
 1               5                  10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Ser Gly Tyr Thr Lys Ser Asn Gln Lys Phe
 50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Tyr Glu Asp Ser Ala Val Tyr Tyr Cys
                85                  90                  95

Gly Arg Trp Leu Leu Ser Ala Trp Phe Ala Tyr Trp Gly Gln Gly Thr
                100                 105                 110

Leu Val Thr Val Ser Ala
        115

<210> SEQ ID NO 42
```

<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 42

```
caggtccagc tgcagcagtc tggggctgaa ctggcaaaac ctggggcctc agtgaagctg      60
tcctgcaagg cttctggcta cacctttact agttactgga tgcactgggt aaaacagagg     120
cctggacagg gtctggaatg gattggatac attaatccta gcagtggtta tactaagtcc     180
aatcagaagt tcaaggacaa ggccacattg actgcagaca atcctccag cacagcctac     240
atgcagctga gcagcctgac atatgaggac tctgcagtct attactgtgg aagatggtta   300
ctttcggcct ggtttgctta ctggggccaa gggactctgg tcactgtctc tgca          354
```

<210> SEQ ID NO 43
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 43

Ser Tyr Trp Met His
1               5

<210> SEQ ID NO 44
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 44

Tyr Ile Asn Pro Ser Ser Gly Tyr Thr Lys Ser Asn Gln Lys Phe Lys
1               5                   10                  15

Asp

<210> SEQ ID NO 45
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 45

Trp Leu Leu Ser Ala Trp Phe Ala Tyr
1               5

<210> SEQ ID NO 46
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 46

Asp Ile Arg Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Thr Tyr
                20                  25                  30

Leu Ser Trp Phe Gln Gln Lys Pro Gly Lys Ser Pro Lys Ser Leu Ile
            35                  40                  45

-continued

```
Tyr Arg Ser Asn Ile Leu Val Asp Gly Val Pro Ser Arg Phe Ser Gly
        50                   55                  60

Ser Gly Ser Gly Gln Asp Tyr Ser Leu Thr Ile Ser Ser Leu Glu Tyr
 65              70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys
            100                 105

<210> SEQ ID NO 47
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 47
gacatcagga tgacccagtc tccatcttcc atgtatgcat ctctaggaga gagagtcact    60
atcacttgca aggcgagtca ggacattaat acctatttaa gctggttcca gcagaaacca   120
ggaaaatctc ctaagtccct gatctatcgc tcaaacatct tggtagatgg ggtcccatca   180
agattcagtg gcagtggatc tggtcaagat tattctctca ccatcagcag cctggagtat   240
gaggatatgg gaatttatta ttgtctacag tatgatgact ttccgtacac gttcggaggg   300
gggaccaagc tggaaataaa a                                             321

<210> SEQ ID NO 48
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 48

Lys Ala Ser Gln Asp Ile Asn Thr Tyr Leu Ser
 1               5                  10

<210> SEQ ID NO 49
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 49

Arg Ser Asn Ile Leu Val Asp
 1               5

<210> SEQ ID NO 50
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 50

Leu Gln Tyr Asp Asp Phe Pro Tyr Thr
 1               5

<210> SEQ ID NO 51
<211> LENGTH: 444
<212> TYPE: PRT
<213> ORGANISM: Artificial Sequence
```

<220> FEATURE:
<223> OTHER INFORMATION: synthetic polypeptide

<400> SEQUENCE: 51

```
Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Ser Gly Tyr Thr Lys Ser Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Tyr Glu Asp Ser Ala Val Tyr Tyr Cys
                85                  90                  95

Gly Arg Trp Leu Leu Ser Ala Trp Phe Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400
```

```
Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 52
<211> LENGTH: 448
<212> TYPE: PRT
<213> ORGANISM: Artificial Sequence
<220> FEATURE:
<223> OTHER INFORMATION: synthetic polypeptide

<400> SEQUENCE: 52

Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Ser Gly Tyr Thr Lys Ser Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Tyr Glu Asp Ser Ala Val Tyr Tyr Cys
                85                  90                  95

Gly Arg Trp Leu Leu Ser Ala Trp Phe Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 53
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 53

Asp Ile Arg Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Thr Tyr
            20                  25                  30

Leu Ser Trp Phe Gln Gln Lys Pro Gly Lys Ser Pro Lys Ser Leu Ile
        35                  40                  45

Tyr Arg Ser Asn Ile Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Asp Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 54
```

<211> LENGTH: 119
<212> TYPE: PRT
<213> ORGANISM: Artificial Sequence
<220> FEATURE:
<223> OTHER INFORMATION: synthetic polypeptide

<400> SEQUENCE: 54

Gln Val Gln Leu Lys Glu Ser Gly Pro Gly Leu Val Ala Pro Ser Gln
1               5                   10                  15
Ser Leu Ser Ile Thr Cys Thr Val Ser Gly Phe Ser Leu Thr Asn Tyr
            20                  25                  30
Gly Val His Trp Val Arg Gln Pro Pro Gly Lys Gly Leu Glu Trp Leu
        35                  40                  45
Gly Val Ile Trp Ala Gly Gly Ser Thr Asn Tyr Asn Ser Ala Leu Met
    50                  55                  60
Ser Arg Leu Ser Ile Ser Lys Asp Asn Ser Lys Ser Gln Leu Phe Leu
65                  70                  75                  80
Lys Met Asn Ser Leu Gln Ala Asp Asp Thr Ala Met Tyr Tyr Cys Ala
                85                  90                  95
Arg Glu Arg Gly Ser Ser Trp Gly Thr Met Asp Tyr Trp Gly Gln Gly
            100                 105                 110
Thr Ser Val Thr Val Ser Ser
        115

<210> SEQ ID NO 55
<211> LENGTH: 357
<212> TYPE: DNA
<213> ORGANISM: Artificial Sequence
<220> FEATURE:
<223> OTHER INFORMATION: synthetic polynucleotide

<400> SEQUENCE: 55
caggtgcagc tgaaggagtc aggacctggc ctggtggcgc cctcacagag cctgtccatc      60
acttgcactg tctctgggtt ttcattaacc aactatggtg tacactgggt tcgccagcct    120
ccaggaaagg gtctggagtg gctgggagta atatgggctg gtggaagcac aaattataat    180
tcggctctca tgtccagact gagcatcagc aaagacaact ccaagagcca acttttctta    240
aaaatgaaca gtctgcaagc tgatgacaca gccatgtact actgtgccag agagaggggt    300
agtagctggg ggactatgga ctactggggt caaggaacct cagtcactgt ctcctca      357

<210> SEQ ID NO 56
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 56

Asn Tyr Gly Val His
1               5

<210> SEQ ID NO 57
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 57

Val Ile Trp Ala Gly Gly Ser Thr Asn Tyr Asn Ser Ala Leu Met Ser
1               5                   10                  15

<210> SEQ ID NO 58
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 58

```
Glu Arg Gly Ser Ser Trp Gly Thr Met Asp Tyr
1               5                   10
```

<210> SEQ ID NO 59
<211> LENGTH: 106
<212> TYPE: PRT
<213> ORGANISM: Artificial Sequence
<220> FEATURE:
<223> OTHER INFORMATION: synthetic polypeptide

<400> SEQUENCE: 59

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Val Ser Tyr Met
                20                  25                  30

His Trp Tyr Gln Gln Lys Ser Gly Thr Ser Pro Lys Arg Trp Ile Tyr
            35                  40                  45

Asp Thr Ser Gln Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Gly Thr Lys Leu Glu Met Arg
            100                 105
```

<210> SEQ ID NO 60
<211> LENGTH: 318
<212> TYPE: DNA
<213> ORGANISM: Artificial Sequence
<220> FEATURE:
<223> OTHER INFORMATION: synthetic polynucleotide

<400> SEQUENCE: 60

```
caaattgttc tcacccagtc tccagcaatc atgtctgcat ctccagggga gaaggtcacc      60
atgacctgca gtgccagctc acgtgtaagt tacatgcact ggtaccagca gaagtcaggc     120
acctccccca aaagatggat ttatgacaca tcccaactgg cttctggagt ccctgctcgc     180
ttcagtggca gtgggtctgg gacctcttac tctctcacaa tcagcagcat ggaggctgaa     240
gatgctgcca cttattactg ccagcagtgg agtagtaacc catacacgtt cggagggggg     300
accaagctgg aaatgaga                                                   318
```

<210> SEQ ID NO 61
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 61

```
Ser Ala Ser Ser Arg Val Ser Tyr Met His
1               5                   10
```

<210> SEQ ID NO 62
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 62

```
Asp Thr Ser Gln Leu Ala Ser
1               5
```

<210> SEQ ID NO 63
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 63

```
Gln Gln Trp Ser Ser Asn Pro Tyr Thr
1               5
```

<210> SEQ ID NO 64
<211> LENGTH: 445
<212> TYPE: PRT
<213> ORGANISM: Artificial Sequence
<220> FEATURE:
<223> OTHER INFORMATION: synthetic polypeptide

<400> SEQUENCE: 64

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Leu Phe Leu
65                  70                  75                  80

Lys Met Asn Ser Leu Gln Ala Asp Asp Thr Ala Met Tyr Tyr Cys Ala
                85                  90                  95

Arg Glu Arg Gly Ser Ser Trp Gly Thr Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220
```

Cys Pro Pro Cys Pro Ala Pro Pro Val Ala Gly Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
        260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 65
<211> LENGTH: 213
<212> TYPE: PRT
<213> ORGANISM: Artificial Sequence
<220> FEATURE:
<223> OTHER INFORMATION: synthetic polypeptide

<400> SEQUENCE: 65

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Val Ser Tyr Met
            20                  25                  30

His Trp Tyr Gln Gln Lys Ser Gly Thr Ser Pro Lys Arg Trp Ile Tyr
        35                  40                  45

Asp Thr Ser Gln Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Gly Thr Lys Leu Glu Met Arg Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 66
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 66

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Arg Gln Ser Pro Gly Lys Ser Leu Glu Trp Ile
        35                  40                  45

Gly Tyr Ile Lys Pro His Asn Ala Gly Thr Thr Tyr Asn Pro Lys Phe
    50                  55                  60

Glu Gly Arg Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Val Arg Ser Asp Phe Leu Tyr Trp Tyr Phe Asp Val Trp Gly Gln Gly
            100                 105                 110

Thr Thr Val Thr Val Ser Ser
        115

<210> SEQ ID NO 67
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 67

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Lys Pro His Asn Ala Gly Thr Thr Tyr Asn Pro Lys Phe
    50                  55                  60

Glu Gly Arg Ala Thr Leu Thr Val Asp Thr Ser Ala Ser Thr Ala Tyr
65                  70                  75                  80

Met Glu Leu Arg Ser Leu Arg Ser Glu Asp Thr Ala Val Tyr Tyr Cys
                85                  90                  95

Val Arg Ser Asp Phe Leu Tyr Trp Tyr Phe Asp Val Trp Gly Gln Gly
            100                 105                 110

```
Thr Thr Val Thr Val Ser Ser
        115

<210> SEQ ID NO 68
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Thr Ala Ser Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Ala Gly Thr Lys Leu Glu Ile Lys
            100                 105

<210> SEQ ID NO 69
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Thr Ala Ser Ser Ser Val Ser Ser Ser
            20                  25                  30

Tyr Leu His Trp Tyr Gln Gln Lys Pro Gly Ser Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Ala Gly Thr Lys Leu Glu Ile Lys
            100                 105

<210> SEQ ID NO 70
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 70

Asp Ile Val Met Thr Gln Ser Pro Ser Ser Leu Ser Ala Ser Val Gly
1               5                   10                  15
```

```
Asp Arg Val Thr Ile Thr Cys Thr Ala Ser Ser Val Ser Ser
            20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Gly Arg Phe Ser
 50                      55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys His Gln Tyr His Arg Ser Pro
                 85                  90                  95

Leu Thr Phe Gly Ala Gly Thr Lys Leu Glu Ile Lys
             100                 105
```

<210> SEQ ID NO 71
<211> LENGTH: 449
<212> TYPE: PRT
<213> ORGANISM: Artificial Sequence
<220> FEATURE:
<223> OTHER INFORMATION: synthetic polypeptide

<400> SEQUENCE: 71

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Arg Gln Ser Pro Gly Lys Ser Leu Glu Trp Ile
            35                  40                  45

Gly Tyr Ile Lys Pro His Asn Ala Gly Thr Thr Tyr Asn Pro Lys Phe
 50                  55                  60

Glu Gly Arg Ala Thr Leu Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Val Arg Ser Asp Phe Leu Tyr Trp Tyr Phe Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 72
<211> LENGTH: 449
<212> TYPE: PRT
<213> ORGANISM: Artificial Sequence
<220> FEATURE:
<223> OTHER INFORMATION: synthetic polypeptide

<400> SEQUENCE: 72

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Lys Pro His Asn Ala Gly Thr Thr Tyr Asn Pro Lys Phe
    50                  55                  60

Glu Gly Arg Ala Thr Leu Thr Val Asp Thr Ser Ala Ser Thr Ala Tyr
65                  70                  75                  80

Met Glu Leu Arg Ser Leu Arg Ser Glu Asp Thr Ala Val Tyr Tyr Cys
                85                  90                  95

Val Arg Ser Asp Phe Leu Tyr Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
                    180                 185                 190
        Ser Ser Leu Gly Thr Gln Thr Tyr Ile Cys Asn Val Asn His Lys Pro
                    195                 200                 205

Ser Asn Thr Lys Val Asp Lys Lys Val Glu Pro Lys Ser Cys Asp Lys
                    210                 215                 220

Thr His Thr Cys Pro Pro Cys Pro Ala Pro Glu Leu Leu Gly Gly Pro
        225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                    260                 265                 270

Pro Glu Val Lys Phe Asn Trp Tyr Val Asp Gly Val Glu Val His Asn
                    275                 280                 285

Ala Lys Thr Lys Pro Arg Glu Glu Gln Tyr Asn Ser Thr Tyr Arg Val
                    290                 295                 300

Val Ser Val Leu Thr Val Leu His Gln Asp Trp Leu Asn Gly Lys Glu
        305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                    340                 345                 350

Leu Pro Pro Ser Arg Asp Glu Leu Thr Lys Asn Gln Val Ser Leu Thr
                    355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro Gly
                    435                 440                 445

Lys
```

<210> SEQ ID NO 73
<211> LENGTH: 215
<212> TYPE: PRT
<213> ORGANISM: Artificial Sequence
<220> FEATURE:
<223> OTHER INFORMATION: synthetic polypeptide

<400> SEQUENCE: 73

```
        Asp Ile Gln Met Thr Gln Ser Pro Ser Ser Leu Ser Ala Ser Val Gly
        1               5                   10                  15

Asp Arg Val Thr Ile Thr Cys Thr Ala Ser Ser Val Ser Ser Ser
                    20                  25                  30

Tyr Leu His Trp Tyr Gln Gln Lys Pro Gly Lys Ala Pro Lys Leu Leu
                    35                  40                  45

Ile Tyr Ser Thr Ser Asn Leu Ala Ser Gly Val Pro Ser Arg Phe Ser
                    50                  55                  60

Gly Ser Gly Ser Gly Thr Asp Phe Thr Leu Thr Ile Ser Ser Leu Gln
        65                  70                  75                  80

Pro Glu Asp Phe Ala Thr Tyr Tyr Cys His Gln Tyr His Arg Ser Pro
                    85                  90                  95
```

```
Leu Thr Phe Gly Ala Gly Thr Lys Leu Glu Ile Lys Arg Thr Val Ala
                100                 105                 110

Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 74
<211> LENGTH: 215
<212> TYPE: PRT
<213> ORGANISM: Artificial Sequence
<220> FEATURE:
<223> OTHER INFORMATION: synthetic polypeptide

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Thr Ala Ser Ser Ser Val Ser Ser Ser
            20                  25                  30

Tyr Leu His Trp Tyr Gln Gln Lys Pro Gly Ser Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Ala Gly Thr Lys Leu Glu Ile Lys Arg Thr Val Ala
                100                 105                 110

Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 75
```

<211> LENGTH: 215
<212> TYPE: PRT
<213> ORGANISM: Artificial Sequence
<220> FEATURE:
<223> OTHER INFORMATION: synthetic polypeptide

<400> SEQUENCE: 75

```
Asp Ile Val Met Thr Gln Ser Pro Ser Ser Leu Ser Ala Ser Val Gly
1               5                   10                  15

Asp Arg Val Thr Ile Thr Cys Thr Ala Ser Ser Val Ser Ser Ser
            20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Gly Arg Phe Ser
        50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Ala Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 76
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 76

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Tyr Ile Asn Pro Ser Ser Gly Tyr Thr Lys Ser Asn Gln Lys Phe
        50                  55                  60

Lys Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Trp Leu Leu Ser Ala Trp Phe Ala Tyr Trp Gly Gln Gly Thr
```

Leu Val Thr Val Ser Ser
        115

<210> SEQ ID NO 77
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Arg Pro Gly Gln Gly Leu Glu Trp Met
            35                  40                  45

Gly Tyr Ile Asn Pro Ser Ser Gly Tyr Thr Lys Ser Asn Gln Lys Phe
        50                  55                  60

Lys Asp Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Trp Leu Leu Ser Ala Trp Phe Ala Tyr Trp Gly Gln Gly Thr
                100                 105                 110

Leu Val Thr Val Ser Ser
        115

<210> SEQ ID NO 78
<211> LENGTH: 118
<212> TYPE: PRT
<213> ORGANISM: Artificial Sequence
<220> FEATURE:
<223> OTHER INFORMATION: synthetic polypeptide

<400> SEQUENCE: 78

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Arg Gln Arg Pro Gly Gln Gly Leu Glu Trp Ile
            35                  40                  45

Gly Tyr Ile Asn Pro Ser Ser Gly Tyr Thr Lys Ser Asn Gln Lys Phe
        50                  55                  60

Lys Asp Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Trp Leu Leu Ser Ala Trp Phe Ala Tyr Trp Gly Gln Gly Thr
                100                 105                 110

Leu Val Thr Val Ser Ser
        115

<210> SEQ ID NO 79
<211> LENGTH: 107
<212> TYPE: PRT
<213> ORGANISM: Artificial Sequence
<220> FEATURE:

<223> OTHER INFORMATION: synthetic polypeptide

<400> SEQUENCE: 79

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Ile Asn Thr Tyr
            20                  25                  30
Leu Ser Trp Phe Gln Gln Lys Pro Gly Lys Ala Pro Lys Ser Leu Ile
        35                  40                  45
Tyr Arg Ser Asn Ile Leu Val Asp Gly Val Pro Ser Arg Phe Ser Gly
    50                  55                  60
Ser Gly Ser Gly Gln Asp Phe Thr Leu Thr Ile Ser Ser Leu Gln Pro
65                  70                  75                  80
Glu Asp Phe Ala Ile Tyr Tyr Cys Leu Gln Tyr Asp Asp Phe Pro Tyr
                85                  90                  95
Thr Phe Gly Gln Gly Thr Lys Leu Glu Ile Lys
            100                 105
```

<210> SEQ ID NO 80
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 80

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Ile Asn Thr Tyr
            20                  25                  30
Leu Ser Trp Phe Gln Gln Lys Pro Gly Lys Ser Pro Lys Ser Leu Ile
        35                  40                  45
Tyr Arg Ser Asn Ile Leu Val Asp Gly Val Pro Ser Arg Phe Ser Gly
    50                  55                  60
Ser Gly Ser Gly Gln Asp Tyr Thr Leu Thr Ile Ser Ser Leu Gln Pro
65                  70                  75                  80
Glu Asp Phe Ala Ile Tyr Tyr Cys Leu Gln Tyr Asp Asp Phe Pro Tyr
                85                  90                  95
Thr Phe Gly Gln Gly Thr Lys Leu Glu Ile Lys
            100                 105
```

<210> SEQ ID NO 81
<211> LENGTH: 448
<212> TYPE: PRT
<213> ORGANISM: Artificial Sequence
<220> FEATURE:
<223> OTHER INFORMATION: synthetic polypeptide

<400> SEQUENCE: 81

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Trp Met His Trp Val Arg Gln Ala Pro Gly Gln Gly Leu Glu Trp Met
        35                  40                  45
Gly Tyr Ile Asn Pro Ser Ser Gly Tyr Thr Lys Ser Asn Gln Lys Phe
    50                  55                  60
Lys Asp Arg Val Thr Met Thr Ala Asp Thr Ser Thr Ser Thr Ala Tyr
```

```
            65                  70                  75                  80
Met Glu Leu Ser Ser Leu Arg Ser Glu Asp Thr Ala Val Tyr Tyr Cys
                85                  90                  95

Gly Arg Trp Leu Leu Ser Ala Trp Phe Ala Tyr Trp Gly Gln Gly Thr
               100                 105                 110

Leu Val Thr Val Ser Ser Ala Ser Thr Lys Gly Pro Ser Val Phe Pro
               115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
               165                 170                 175

Ser Ser Gly Leu Tyr Ser Leu Ser Val Val Thr Val Pro Ser Ser
               180                 185                 190

Ser Leu Gly Thr Gln Thr Tyr Ile Cys Asn Val Asn His Lys Pro Ser
               195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
               245                 250                 255

Thr Pro Glu Val Thr Cys Val Val Val Asp Val Ser His Glu Asp Pro
               260                 265                 270

Glu Val Lys Phe Asn Trp Tyr Val Asp Gly Val Glu Val His Asn Ala
               275                 280                 285

Lys Thr Lys Pro Arg Glu Glu Gln Tyr Asn Ser Thr Tyr Arg Val Val
               290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
               325                 330                 335

Ile Ser Lys Ala Lys Gly Gln Pro Arg Glu Pro Gln Val Tyr Thr Leu
               340                 345                 350

Pro Pro Ser Arg Asp Glu Leu Thr Lys Asn Gln Val Ser Leu Thr Cys
               355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
               405                 410                 415

Arg Trp Gln Gln Gly Asn Val Phe Ser Cys Ser Val Met His Glu Ala
               420                 425                 430

Leu His Asn His Tyr Thr Gln Lys Ser Leu Ser Leu Ser Pro Gly Lys
               435                 440                 445

<210> SEQ ID NO 82
<211> LENGTH: 448
<212> TYPE: PRT
<213> ORGANISM: Artificial Sequence
<220> FEATURE:
<223> OTHER INFORMATION: synthetic polypeptide
```

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Arg Pro Gly Gln Gly Leu Glu Trp Met
        35                  40                  45

Gly Tyr Ile Asn Pro Ser Ser Gly Tyr Thr Lys Ser Asn Gln Lys Phe
    50                  55                  60

Lys Asp Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Trp Leu Leu Ser Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

-continued

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 83
<211> LENGTH: 448
<212> TYPE: PRT
<213> ORGANISM: Artificial Sequence
<220> FEATURE:
<223> OTHER INFORMATION: synthetic polypeptide

<400> SEQUENCE: 83

Gln Val Gln Leu Gln Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Arg Pro Gly Gln Gly Leu Glu Trp Ile
        35                  40                  45

Gly Tyr Ile Asn Pro Ser Ser Gly Tyr Thr Lys Ser Asn Gln Lys Phe
    50                  55                  60

Lys Asp Arg Ala Thr Leu Thr Ala Asp Thr Ser Ser Thr Thr Ala Tyr
65                  70                  75                  80

Met Glu Leu Ser Ser Leu Arg Ser Glu Asp Thr Ala Val Tyr Tyr Cys
                85                  90                  95

Gly Arg Trp Leu Leu Ser Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 84
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Thr Tyr
            20                  25                  30

Leu Ser Trp Phe Gln Gln Lys Pro Gly Lys Ala Pro Lys Ser Leu Ile
        35                  40                  45

Tyr Arg Ser Asn Ile Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Ile Tyr Tyr Cys Leu Gln Tyr Asp Asp Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 85
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Thr Tyr
            20                  25                  30

Leu Ser Trp Phe Gln Gln Lys Pro Gly Lys Ser Pro Lys Ser Leu Ile
        35                  40                  45

Tyr Arg Ser Asn Ile Leu Val Asp Gly Val Pro Ser Arg Phe Ser Gly
50                  55                  60

Ser Gly Ser Gly Gln Asp Tyr Thr Leu Thr Ile Ser Ser Leu Gln Pro
65                  70                  75                  80

Glu Asp Phe Ala Ile Tyr Tyr Cys Leu Gln Tyr Asp Asp Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 86
<211> LENGTH: 442
<212> TYPE: PRT
<213> ORGANISM: Artificial Sequence
<220> FEATURE:
<223> OTHER INFORMATION: synthetic polypeptide

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Tyr Ile Asn Pro Ser Gly Tyr Thr Lys Ser Asn Gln Lys Phe
50                  55                  60

Lys Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Trp Leu Leu Ser Ala Trp Phe Ala Tyr Trp Gly Gln Gly Thr
            100                 105                 110

Leu Val Thr Val Ser Ser Ala Lys Thr Thr Pro Pro Ser Val Tyr Pro

```
            115                 120                 125
Leu Ala Pro Gly Ser Ala Ala Gln Thr Asn Ser Met Val Thr Leu Gly
        130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Val Thr Val Pro Ser Ser Thr
        180                 185                 190

Trp Pro Ser Glu Thr Val Thr Cys Asn Val Ala His Pro Ala Ser Ser
                195                 200                 205

Thr Lys Val Asp Lys Lys Ile Val Pro Arg Asp Cys Gly Cys Lys Pro
        210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
        260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Lys Glu Gln
        340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
                420                 425                 430

Glu Lys Ser Leu Ser His Ser Pro Gly Lys
        435                 440

<210> SEQ ID NO 87
<211> LENGTH: 442
<212> TYPE: PRT
<213> ORGANISM: Artificial Sequence
<220> FEATURE:
<223> OTHER INFORMATION: synthetic polypeptide

<400> SEQUENCE: 87

Gln Val Gln Leu Gln Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Arg Gln Arg Pro Gly Gln Gly Leu Glu Trp Ile
```

35                  40                  45
Gly Tyr Ile Asn Pro Ser Ser Gly Tyr Thr Lys Ser Asn Gln Lys Phe
 50                  55                  60

Lys Asp Arg Ala Thr Leu Thr Ala Asp Thr Ser Ser Thr Ala Tyr
 65                  70                  75                  80

Met Glu Leu Ser Ser Leu Arg Ser Glu Asp Thr Ala Val Tyr Tyr Cys
                 85                  90                  95

Gly Arg Trp Leu Leu Ser Ala Trp Phe Ala Tyr Trp Gly Gln Gly Thr
                100                 105                 110

Leu Val Thr Val Ser Ser Ala Lys Thr Thr Pro Pro Ser Val Tyr Pro
                115                 120                 125

Leu Ala Pro Gly Ser Ala Ala Gln Thr Asn Ser Met Val Thr Leu Gly
                130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
                180                 185                 190

Trp Pro Ser Glu Thr Val Thr Cys Asn Val Ala His Pro Ala Ser Ser
                195                 200                 205

Thr Lys Val Asp Lys Lys Ile Val Pro Arg Asp Cys Gly Cys Lys Pro
                210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
                260                 265                 270

Phe Val Asp Asp Val Glu Val His Thr Ala Gln Thr Gln Pro Arg Glu
                275                 280                 285

Glu Gln Phe Asn Ser Thr Phe Arg Ser Val Ser Glu Leu Pro Ile Met
                290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
                340                 345                 350

Met Ala Lys Asp Lys Val Ser Leu Thr Cys Met Ile Thr Asp Phe Phe
                355                 360                 365

Pro Glu Asp Ile Thr Val Glu Trp Gln Trp Asn Gly Gln Pro Ala Glu
                370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
                420                 425                 430

Glu Lys Ser Leu Ser His Ser Pro Gly Lys
                435                 440

<210> SEQ ID NO 88

```
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Thr Tyr
            20                  25                  30

Leu Ser Trp Phe Gln Gln Lys Pro Gly Lys Ala Pro Lys Ser Leu Ile
        35                  40                  45

Tyr Arg Ser Asn Ile Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Ile Tyr Tyr Cys Leu Gln Tyr Asp Asp Phe Pro Tyr
                85                  90                  95

Thr Phe Gly Gln Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 89
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Thr Tyr
            20                  25                  30

Leu Ser Trp Phe Gln Gln Lys Pro Gly Lys Ser Pro Lys Ser Leu Ile
        35                  40                  45

Tyr Arg Ser Asn Ile Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Ile Tyr Tyr Cys Leu Gln Tyr Asp Asp Phe Pro Tyr
                85                  90                  95

Thr Phe Gly Gln Gly Thr Lys Leu Glu Ile Lys Arg Ala Asp Ala Ala
```

```
                100                 105                 110
Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 90
<211> LENGTH: 448
<212> TYPE: PRT
<213> ORGANISM: Artificial Sequence
<220> FEATURE:
<223> OTHER INFORMATION: synthetic polypeptide

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Tyr Ile Asn Pro Ser Ser Gly Tyr Thr Lys Ser Asn Gln Lys Phe
    50                  55                  60

Lys Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Trp Leu Leu Ser Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
```

```
                    245                 250                 255
Thr Pro Glu Val Thr Cys Val Val Asp Val Ser His Glu Asp Pro
                260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 91
<211> LENGTH: 448
<212> TYPE: PRT
<213> ORGANISM: Artificial Sequence
<220> FEATURE:
<223> OTHER INFORMATION: synthetic polypeptide

<400> SEQUENCE: 91

Gln Val Gln Leu Gln Gln Ser Gly Ala Glu Val Lys Lys Pro Gly Ala
1               5                   10                  15
Ser Val Lys Leu Ser Cys Lys Ala Ser Gly Tyr Thr Phe Thr Ser Tyr
            20                  25                  30
Trp Met His Trp Val Arg Gln Arg Pro Gly Gln Gly Leu Glu Trp Ile
        35                  40                  45
Gly Tyr Ile Asn Pro Ser Ser Gly Tyr Thr Lys Ser Asn Gln Lys Phe
    50                  55                  60
Lys Asp Arg Ala Thr Leu Thr Ala Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Gly Arg Trp Leu Leu Ser Ala Trp Phe Ala Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
```

```
                165                 170                 175
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220

His Thr Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 92
<211> LENGTH: 357
<212> TYPE: DNA
<213> ORGANISM: Artificial Sequence
<220> FEATURE:
<223> OTHER INFORMATION: synthetic polynucleotide

<400> SEQUENCE: 92
caggtgcagc tggtgcagag cggcgccgag gtgaagaagc ccggcgccag cgtgaagatg     60
agctgcaagg ccagcggcta caccttcacc gactacaaca tgcactgggt gagacagagc    120
cccggcaaga gcctggagtg gatcggctac atcaagcccc acaacgccgg caccacctac    180
aaccccaagt tcgagggcag agccacccctg accgtggaca ccagcgccag caccgcctac    240
atggagctga gcagcctgag aagcgaggac accgccgtgt actactgcgt aagagcgac    300 ttcctgtact ggtacttcga cgtgtgggc cagggcacca ccgtgaccgt gtcctca       357

<210> SEQ ID NO 93
<211> LENGTH: 357
<212> TYPE: DNA
```

```
<213> ORGANISM: Artificial Sequence
<220> FEATURE:
<223> OTHER INFORMATION: synthetic polynucleotide

<400> SEQUENCE: 93
caggtgcagc tggtgcagag cggcgccgag gtgaagaagc ccggcgccag cgtgaagatg      60
agctgcaagg ccagcggcta caccttcacc gactacaaca tgcactgggt gaagcagagc     120
cacggcaaga gcctggagtg gatcggctac atcaagcccc acaacgccgg caccacctac     180
aaccccaagt tcgagggcag agccaccctg accgtggaca ccagcgccag caccgcctac     240
atggagctga aagcctgag aagcgaggac accgccgtgt actactgcgt aagaagcgat     300
tttctctact ggtatttcga tgtctggggc cagggcacca ccgtgaccgt gtcctca       357

<210> SEQ ID NO 94
<211> LENGTH: 324
<212> TYPE: DNA
<213> ORGANISM: Artificial Sequence
<220> FEATURE:
<223> OTHER INFORMATION: synthetic polynucleotide

<400> SEQUENCE: 94
gacatccaga tgacccagag ccccagcagc ctgagcgcca gcgtgggcga cagagtgacc      60
atcacctgca ccgccagcag cagcgtgagc agcagctacc tgcactggta ccagcagaag     120
cccggcaagg cccccaagct gctgatctac agcaccagca acctggccag cggcgtgccc     180
agcagattca gcggcagcgg cagcggcacc gacttcaccc tgaccatcag cagcctgcag     240
cccgaggact tcgccaccta ctactgccac cagtatcatc gttccccgct cacgttcggc     300
gccggcacca agctggagat caag                                            324

<210> SEQ ID NO 95
<211> LENGTH: 324
<212> TYPE: DNA
<213> ORGANISM: Artificial Sequence
<220> FEATURE:
<223> OTHER INFORMATION: synthetic polynucleotide

<400> SEQUENCE: 95
gacatccaga tgacccagag ccccagcagc ctgagcgcca gcgtgggcga cagagtgacc      60
atcacctgca ccgccagcag cagcgtgagc agcagctacc tgcactggta ccagcagaag     120
cccggcagcg cccccaagct gtggatctac agcaccagca acctggccag cggcgtgccc     180
agcagattca gcggcagcgg cagcggcacc gactacaccc tgaccatcag cagcctgcag     240
cccgaggact tcgccaccta ctactgccac cagtatcatc gttccccgct cacgttcggc     300
gccggcacca agctggagat caag                                            324

<210> SEQ ID NO 96
<211> LENGTH: 324
<212> TYPE: DNA
<213> ORGANISM: Artificial Sequence
<220> FEATURE:
<223> OTHER INFORMATION: synthetic polynucleotide

<400> SEQUENCE: 96
gacatcgtga tgacccagag ccccagcagc ctgagcgcca gcgtgggcga cagagtgacc      60
atcacctgca ccgccagcag cagcgtgagc agcagctacc tgcactggta ccagcagaag     120
cccggcagca gccccaagct gtggatctac agcaccagca acctggccag cggcgtgccc     180
ggcagattca gcggcagcgg cagcggcacc gactacaccc tgaccatcag cagcctgcag     240
```

```
cccgaggact tcgccaccta ctactgccac cagtatcatc gttccccgct cacgttcggc    300
gccggcacca agctggagat caag                                          324

<210> SEQ ID NO 97
<211> LENGTH: 1347
<212> TYPE: DNA
<213> ORGANISM: Artificial Sequence
<220> FEATURE:
<223> OTHER INFORMATION: synthetic polynucleotide

<400> SEQUENCE: 97
caggtgcagc tggtgcagag cggcgccgag gtgaagaagc ccggcgccag cgtgaagatg     60
agctgcaagg ccagcggcta caccttcacc gactacaaca tgcactgggt gagacagagc    120
cccggcaaga gcctggagtg gatcggctac atcaagcccc acaacgccgg caccacctac    180
aaccccaagt tcgagggcag agccaccctg accgtggaca ccagcgccag caccgcctac    240
atggagctga gcagcctgag aagcgaggac accgccgtgt actactgcgt aagaagcgac    300
ttcctgtact ggtacttcga cgtgtggggc cagggcacca ccgtgaccgt gtcctcagct    360
agcaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggatgagttg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                      1347

<210> SEQ ID NO 98
<211> LENGTH: 1347
<212> TYPE: DNA
<213> ORGANISM: Artificial Sequence
<220> FEATURE:
<223> OTHER INFORMATION: synthetic polynucleotide

<400> SEQUENCE: 98
caggtgcagc tggtgcagag cggcgccgag gtgaagaagc ccggcgccag cgtgaagatg     60
agctgcaagg ccagcggcta caccttcacc gactacaaca tgcactgggt gaagcagagc    120
cacggcaaga gcctggagtg gatcggctac atcaagcccc acaacgccgg caccacctac    180
aaccccaagt tcgagggcag agccaccctg accgtggaca ccagcgccag caccgcctac    240
```

| | |
|---|---|
| atggagctga gaagcctgag aagcgaggac accgccgtgt actactgcgt aagaagcgat | 300 |
| tttctctact ggtatttcga tgtctggggc cagggcacca ccgtgaccgt gtcctcagct | 360 |
| agcaccaagg gcccatcggt cttccccctg gcaccctcct ccaagagcac ctctgggggc | 420 |
| acagcggccc tgggctgcct ggtcaaggac tacttccccg aaccggtgac ggtgtcgtgg | 480 |
| aactcaggcg ccctgaccag cggcgtgcac accttcccgg ctgtcctaca gtcctcagga | 540 |
| ctctactccc tcagcagcgt ggtgaccgtg ccctccagca gcttgggcac ccagacctac | 600 |
| atctgcaacg tgaatcacaa gcccagcaac accaaggtgg acaagaaagt tgagcccaaa | 660 |
| tcttgtgaca aaactcacac atgcccaccg tgcccagcac ctgaactcct ggggggaccg | 720 |
| tcagtcttcc tcttcccccc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacaacagc | 900 |
| acgtaccgtg tggtcagcgt cctcaccgtc ctgcaccagg actggctgaa tggcaaggag | 960 |
| tacaagtgca aggtctccaa caaagccctc ccagccccca tcgagaaaac catctccaaa | 1020 |
| gccaaagggc agccccgaga accacaggtg tacaccctgc ccccatcccg ggatgagttg | 1080 |
| accaagaacc aggtcagcct gacctgcctg gtcaaaggct tctatcccag cgacatcgcc | 1140 |
| gtggagtggg agagcaatgg gcagccggag aacaactaca agaccacgcc tcccgtgctg | 1200 |
| gactccgacg gctccttctt cctctacagc aagctcaccg tggacaagag caggtggcag | 1260 |
| caggggaacg tcttctcatg ctccgtgatg catgaggctc tgcacaacca ctacacgcag | 1320 |
| aagagcctct ccctgtctcc gggtaaa | 1347 |

<210> SEQ ID NO 99
<211> LENGTH: 645
<212> TYPE: DNA
<213> ORGANISM: Artificial Sequence
<220> FEATURE:
<223> OTHER INFORMATION: synthetic polynucleotide

<400> SEQUENCE: 99

| | |
|---|---|
| gacatccaga tgacccagag ccccagcagc ctgagcgcca gcgtgggcga cagagtgacc | 60 |
| atcacctgca ccgccagcag cagcgtgagc agcagctacc tgcactggta ccagcagaag | 120 |
| cccggcaagg cccccaagct gctgatctac agcaccagca acctggccag cggcgtgccc | 180 |
| agcagattca gcggcagcgg cagcggcacc gacttcaccc tgaccatcag cagcctgcag | 240 |
| cccgaggact cgccaccta ctactgccac cagtatcatc gttccccgct cacgttcggc | 300 |
| gccggcacca agctggagat caagcgtacg gtggctgcac catctgtctt catcttcccg | 360 |
| ccatctgatg agcagttgaa atctggaact gcctctgttg tgtgcctgct gaataacttc | 420 |
| tatcccagag aggccaaagt acagtggaag gtggataacg ccctccaatc gggtaactcc | 480 |
| caggagagtg tcacagagca ggacagcaag gacagcacct acagcctcag cagcaccctg | 540 |
| acgctgagca aagcagacta cgagaaacac aaagtctacg cctgcgaagt cacccatcag | 600 |
| ggcctgagct cgcccgtcac aaagagcttc aacaggggag agtgt | 645 |

<210> SEQ ID NO 100
<211> LENGTH: 645
<212> TYPE: DNA
<213> ORGANISM: Artificial Sequence
<220> FEATURE:
<223> OTHER INFORMATION: synthetic polynucleotide

<400> SEQUENCE: 100

-continued

```
gacatccaga tgacccagag ccccagcagc ctgagcgcca gcgtgggcga cagagtgacc        60
atcacctgca ccgccagcag cagcgtgagc agcagctacc tgcactggta ccagcagaag       120
cccggcagcg cccccaagct gtggatctac agcaccagca acctggccag cggcgtgccc       180
agcagattca gcggcagcgg cagcggcacc gactacaccc tgaccatcag cagcctgcag       240
cccgaggact cgccaccta ctactgccac cagtatcatc gttccccgct cacgttcggc        300
gccggcacca agctggagat caagcgtacg gtggctgcac catctgtctt catcttcccg       360
ccatctgatg agcagttgaa atctggaact gcctctgttg tgtgcctgct gaataacttc       420
tatcccagag aggccaaagt acagtggaag gtggataacg ccctccaatc gggtaactcc       480
caggagagtg tcacagagca ggacagcaag gacagcacct acagcctcag cagcaccctg       540
acgctgagca agcagactac cgagaaacac aaagtctacg cctgcgaagt cacccatcag       600
ggcctgagct cgcccgtcac aaagagcttc aacaggggag agtgt                       645
```

`<210>` SEQ ID NO 101
`<211>` LENGTH: 645
`<212>` TYPE: DNA
`<213>` ORGANISM: Artificial Sequence
`<220>` FEATURE:
`<223>` OTHER INFORMATION: synthetic polynucleotide

`<400>` SEQUENCE: 101

```
gacatcgtga tgacccagag ccccagcagc ctgagcgcca gcgtgggcga cagagtgacc        60
atcacctgca ccgccagcag cagcgtgagc agcagctacc tgcactggta ccagcagaag       120
cccggcagca gccccaagct gtggatctac agcaccagca acctggccag cggcgtgccc       180
ggcagattca gcggcagcgg cagcggcacc gactacaccc tgaccatcag cagcctgcag       240
cccgaggact cgccaccta ctactgccac cagtatcatc gttccccgct cacgttcggc        300
gccggcacca agctggagat caagcgtacg gtggctgcac catctgtctt catcttcccg       360
ccatctgatg agcagttgaa atctggaact gcctctgttg tgtgcctgct gaataacttc       420
tatcccagag aggccaaagt acagtggaag gtggataacg ccctccaatc gggtaactcc       480
caggagagtg tcacagagca ggacagcaag gacagcacct acagcctcag cagcaccctg       540
acgctgagca agcagactac cgagaaacac aaagtctacg cctgcgaagt cacccatcag       600
ggcctgagct cgcccgtcac aaagagcttc aacaggggag agtgt                       645
```

`<210>` SEQ ID NO 102
`<211>` LENGTH: 354
`<212>` TYPE: DNA
`<213>` ORGANISM: Artificial Sequence
`<220>` FEATURE:
`<223>` OTHER INFORMATION: synthetic polynucleotide

`<400>` SEQUENCE: 102

```
caggtgcagc tggtgcagag cggcgccgag gtgaagaagc ccggcgccag cgtgaaggtg        60
agctgcaagg ccagcggcta caccttcacc agctactgga tgcactgggt gagacaggcc       120
cccggccagg gcctggagtg gatgggctac atcaacccca gcagcggcta caccaagagc       180
aaccagaagt tcaaggacag agtgaccatg accgccgaca ccagcaccag caccgcctac       240
atggagctga gcagcctgag aagcgaggac accgccgtgt actactgcgg aagatggtta       300
ctttcggcct ggtttgctta ctggggccag ggcaccctgg tgaccgtgag cagc             354
```

`<210>` SEQ ID NO 103

```
<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 103
caggtgcagc tggtgcagag cggcgccgag gtgaagaagc ccggcgccag cgtgaaggtg      60
agctgcaagg ccagcggcta caccttcacc agctactgga tgcactgggt gagacagaga     120
cccggccagg gcctggagtg gatgggctac atcaacccca gcagcggcta caccaagagc     180
aaccagaagt tcaaggacag agtgaccctg accgccgaca ccagcaccag caccgcctac     240
atggagctga gcagcctgag aagcgaggac accgccgtgt actactgcgg cagatggctg     300
ctgagcgcct ggttcgccta ctggggccag ggcaccctgg tgaccgtgag cagc            354

<210> SEQ ID NO 104
<211> LENGTH: 354
<212> TYPE: DNA
<213> ORGANISM: Artificial Sequence
<220> FEATURE:
<223> OTHER INFORMATION: synthetic polynucleotide

<400> SEQUENCE: 104
caggtgcagc tgcagcagag cggcgccgag gtgaagaagc ccggcgccag cgtgaagctg      60
agctgcaagg ccagcggcta caccttcacc agctactgga tgcactgggt gagacagaga     120
cccggccagg gcctggagtg gatcggctac atcaacccca gcagcggcta caccaagagc     180
aaccagaagt tcaaggacag agccaccctg accgccgaca ccagcaccag caccgcctac     240
atggagctga gcagcctgag aagcgaggac accgccgtgt actactgcgg cagatggctg     300
ctgagcgcct ggttcgccta ctggggccag ggcaccctgg tgaccgtgag cagc            354

<210> SEQ ID NO 105
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 105
gacatccaga tgacccagag ccccagcagc ctgagcgcca gcgtgggcga cagagtgacc      60
atcacctgca aggccagcca ggacatcaac acctacctga gctggttcca gcagaagccc     120
ggcaaggccc ccaagagcct gatctacaga agcaacatcc tggtggacgg cgtgcccagc     180
agattcagcg gcagcggcag cggccaggac ttcaccctga ccatcagcag cctgcagccc     240
gaggacttcg ccatctacta ctgcctacag tatgatgact ttccgtacac gttcggccag     300
ggcaccaagc tggagatcaa g                                                 321

<210> SEQ ID NO 106
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 106
gacatccaga tgacccagag ccccagcagc ctgagcgcca gcgtgggcga cagagtgacc      60
atcacctgca aggccagcca ggacatcaac acctacctga gctggttcca gcagaagccc     120
ggcaagagcc ccaagagcct gatctacaga agcaacatcc tggtggacgg cgtgcccagc     180
```

| | |
|---|---|
| agattcagcg gcagcggcag cggccaggac tacaccctga ccatcagcag cctgcagccc | 240 |
| gaggacttcg ccatctacta ctgcctacag tatgatgact ttccgtacac gttcggccag | 300 |
| ggcaccaagc tggagatcaa g | 321 |

<210> SEQ ID NO 107
<211> LENGTH: 1344
<212> TYPE: DNA
<213> ORGANISM: Artificial Sequence
<220> FEATURE:
<223> OTHER INFORMATION: synthetic polynucleotide

<400> SEQUENCE: 107

| | |
|---|---|
| caggtgcagc tggtgcagag cggcgccgag gtgaagaagc ccggcgccag cgtgaaggtg | 60 |
| agctgcaagg ccagcggcta caccttcacc agctactgga tgcactgggt gagacaggcc | 120 |
| cccggccagg gcctggagtg gatgggctac atcaaccca gcagcggcta caccaagagc | 180 |
| aaccagaagt tcaaggacag agtgaccatg accgccgaca ccagcaccag caccgcctac | 240 |
| atggagctga gcagcctgag aagcgaggac accgccgtgt actactgcgg aagatggtta | 300 |
| ctttcggcct ggtttgctta ctggggccag ggcaccctgg tgaccgtgag cagcgctagc | 360 |
| accaagggcc catcggtctt ccccctggca ccctcctcca agagcacctc tgggggcaca | 420 |
| gcggccctgg gctgcctggt caaggactac ttccccgaac cggtgacggt gtcgtggaac | 480 |
| tcaggcgccc tgaccagcgg cgtgcacacc ttcccggctg tcctacagtc ctcaggactc | 540 |
| tactccctca gcagcgtggt gaccgtgccc tccagcagct gggcaccca gacctacatc | 600 |
| tgcaacgtga atcacaagcc cagcaacacc aaggtggaca agaaagttga gcccaaatct | 660 |
| tgtgacaaaa ctcacacatg cccaccgtgc ccagcacctg aactcctggg gggaccgtca | 720 |
| gtcttcctct tccccccaaa acccaaggac accctcatga tctcccggac ccctgaggtc | 780 |
| acatgcgtgg tggtggacgt gagccacgaa gaccctgagg tcaagttcaa ctggtacgtg | 840 |
| gacggcgtgg aggtgcataa tgccaagaca aagccgcggg aggagcagta caacagcacg | 900 |
| taccgtgtgg tcagcgtcct caccgtcctg caccaggact ggctgaatgg caaggagtac | 960 |
| aagtgcaagg tctccaacaa agccctccca gcccccatcg agaaaaccat ctccaaagcc | 1020 |
| aaagggcagc cccgagaacc acaggtgtac accctgcccc catcccggga tgagttgacc | 1080 |
| aagaaccagg tcagcctgac ctgcctggtc aaaggcttct atcccagcga catcgccgtg | 1140 |
| gagtgggaga gcaatgggca gccggagaac aactacaaga ccacgcctcc cgtgctggac | 1200 |
| tccgacggct ccttcttcct ctacagcaag ctcaccgtgg acaagagcag gtggcagcag | 1260 |
| gggaacgtct tctcatgctc cgtgatgcat gaggctctgc acaaccacta cacgcagaag | 1320 |
| agcctctccc tgtctccggg taaa | 1344 |

<210> SEQ ID NO 108
<211> LENGTH: 1344
<212> TYPE: DNA
<213> ORGANISM: Artificial Sequence
<220> FEATURE:
<223> OTHER INFORMATION: synthetic polynucleotide

<400> SEQUENCE: 108

| | |
|---|---|
| caggtgcagc tggtgcagag cggcgccgag gtgaagaagc ccggcgccag cgtgaaggtg | 60 |
| agctgcaagg ccagcggcta caccttcacc agctactgga tgcactgggt gagacagaga | 120 |
| cccggccagg gcctggagtg gatgggctac atcaaccca gcagcggcta caccaagagc | 180 |

```
aaccagaagt tcaaggacag agtgaccctg accgccgaca ccagcaccag caccgcctac    240
atggagctga gcagcctgag aagcgaggac accgccgtgt actactgcgg cagatggctg    300
ctgagcgcct ggttcgccta ctggggccag ggcaccctgg tgaccgtgag cagcgctagc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttccggctg tcctacagtc ctcaggactc    540
tactccctca gcagcgtggt gaccgtgccc tccagcagct gggcaccca gacctacatc    600 tgcaacgtga atcacaagcc cagcaacacc aaggtggaca gaaagttga gcccaaatct    660 tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga tgagttgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344
```

<210> SEQ ID NO 109
<211> LENGTH: 1344
<212> TYPE: DNA
<213> ORGANISM: Artificial Sequence
<220> FEATURE:
<223> OTHER INFORMATION: synthetic polynucleotide

<400> SEQUENCE: 109

```
caggtgcagc tgcagcagag cggcgccgag gtgaagaagc ccggcgccag cgtgaagctg     60
agctgcaagg ccagcggcta caccttcacc agctactgga tgcactgggt gagacagaga    120
cccggccagg gcctggagtg gatcggctac atcaaccca gcagcggcta caccaagagc    180
aaccagaagt tcaaggacag agccaccctg accgccgaca ccagcaccag caccgcctac    240
atggagctga gcagcctgag aagcgaggac accgccgtgt actactgcgg cagatggctg    300
ctgagcgcct ggttcgccta ctggggccag ggcaccctgg tgaccgtgag cagcgctagc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttccggctg tcctacagtc ctcaggactc    540
tactccctca gcagcgtggt gaccgtgccc tccagcagct gggcaccca gacctacatc    600 tgcaacgtga atcacaagcc cagcaacacc aaggtggaca gaaagttga gcccaaatct    660 tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
```

```
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga tgagttgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344
```

<210> SEQ ID NO 110
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 110

```
gacatccaga tgacccagag cccccagcagc ctgagcgcca gcgtgggcga cagagtgacc     60
atcacctgca aggccagcca ggacatcaac acctacctga gctggttcca gcagaagccc    120
ggcaaggccc ccaagagcct gatctacaga agcaacatcc tggtggacgg cgtgcccagc    180
agattcagcg gcagcggcag cggccaggac ttcaccctga ccatcagcag cctgcagccc    240
gaggacttcg ccatctacta ctgcctacag tatgatgact ttccgtacac gttcggccag    300
ggcaccaagc tggagatcaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 111
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 111

```
gacatccaga tgacccagag cccccagcagc ctgagcgcca gcgtgggcga cagagtgacc     60
atcacctgca aggccagcca ggacatcaac acctacctga gctggttcca gcagaagccc    120
ggcaagagcc ccaagagcct gatctacaga agcaacatcc tggtggacgg cgtgcccagc    180
agattcagcg gcagcggcag cggccaggac tacaccctga ccatcagcag cctgcagccc    240
gaggacttcg ccatctacta ctgcctacag tatgatgact ttccgtacac gttcggccag    300
ggcaccaagc tggagatcaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
```

```
ctgagctcgc ccgtcacaaa gagcttcaac aggggagagt gt                          642
```

<210> SEQ ID NO 112
<211> LENGTH: 1326
<212> TYPE: DNA
<213> ORGANISM: Artificial Sequence
<220> FEATURE:
<223> OTHER INFORMATION: synthetic polynucleotide

<400> SEQUENCE: 112

```
caggtgcagc tggtgcagag cggcgccgag gtgaagaagc ccggcgccag cgtgaaggtg         60
agctgcaagg ccagcggcta caccttcacc agctactgga tgcactgggt gagacaggcc        120
cccggccagg gcctggagtg gatgggctac atcaacccca gcagcggcta caccaagagc        180
aaccagaagt tcaaggacag agtgaccatg accgccgaca ccagcaccag caccgcctac        240
atggagctga gcagcctgag aagcgaggac accgccgtgt actactgcgg aagatggtta        300
cttttcggcct ggtttgctta ctggggccag ggcaccctgg tgaccgtgag cagcgccaag        360
accacccctc cttccgtgta tcctctggct ccaggatccg ccgctcagac aaaactccatg       420
gtgaccctgg gttgcctggt gaagggctac ttccctgagc cagtgaccgt gacttggaac        480
tccggctctc tgtcttccgg agtgcacaca tttccagccg tgctgcagag cgacctgtac        540
acactgtcct cctccgtgac cgtgccttct tccacttggc cttccgagac cgtgacttgc        600
aacgtggccc acccagcctc ttctaccaag gtggacaaga gatcgtcccc ccgggattgc        660
ggttgcaagc cttgcatttg caccgtgccc gaggtgtcct ccgtgttcat cttccctccc        720
aagcctaagg acgtgctgac catcaccctg accccaaag tgacttgcgt ggtggtggac         780
atctctaagg acgaccccga ggtgcagttc tcttggttcg tggacgacgt ggaggtgcac        840
acagctcaga cacagccccg ggaggagcag ttcaactcca ccttccggag cgtgtccgag        900
ctgcccatca tgcaccagga ttggctgaac ggcaaggagt tcaagtgccg cgtgaacagc        960
gccgcttttc cagcccctat cgagaagacc atctccaaga ccaagggcag gcccaaggct       1020
cctcaggtgt acaccatccc tccccctaag gagcagatgg ccaaggacaa ggtgtccctg       1080
acttgcatga tcaccgactt cttccccgag gacatcacag tcgagtggca gtggaacggc       1140
cagccagccg agaactacaa gaacacccag cccatcatgg ataccgacgg ctcttacttc       1200
gtgtactcca agctgaacgt gcagaagtcc aattgggagg ccggcaacac cttcacttgc       1260
tccgtgctgc acgagggact gcataaccac cacaccgaga agtccctgtc ccactctccc       1320
ggcaag                                                                 1326
```

<210> SEQ ID NO 113
<211> LENGTH: 1326
<212> TYPE: DNA
<213> ORGANISM: Artificial Sequence
<220> FEATURE:
<223> OTHER INFORMATION: synthetic polynucleotide

<400> SEQUENCE: 113

```
caggtgcagc tgcagcagag cggcgccgag gtgaagaagc ccggcgccag cgtgaagctg         60
agctgcaagg ccagcggcta caccttcacc agctactgga tgcactgggt gagacagaga        120
cccggccagg gcctggagtg gatcggctac atcaacccca gcagcggcta caccaagagc        180
aaccagaagt tcaaggacag agccaccctg accgccgaca ccagcaccag caccgcctac        240
atggagctga gcagcctgag aagcgaggac accgccgtgt actactgcgg cagatggctg        300
ctgagcgcct ggttcgccta ctggggccag ggcaccctgg tgaccgtgag cagcgccaag        360
```

```
accacccctc cttccgtgta tcctctggct ccaggatccg ccgctcagac aaactccatg    420
gtgaccctgg gttgcctggt gaagggctac ttccctgagc cagtgaccgt gacttggaac    480
tccggctctc tgtcttccgg agtgcacaca tttccagccg tgctgcagag cgacctgtac    540
acactgtcct cctccgtgac cgtgccttct tccacttggc cttccgagac cgtgacttgc    600
aacgtggccc acccagcctc ttctaccaag gtggacaaga agatcgtccc ccgggattgc    660
ggttgcaagc cttgcatttg caccgtgccc gaggtgtcct ccgtgttcat cttccctccc    720
aagcctaagg acgtgctgac catcaccctg accccaaag tgacttgcgt ggtggtggac    780
atctctaagg acgaccccga ggtgcagttc tcttggttcg tggacgacgt ggaggtgcac    840
acagctcaga cacagccccg ggaggagcag ttcaactcca ccttccggag cgtgtccgag    900
ctgcccatca tgcaccagga ttggctgaac ggcaaggagt tcaagtgccg cgtgaacagc    960
gccgcttttc cagcccctat cgagaagacc atctccaaga ccaagggcag gcccaaggct   1020
cctcaggtgt acaccatccc tccccctaag gagcagatgg ccaaggacaa ggtgtccctg   1080
acttgcatga tcaccgactt cttccccgag gacatcacag tcgagtggca gtggaacggc   1140
cagccagccg agaactacaa gaacacccag cccatcatgg ataccgacgg ctcttacttc   1200
gtgtactcca agctgaacgt gcagaagtcc aattgggagg ccggcaacac cttcacttgc   1260
tccgtgctgc acgagggact gcataaccac cacaccgaga gtccctgtc ccactctccc   1320 ggcaag                                                              1326

<210> SEQ ID NO 114
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 114
gacatccaga tgacccagag ccccagcagc ctgagcgcca gcgtgggcga cagagtgacc     60
atcacctgca aggccagcca ggacatcaac acctacctga gctggttcca gcagaagccc    120
ggcaaggccc ccaagagcct gatctacaga agcaacatcc tggtggacgg cgtgcccagc    180
agattcagcg gcagcggcag cggccaggac ttcaccctga ccatcagcag cctgcagccc    240
gaggacttcg ccatctacta ctgcctacag tatgatgact ttccgtacac gttcggccag    300
ggcaccaagc tggagatcaa gagagccgac gccgctccta cagtgtctat cttccccct    360 tcttccgagc agctgaccct ggaggagcc tccgtcgtgt gtttcctcaa caacttctac    420
cccaaggaca tcaacgtcaa gtggaagatc gacggctccg agaggcagaa cggcgtgctg    480
aactcttgga ccgaccagga ctccaaggac tccacctact ccatgtcctc cacccctgacc   540 ctgaccaagg acgagtacga gcggcacaac tcctacactt gcgaggctac ccacaagacc    600
tctacctccc ccatcgtgaa gagcttcaac cgcaacgagt gt                        642

<210> SEQ ID NO 115
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 115
gacatccaga tgacccagag ccccagcagc ctgagcgcca gcgtgggcga cagagtgacc     60
```

| | | |
|---|---|---|
| atcacctgca aggccagcca ggacatcaac acctacctga gctggttcca gcagaagccc | 120 | |
| ggcaagagcc ccaagagcct gatctacaga agcaacatcc tggtggacgg cgtgcccagc | 180 | |
| agattcagcg gcagcggcag cggccaggac tacaccctga ccatcagcag cctgcagccc | 240 | |
| gaggacttcg ccatctacta ctgcctacag tatgatgact tccgtacac gttcggccag | 300 | |
| ggcaccaagc tggagatcaa gagagccgac gccgctccta cagtgtctat cttcccccct | 360 | |
| tcttccgagc agctgacctc tggaggagcc tccgtcgtgt gtttcctcaa caacttctac | 420 | |
| cccaaggaca tcaacgtcaa gtggaagatc gacggctccg agaggcagaa cggcgtgctg | 480 | |
| aactcttgga ccgaccagga ctccaaggac tccacctact ccatgtcctc caccctgacc | 540 | |
| ctgaccaagg acgagtacga gcggcacaac tcctacactt gcgaggctac ccacaagacc | 600 | |
| tctacctccc ccatcgtgaa gagcttcaac cgcaacgagt gt | 642 | |

<210> SEQ ID NO 116
<211> LENGTH: 1344
<212> TYPE: DNA
<213> ORGANISM: Artificial Sequence
<220> FEATURE:
<223> OTHER INFORMATION: synthetic polynucleotide

<400> SEQUENCE: 116

| | | |
|---|---|---|
| caggtgcagc tggtgcagag cggcgccgag gtgaagaagc ccggcgccag cgtgaaggtg | 60 | |
| agctgcaagg ccagcggcta caccttcacc agctactgga tgcactgggt gagacaggcc | 120 | |
| cccggccagg gcctggagtg gatgggctac atcaacccca gcagcggcta caccaagagc | 180 | |
| aaccagaagt tcaaggacag agtgaccatg accgccgaca ccagcaccag caccgcctac | 240 | |
| atggagctga gcagcctgag aagcgaggac accgccgtgt actactgcgg aagatggtta | 300 | |
| ctttcggcct ggtttgctta ctggggccag ggcaccctgg tgaccgtgag cagcgctagc | 360 | |
| acaaaaggac cttccgtgtt cctctggct ccttcttcta agtctaccag cggaggaaca | 420 | |
| gcagctctgg gttgtctggt gaaagattac ttcccagagc cagtgacagt gtcttggaat | 480 | |
| tcaggagctc tgacatcagg agtgcataca tttccagcag tgctgcagtc ttcaggtctg | 540 | |
| tattctctgt cctcagtggt gacagtgcct tcttcttctc tgggaaccca gacctacatc | 600 | |
| tgtaacgtga accacaagcc ttccaacacc aaggtggata agagagtgga gcccaagtct | 660 | |
| tgcgataaga cccatacttg ccctccttgt ccagctccag aatttgaagg aggaccatca | 720 | |
| gtgttcctgt ttcctcctaa gcctaaggac accctgatga tctcccggac cccagaagtg | 780 | |
| acttgtgtgg tggtggacgt gtctcacgaa gatcccgagg tgaagttcaa ttggtacgtg | 840 | |
| gacggagtgg aagtgcataa cgctaagaca aagcctagag aggagcagta caactccaca | 900 | |
| tacagagtgg tgtcagtgct gacagtgctg catcaggatt ggctgaacgg aaaggagtac | 960 | |
| aagtgcaagg tgtctaacaa ggctctgcca gcttctatcg agaagaccat ctccaaggct | 1020 | |
| aagggacagc ctagagaacc tcaggtgtac accctgcctc cttcccggga ggagatgaca | 1080 | |
| aagaaccagg tctctctgac ttgtctggtg aagggctttt acccttccga catcgccgtg | 1140 | |
| gaatgggaat ctaacggaca gccagagaac aactacaaga ccacacctcc agtgctggat | 1200 | |
| tccgacggct ccttcttcct gtactccaag ctgaccgtgg ataaatctcg ttggcagcag | 1260 | |
| ggaaacgtgt tctcttgtag cgtgatgcac gaagctctgc acaatcacta cacccagaag | 1320 | |
| tccctgtctc tgtctccagg aaaa | 1344 | |

<210> SEQ ID NO 117
<211> LENGTH: 1344

```
<212> TYPE: DNA
<213> ORGANISM: Artificial Sequence
<220> FEATURE:
<223> OTHER INFORMATION: synthetic polynucleotide

<400> SEQUENCE: 117
caggtgcagc tgcagcagag cggcgccgag gtgaagaagc ccggcgccag cgtgaagctg       60
agctgcaagg ccagcggcta caccttcacc agctactgga tgcactgggt gagacagaga      120
cccggccagg gcctggagtg gatcggctac atcaaccccca gcagcggcta caccaagagc     180
aaccagaagt tcaaggacag agccacccctg accgccgaca ccagcaccag caccgcctac    240
atggagctga gcagcctgag aagcgaggac accgccgtgt actactgcgg cagatggctg      300
ctgagcgcct ggttcgccta ctggggccag ggcaccctgg tgaccgtgag cagcgctagc      360
acaaaaggac cttccgtgtt tcctctggct ccttcttcta gtctaccag cggaggaaca       420
gcagctctgg gttgtctggt gaaagattac ttcccagagc cagtgacagt gtcttggaat      480
tcaggagctc tgcacatcag gagtgcataca tttccagcag tgctgcagtc ttcaggtctg    540
tattctctgt cctcagtggt gacagtgcct tcttcttctc tgggaaccca gacctacatc     600
tgtaacgtga accacaagcc ttccaacacc aaggtggata gagagtgga gcccaagtct       660
tgcgataaga cccatacttg ccctccttgt ccagctccag aatttgaagg aggaccatca     720
gtgttcctgt ttcctcctaa gcctaaggac accctgatga tctcccggac cccagaagtg      780
acttgtgtgg tggtggacgt gtctcacgaa gatcccgagg tgaagttcaa ttggtacgtg      840
gacggagtgg aagtgcataa cgctaagaca aagcctagag aggagcagta caactccaca     900
tacagagtgg tgtcagtgct gacagtgctg catcaggatt ggctgaacgg aaaggagtac      960
aagtgcaagg tgtctaacaa ggctctgcca gcttctatcg agaagaccat ctccaaggct     1020
aagggacagc ctagagaacc tcaggtgtac accctgcctc cttcccggga ggagatgaca    1080
aagaaccagg tctctctgac ttgtctggtg aagggctttt accccttccga catcgccgtg    1140
gaatgggaat ctaacggaca gccagagaac aactacaaga ccacacctcc agtgctggat     1200
tccgacggct ccttcttcct gtactccaag ctgaccgtgg ataaatctcg ttggcagcag     1260
ggaaacgtgt tctcttgtag cgtgatgcac gaagctctgc acaatcacta cacccagaag    1320
tccctgtctc tgtctccagg aaaa                                            1344

<210> SEQ ID NO 118
<211> LENGTH: 442
<212> TYPE: PRT
<213> ORGANISM: Artificial Sequence
<220> FEATURE:
<223> OTHER INFORMATION: synthetic polypeptide

<400> SEQUENCE: 118

Gln Val His Leu Gln Gln Ser Gly Ala Glu Leu Ala Lys Pro Gly Ala
1               5                   10                  15

Ser Val Asn Leu Ser Cys Lys Ala Ser Gly Tyr Ala Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Ser Gly Leu Ala Lys Tyr Asn Gln Lys Phe
    50                  55                  60

Lys Asp Lys Ala Thr Leu Thr Thr Asp Lys Ser Ser Asn Thr Ala Tyr
65                  70                  75                  80

Met Gln Leu Ser Ser Leu Thr Tyr Asp Asp Ser Ala Val Tyr Tyr Cys
```

85                  90                  95
Gly Arg Trp Leu Leu Ser Ala Trp Phe Ala Tyr Trp Gly Gln Gly Thr
                100                 105                 110

Leu Val Thr Val Ser Ala Ala Lys Thr Thr Pro Pro Ser Val Tyr Pro
            115                 120                 125

Leu Ala Pro Gly Ser Ala Ala Gln Thr Asn Ser Met Val Thr Leu Gly
        130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440

<210> SEQ ID NO 119
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 119

Asp Ile Lys Met Thr Gln Ser Pro Ser Ser Ile Tyr Ala Ser Leu Gly

```
            1               5                  10                  15
Glu Arg Val Thr Ile Thr Cys Lys Ala Ser Gln Gly Ile Asn Thr Tyr
                20                  25                  30
Leu Ser Trp Phe Gln Gln Lys Pro Gly Lys Ser Pro Lys Thr Leu Ile
                35                  40                  45
Tyr Arg Ala Asn Ile Leu Val Asp Gly Val Pro Ser Arg Phe Ser Gly
            50                  55                  60
Ser Gly Ser Gly Gln Asp Tyr Ser Leu Thr Ile Asn Ser Leu Glu Tyr
65                  70                  75                  80
Glu Asp Met Gly Ile Tyr Tyr Cys Leu Gln Tyr Asp Glu Phe Pro Tyr
                85                  90                  95
Thr Phe Gly Gly Gly Thr Lys Leu Glu Ile Lys Arg Ala Asp Ala Ala
                100                 105                 110
Pro Thr Val Ser Ile Phe Pro Pro Ser Glu Gln Leu Thr Ser Gly
                115                 120                 125
Gly Ala Ser Val Val Cys Phe Leu Asn Asn Phe Tyr Pro Lys Asp Ile
            130                 135                 140
Asn Val Lys Trp Lys Ile Asp Gly Ser Glu Arg Gln Asn Gly Val Leu
145                 150                 155                 160
Asn Ser Trp Thr Asp Gln Asp Ser Lys Asp Ser Thr Tyr Ser Met Ser
                165                 170                 175
Ser Thr Leu Thr Leu Thr Lys Asp Glu Tyr Glu Arg His Asn Ser Tyr
                180                 185                 190
Thr Cys Glu Ala Thr His Lys Thr Ser Thr Ser Pro Ile Val Lys Ser
                195                 200                 205
Phe Asn Arg Asn Glu Cys
210

<210> SEQ ID NO 120
<211> LENGTH: 442
<212> TYPE: PRT
<213> ORGANISM: Artificial Sequence
<220> FEATURE:
<223> OTHER INFORMATION: synthetic polypeptide

<400> SEQUENCE: 120

Gln Val Gln Leu Gln Gln Ser Gly Ala Glu Leu Ala Lys Pro Gly Ala
1               5                   10                  15
Ser Val Lys Leu Ser Cys Lys Ala Ser Gly Tyr Thr Phe Thr Ser Tyr
                20                  25                  30
Trp Met His Trp Val Lys Gln Arg Pro Gly Gln Gly Leu Glu Trp Ile
                35                  40                  45
Gly Tyr Ile Asn Pro Ser Ser Gly Tyr Thr Lys Ser Asn Gln Lys Phe
            50                  55                  60
Lys Asp Lys Ala Thr Leu Thr Ala Asp Lys Ser Ser Ser Thr Ala Tyr
65                  70                  75                  80
Met Gln Leu Ser Ser Leu Thr Tyr Glu Asp Ser Ala Val Tyr Tyr Cys
                85                  90                  95
Gly Arg Trp Leu Leu Ser Ala Trp Phe Ala Tyr Trp Gly Gln Gly Thr
                100                 105                 110
Leu Val Thr Val Ser Ala Ala Lys Thr Thr Pro Pro Ser Val Tyr Pro
                115                 120                 125
Leu Ala Pro Gly Ser Ala Ala Gln Thr Asn Ser Met Val Thr Leu Gly
            130                 135                 140
Cys Leu Val Lys Gly Tyr Phe Pro Glu Pro Val Thr Val Thr Trp Asn
```

```
            145                 150                 155                 160
Ser Gly Ser Leu Ser Ser Gly Val His Thr Phe Pro Ala Val Leu Gln
                165                 170                 175

Ser Asp Leu Tyr Thr Leu Ser Ser Val Thr Val Pro Ser Ser Thr
            180                 185                 190

Trp Pro Ser Glu Thr Val Thr Cys Asn Val Ala His Pro Ala Ser Ser
                195                 200                 205

Thr Lys Val Asp Lys Lys Ile Val Pro Arg Asp Cys Gly Cys Lys Pro
            210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
                260                 265                 270

Phe Val Asp Asp Val Glu Val His Thr Ala Gln Thr Gln Pro Arg Glu
            275                 280                 285

Glu Gln Phe Asn Ser Thr Phe Arg Ser Val Ser Glu Leu Pro Ile Met
        290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Lys Glu Gln
            340                 345                 350

Met Ala Lys Asp Lys Val Ser Leu Thr Cys Met Ile Thr Asp Phe Phe
                355                 360                 365

Pro Glu Asp Ile Thr Val Glu Trp Gln Trp Asn Gly Gln Pro Ala Glu
            370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
            435                 440

<210> SEQ ID NO 121
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 121

Asp Ile Arg Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Thr Tyr
            20                  25                  30

Leu Ser Trp Phe Gln Gln Lys Pro Gly Lys Ser Pro Lys Ser Leu Ile
        35                  40                  45

Tyr Arg Ser Asn Ile Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
```

```
                65                  70                  75                  80
        Glu Asp Met Gly Ile Tyr Tyr Cys Leu Gln Tyr Asp Asp Phe Pro Tyr
                            85                  90                  95

Thr Phe Gly Gly Gly Thr Lys Leu Glu Ile Lys Arg Ala Asp Ala Ala
                        100                 105                 110

Pro Thr Val Ser Ile Phe Pro Pro Ser Ser Glu Gln Leu Thr Ser Gly
                    115                 120                 125

Gly Ala Ser Val Val Cys Phe Leu Asn Asn Phe Tyr Pro Lys Asp Ile
                130                 135                 140

Asn Val Lys Trp Lys Ile Asp Gly Ser Glu Arg Gln Asn Gly Val Leu
        145                 150                 155                 160

Asn Ser Trp Thr Asp Gln Asp Ser Lys Asp Ser Thr Tyr Ser Met Ser
                        165                 170                 175

Ser Thr Leu Thr Leu Thr Lys Asp Glu Tyr Glu Arg His Asn Ser Tyr
                    180                 185                 190

Thr Cys Glu Ala Thr His Lys Thr Ser Thr Ser Pro Ile Val Lys Ser
                195                 200                 205

Phe Asn Arg Asn Glu Cys
            210

<210> SEQ ID NO 122
<211> LENGTH: 443
<212> TYPE: PRT
<213> ORGANISM: Artificial Sequence
<220> FEATURE:
<223> OTHER INFORMATION: synthetic polypeptide

<400> SEQUENCE: 122

Gln Val Gln Leu Lys Glu Ser Gly Pro Gly Leu Val Ala Pro Ser Gln
        1               5                   10                  15

Ser Leu Ser Ile Thr Cys Thr Val Ser Gly Phe Ser Leu Thr Asn Tyr
                        20                  25                  30

Gly Val His Trp Val Arg Gln Pro Pro Gly Lys Gly Leu Glu Trp Leu
                    35                  40                  45

Gly Val Ile Trp Ala Gly Gly Ser Thr Asn Tyr Asn Ser Ala Leu Met
                50                  55                  60

Ser Arg Leu Ser Ile Ser Lys Asp Asn Ser Lys Ser Gln Leu Phe Leu
        65                  70                  75                  80

Lys Met Asn Ser Leu Gln Ala Asp Asp Thr Ala Met Tyr Tyr Cys Ala
                        85                  90                  95

Arg Glu Arg Gly Ser Ser Trp Gly Thr Met Asp Tyr Trp Gly Gln Gly
                    100                 105                 110

Thr Ser Val Thr Val Ser Ser Ala Lys Thr Thr Pro Pro Ser Val Tyr
                115                 120                 125

Pro Leu Ala Pro Gly Ser Ala Ala Gln Thr Asn Ser Met Val Thr Leu
            130                 135                 140

Gly Cys Leu Val Lys Gly Tyr Phe Pro Glu Pro Val Thr Val Thr Trp
        145                 150                 155                 160

Asn Ser Gly Ser Leu Ser Ser Gly Val His Thr Phe Pro Ala Val Leu
                        165                 170                 175

Gln Ser Asp Leu Tyr Thr Leu Ser Ser Ser Val Thr Val Pro Ser Ser
                    180                 185                 190

Thr Trp Pro Ser Glu Thr Val Thr Cys Asn Val Ala His Pro Ala Ser
                195                 200                 205

Ser Thr Lys Val Asp Lys Lys Ile Val Pro Arg Asp Cys Gly Cys Lys
```

```
                    210                 215                 220
Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Pro Glu Val Gln Phe Ser
                260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
        290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
        370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr Glu Lys Ser Leu Ser His Ser Pro Gly Lys
            435                 440

<210> SEQ ID NO 123
<211> LENGTH: 213
<212> TYPE: PRT
<213> ORGANISM: Artificial Sequence
<220> FEATURE:
<223> OTHER INFORMATION: synthetic polypeptide

<400> SEQUENCE: 123

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Val Ser Tyr Met
                20                  25                  30

His Trp Tyr Gln Gln Lys Ser Gly Thr Ser Pro Lys Arg Trp Ile Tyr
            35                  40                  45

Asp Thr Ser Gln Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Tyr Thr
                85                  90                  95

Phe Gly Gly Gly Thr Lys Leu Glu Met Arg Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
```

```
            130                 135                 140
Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
            210

<210> SEQ ID NO 124
<211> LENGTH: 444
<212> TYPE: PRT
<213> ORGANISM: Artificial Sequence
<220> FEATURE:
<223> OTHER INFORMATION: synthetic polypeptide

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Tyr Ile Asn Pro Ser Ser Gly Tyr Thr Lys Ser Asn Gln Lys Phe
    50                  55                  60

Lys Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Trp Leu Leu Ser Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
```

```
                275                 280                 285
Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 125
<211> LENGTH: 445
<212> TYPE: PRT
<213> ORGANISM: Artificial Sequence
<220> FEATURE:
<223> OTHER INFORMATION: synthetic polypeptide

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Tyr Ile Asn Pro Ser Ser Gly Tyr Thr Lys Ser Asn Gln Lys Phe
    50                  55                  60

Lys Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Trp Leu Leu Ser Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
```

```
                195                 200                 205
Asn Thr Lys Val Asp Lys Arg Val Glu Ser Lys Tyr Gly Pro Pro Cys
    210                 215                 220
Pro Pro Cys Pro Ala Pro Glu Phe Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys
        435                 440                 445

<210> SEQ ID NO 126
<211> LENGTH: 444
<212> TYPE: PRT
<213> ORGANISM: Artificial Sequence
<220> FEATURE:
<223> OTHER INFORMATION: synthetic polypeptide

<400> SEQUENCE: 126

Gln Val Gln Leu Gln Gln Ser Gly Ala Glu Val Lys Lys Pro Gly Ala
1               5                   10                  15
Ser Val Lys Leu Ser Cys Lys Ala Ser Gly Tyr Thr Phe Thr Ser Tyr
            20                  25                  30
Trp Met His Trp Val Arg Gln Arg Pro Gly Gln Gly Leu Glu Trp Ile
        35                  40                  45
Gly Tyr Ile Asn Pro Ser Ser Gly Tyr Thr Lys Ser Asn Gln Lys Phe
    50                  55                  60
Lys Asp Arg Ala Thr Leu Thr Ala Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Gly Arg Trp Leu Leu Ser Ala Trp Phe Ala Tyr Trp Gly Gln Gly Thr
            100                 105                 110
Leu Val Thr Val Ser Ser Ala Ser Thr Lys Gly Pro Ser Val Phe Pro
```

```
            115                 120                 125
Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Asn Phe Gly Thr Gln Thr Tyr Thr Cys Asn Val Asp His Lys Pro Ser
    195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Gln Phe
        260                 265                 270

Asn Trp Tyr Val Asp Gly Val Glu Val His Asn Ala Lys Thr Lys Pro
    275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
            325                 330                 335

Lys Gly Gln Pro Arg Glu Pro Gln Val Tyr Thr Leu Pro Pro Ser Arg
        340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
        420                 425                 430

Tyr Thr Gln Lys Ser Leu Ser Leu Ser Pro Gly Lys
    435                 440

<210> SEQ ID NO 127
<211> LENGTH: 445
<212> TYPE: PRT
<213> ORGANISM: Artificial Sequence
<220> FEATURE:
<223> OTHER INFORMATION: synthetic polypeptide

<400> SEQUENCE: 127

Gln Val Gln Leu Gln Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Arg Pro Gly Gln Gly Leu Glu Trp Ile
```

```
                35                  40                  45
Gly Tyr Ile Asn Pro Ser Ser Gly Tyr Thr Lys Ser Asn Gln Lys Phe
 50                  55                  60
Lys Asp Arg Ala Thr Leu Thr Ala Asp Thr Ser Ser Thr Ala Tyr
 65                  70                  75                  80
Met Glu Leu Ser Ser Leu Arg Ser Glu Asp Thr Ala Val Tyr Tyr Cys
                 85                  90                  95
Gly Arg Trp Leu Leu Ser Ala Trp Phe Ala Tyr Trp Gly Gln Gly Thr
                100                 105                 110
Leu Val Thr Val Ser Ser Ala Ser Thr Lys Gly Pro Ser Val Phe Pro
                115                 120                 125
Leu Ala Pro Cys Ser Arg Ser Thr Ser Glu Ser Thr Ala Ala Leu Gly
                130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Lys Thr Tyr Thr Cys Asn Val Asp His Lys Pro Ser
                195                 200                 205
Asn Thr Lys Val Asp Lys Arg Val Glu Ser Lys Tyr Gly Pro Pro Cys
210                 215                 220
Pro Pro Cys Pro Ala Pro Glu Phe Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
                260                 265                 270
Phe Asn Trp Tyr Val Asp Gly Val Glu Val His Asn Ala Lys Thr Lys
                275                 280                 285
Pro Arg Glu Glu Gln Phe Asn Ser Thr Tyr Arg Val Val Ser Val Leu
                290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Gln Glu Glu Met Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
                370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
                420                 425                 430
His Tyr Thr Gln Lys Ser Leu Ser Leu Ser Leu Gly Lys
                435                 440                 445
```